(12) United States Patent
Fukuyama et al.

(10) Patent No.: US 10,337,041 B2
(45) Date of Patent: Jul. 2, 2019

(54) COMPOSITIONS FOR PRODUCING GLUCOSE SYRUPS

(71) Applicant: Novozymes A/S, Bagsvaerd (DK)

(72) Inventors: Shiro Fukuyama, Chiba (JP); Keiichi Ayabe, Konakadaicho (JP)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 15/116,006

(22) PCT Filed: Feb. 6, 2015

(86) PCT No.: PCT/EP2015/052545
§ 371 (c)(1),
(2) Date: Aug. 2, 2016

(87) PCT Pub. No.: WO2015/118123
PCT Pub. Date: Aug. 13, 2015

(65) Prior Publication Data
US 2017/0159090 A1   Jun. 8, 2017

(30) Foreign Application Priority Data

Feb. 7, 2014  (EP) .................................... 14154239
Dec. 1, 2014  (EP) .................................... 14195687

(51) Int. Cl.
| | | |
|---|---|---|
| C12P 19/14 | (2006.01) | |
| C12N 9/34 | (2006.01) | |
| C12P 19/02 | (2006.01) | |
| C12N 9/44 | (2006.01) | |
| C12N 9/24 | (2006.01) | |
| A23L 29/30 | (2016.01) | |
| C13K 1/06 | (2006.01) | |
| C12N 9/26 | (2006.01) | |

(52) U.S. Cl.
CPC .............. *C12P 19/14* (2013.01); *A23L 29/35* (2016.08); *C12N 9/2402* (2013.01); *C12N 9/2411* (2013.01); *C12N 9/2428* (2013.01); *C12N 9/2457* (2013.01); *C12P 19/02* (2013.01); *C12Y 302/01001* (2013.01); *C12Y 302/01003* (2013.01); *C12Y 302/01041* (2013.01); *C13K 1/06* (2013.01)

(58) Field of Classification Search
CPC ..... C12P 19/14; C12N 9/2411; C12N 9/2457; C12N 9/2428
See application file for complete search history.

(56) References Cited

U.S. PATENT DOCUMENTS

| | | |
|---|---|---|
| 4,335,208 A | 6/1982 | Norman |
| 5,817,498 A | 10/1998 | Deweer |
| 6,074,854 A | 6/2000 | Deweer |
| 7,883,883 B2 | 2/2011 | Udagawa |
| 7,998,709 B2 * | 8/2011 | Viksoe-Nielsen ... C12N 9/2408 435/105 |
| 2006/0148054 A1 | 7/2006 | Fukuyama |

FOREIGN PATENT DOCUMENTS

| | | | |
|---|---|---|---|
| CN | 101049133 A | 10/2007 | |
| JP | 2012223189 | 11/2012 | |
| KR | 20120071529 | 7/2012 | |
| WO | 1997/041213 A1 | 11/1997 | |
| WO | 98/03639 A1 | 1/1998 | |
| WO | 2002/038787 A2 | 5/2002 | |
| WO | 2005/113785 A2 | 12/2005 | |
| WO | 2006/060062 A2 | 6/2006 | |
| WO | 2007/144393 A1 | 12/2007 | |
| WO | 2009/075682 A1 | 6/2009 | |
| WO | 2011/068803 A1 | 6/2011 | |
| WO | 2011/127802 A1 | 10/2011 | |
| WO | 2013/055676 A1 | 4/2013 | |
| WO | 2013/160349 A2 | 10/2013 | |
| WO | WO 2014/177546 A2 * | 11/2014 | ............... C12N 9/34 |
| WO | WO 2015/031477 A1 * | 3/2015 | ............... C12N 9/00 |
| WO | WO 2015/110473 A2 * | 7/2015 | ............... C12N 9/44 |

OTHER PUBLICATIONS

Brown et al., Characterization of amylolytic enzyme activities associated with the hyperthermophilic archaebacterium Pyrococcus furiosus. Appl. Environ. Microbiol., 1990, vol. 56(7): 1985-1991.*
Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Seffernick et al., Melamine deaminase and Atrazine chlorohydrolase: 98 percent identical but functionally different. J. Bacteriol., 2001, vol. 183 (8): 2405-2410.*

(Continued)

*Primary Examiner* — Ganapathirama Raghu
(74) *Attorney, Agent, or Firm* — Elias Lambiris

(57) ABSTRACT

The present invention relates to a method of making glucose syrup from liquefied starch comprising, (a) contacting the liquefied starch with a glucoamylase, a pullulanase, and optionally an alpha-amylase wherein the ratio of pullulanase dose expressed as NPUN/gDS, to alpha-amylase dose expressed as FAU(A)/gDS is at least 60, particularly at least 75, particularly at least 100, more particularly at least 150, more particularly at least 200, more particularly at least 250, more particularly at least 300, more particularly at least 400, more particularly at least 500, more particularly at least 600, more particularly at least 800 or if no alpha-amylase is present the pullulanse is present in a dose of at least 0.5, particularly at least 0.75, particularly at least 1.0, particularly at least 1.5 NPUN/gDS, and (b) saccharifying the liquefied starch.

15 Claims, No Drawings
Specification includes a Sequence Listing.

(56) References Cited

OTHER PUBLICATIONS

Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
Guo et al., Protein tolerance to random amino acid change. PNAS., 2004, vol. 101 (25): 9205-9210. (Year: 2004).*
Anonymous, 2011, NCBI Reference seqence XP-001390530.1.
Nie et al, 2013, NCBI Reference sequence No. AEV53626.
Zeng et al, 2011, NCBI Reference sequence No. ADX42122.1.
Turkenburg et al, 2012, NCBI Accession No. 2WAN_A.

* cited by examiner

SEQUENCE LISTING

```
<160> NUMBER OF SEQ ID NOS: 25

<210> SEQ ID NO 1
<211> LENGTH: 616
<212> TYPE: PRT
<213> ORGANISM: Aspergillus niger

<400> SEQUENCE: 1

Ala Thr Leu Asp Ser Trp Leu Ser Asn Glu Ala Thr Val Ala Arg Thr
1               5                   10                  15

Ala Ile Leu Asn Asn Ile Gly Ala Asp Gly Ala Trp Val Ser Gly Ala
                20                  25                  30

Asp Ser Gly Ile Val Val Ala Ser Pro Ser Thr Asp Asn Pro Asp Tyr
            35                  40                  45

Phe Tyr Thr Trp Thr Arg Asp Ser Gly Leu Val Leu Lys Thr Leu Val
        50                  55                  60

Asp Leu Phe Arg Asn Gly Asp Thr Ser Leu Leu Ser Thr Ile Glu Asn
65                  70                  75                  80

Tyr Ile Ser Ala Gln Ala Ile Val Gln Gly Ile Ser Asn Pro Ser Gly
                85                  90                  95

Asp Leu Ser Ser Gly Ala Gly Leu Gly Glu Pro Lys Phe Asn Val Asp
            100                 105                 110

Glu Thr Ala Tyr Thr Gly Ser Trp Gly Arg Pro Gln Arg Asp Gly Pro
        115                 120                 125

Ala Leu Arg Ala Thr Ala Met Ile Gly Phe Gly Gln Trp Leu Leu Asp
    130                 135                 140

Asn Gly Tyr Thr Ser Thr Ala Thr Asp Ile Val Trp Pro Leu Val Arg
145                 150                 155                 160

Asn Asp Leu Ser Tyr Val Ala Gln Tyr Trp Asn Gln Thr Gly Tyr Asp
                165                 170                 175

Leu Trp Glu Glu Val Asn Gly Ser Ser Phe Phe Thr Ile Ala Val Gln
            180                 185                 190

His Arg Ala Leu Val Glu Gly Ser Ala Phe Ala Thr Ala Val Gly Ser
        195                 200                 205

Ser Cys Ser Trp Cys Asp Ser Gln Ala Pro Glu Ile Leu Cys Tyr Leu
    210                 215                 220
```

Gln Ser Phe Trp Thr Gly Ser Phe Ile Leu Ala Asn Phe Asp Ser Ser
225                 230                 235                 240

Arg Ser Gly Lys Asp Ala Asn Thr Leu Leu Gly Ser Ile His Thr Phe
            245                 250                 255

Asp Pro Glu Ala Ala Cys Asp Asp Ser Thr Phe Gln Pro Cys Ser Pro
        260                 265                 270

Arg Ala Leu Ala Asn His Lys Glu Val Val Asp Ser Phe Arg Ser Ile
    275                 280                 285

Tyr Thr Leu Asn Asp Gly Leu Ser Asp Ser Glu Ala Val Ala Val Gly
    290                 295                 300

Arg Tyr Pro Glu Asp Thr Tyr Tyr Asn Gly Asn Pro Trp Phe Leu Cys
305                 310                 315                 320

Thr Leu Ala Ala Ala Glu Gln Leu Tyr Asp Ala Leu Tyr Gln Trp Asp
            325                 330                 335

Lys Gln Gly Ser Leu Glu Val Thr Asp Val Ser Leu Asp Phe Phe Lys
            340                 345                 350

Ala Leu Tyr Ser Asp Ala Ala Thr Gly Thr Tyr Ser Ser Ser Ser Ser
        355                 360                 365

Thr Tyr Ser Ser Ile Val Asp Ala Val Lys Thr Phe Ala Asp Gly Phe
    370                 375                 380

Val Ser Ile Val Glu Thr His Ala Ala Ser Asn Gly Ser Met Ser Glu
385                 390                 395                 400

Gln Tyr Asp Lys Ser Asp Gly Glu Gln Leu Ser Ala Arg Asp Leu Thr
                405                 410                 415

Trp Ser Tyr Ala Ala Leu Leu Thr Ala Asn Asn Arg Arg Asn Ser Val
            420                 425                 430

Val Pro Ala Ser Trp Gly Glu Thr Ser Ala Ser Ser Val Pro Gly Thr
        435                 440                 445

Cys Ala Ala Thr Ser Ala Ile Gly Thr Tyr Ser Ser Val Thr Val Thr
    450                 455                 460

Ser Trp Pro Ser Ile Val Ala Thr Gly Gly Thr Thr Thr Thr Ala Thr
465                 470                 475                 480

Pro Thr Gly Ser Gly Ser Val Thr Ser Thr Ser Lys Thr Thr Ala Thr
                485                 490                 495

Ala Ser Lys Thr Ser Thr Ser Thr Ser Ser Thr Ser Cys Thr Thr Pro
            500                 505                 510

Thr Ala Val Ala Val Thr Phe Asp Leu Thr Ala Thr Thr Thr Tyr Gly
        515                 520                 525

Glu Asn Ile Tyr Leu Val Gly Ser Ile Ser Gln Leu Gly Asp Trp Glu
    530                 535                 540

Thr Ser Asp Gly Ile Ala Leu Ser Ala Asp Lys Tyr Thr Ser Ser Asp
545                 550                 555                 560

Pro Leu Trp Tyr Val Thr Val Thr Leu Pro Ala Gly Glu Ser Phe Glu
                565                 570                 575

Tyr Lys Phe Ile Arg Ile Glu Ser Asp Asp Ser Val Glu Trp Glu Ser
            580                 585                 590

Asp Pro Asn Arg Glu Tyr Thr Val Pro Gln Ala Cys Gly Thr Ser Thr
        595                 600                 605

Ala Thr Val Thr Asp Thr Trp Arg
    610                 615

<210> SEQ ID NO 2
<211> LENGTH: 484
<212> TYPE: PRT

<213> ORGANISM: Aspergillus niger

<400> SEQUENCE: 2

```
Leu Ser Ala Ala Glu Trp Arg Thr Gln Ser Ile Tyr Phe Leu Leu Thr
 1               5                  10                  15

Asp Arg Phe Gly Arg Thr Asp Asn Ser Thr Thr Ala Thr Cys Asp Thr
            20                  25                  30

Gly Asp Gln Ile Tyr Cys Gly Gly Ser Trp Gln Gly Ile Ile Asn His
        35                  40                  45

Leu Asp Tyr Ile Gln Gly Met Gly Phe Thr Ala Ile Trp Ile Ser Pro
    50                  55                  60

Ile Thr Glu Gln Leu Pro Gln Asp Thr Ala Asp Gly Glu Ala Tyr His
65                  70                  75                  80

Gly Tyr Trp Gln Gln Lys Ile Tyr Asp Val Asn Ser Asn Phe Gly Thr
                85                  90                  95

Ala Asp Asp Leu Lys Ser Leu Ser Asp Ala Leu His Ala Arg Gly Met
            100                 105                 110

Tyr Leu Met Val Asp Val Val Pro Asn His Met Gly Tyr Ala Gly Asn
        115                 120                 125

Gly Asn Asp Val Asp Tyr Ser Val Phe Asp Pro Phe Asp Ser Ser Ser
    130                 135                 140

Tyr Phe His Pro Tyr Cys Leu Ile Thr Asp Trp Asp Asn Leu Thr Met
145                 150                 155                 160

Val Gln Asp Cys Trp Glu Gly Asp Thr Ile Val Ser Leu Pro Asp Leu
                165                 170                 175

Asn Thr Thr Glu Thr Ala Val Arg Thr Ile Trp Tyr Asp Trp Val Ala
            180                 185                 190

Asp Leu Val Ser Asn Tyr Ser Val Asp Gly Leu Arg Ile Asp Ser Val
        195                 200                 205

Leu Glu Val Glu Pro Asp Phe Phe Pro Gly Tyr Gln Glu Ala Ala Gly
    210                 215                 220

Val Tyr Cys Val Gly Glu Val Asp Asn Gly Asn Pro Ala Leu Asp Cys
225                 230                 235                 240

Pro Tyr Gln Lys Val Leu Asp Gly Val Leu Asn Tyr Pro Ile Tyr Trp
                245                 250                 255

Gln Leu Leu Tyr Ala Phe Glu Ser Ser Gly Ser Ile Ser Asn Leu
            260                 265                 270

Tyr Asn Met Ile Lys Ser Val Ala Ser Asp Cys Ser Asp Pro Thr Leu
        275                 280                 285

Leu Gly Asn Phe Ile Glu Asn His Asp Asn Pro Arg Phe Ala Ser Tyr
    290                 295                 300

Thr Ser Asp Tyr Ser Gln Ala Lys Asn Val Leu Ser Tyr Ile Phe Leu
305                 310                 315                 320

Ser Asp Gly Ile Pro Ile Val Tyr Ala Gly Glu Glu Gln His Tyr Ser
                325                 330                 335

Gly Gly Lys Val Pro Tyr Asn Arg Glu Ala Thr Trp Leu Ser Gly Tyr
            340                 345                 350

Asp Thr Ser Ala Glu Leu Tyr Thr Trp Ile Ala Thr Asn Ala Ile
        355                 360                 365

Arg Lys Leu Ala Ile Ser Ala Asp Ser Ala Tyr Ile Thr Tyr Ala Asn
    370                 375                 380

Asp Ala Phe Tyr Thr Asp Ser Asn Thr Ile Ala Met Arg Lys Gly Thr
385                 390                 395                 400
```

Ser Gly Ser Gln Val Ile Thr Val Leu Ser Asn Lys Gly Ser Ser Gly
            405                 410                 415

Ser Ser Tyr Thr Leu Thr Leu Ser Gly Ser Gly Tyr Thr Ser Gly Thr
            420                 425                 430

Lys Leu Ile Glu Ala Tyr Thr Cys Thr Ser Val Thr Val Asp Ser Ser
            435                 440                 445

Gly Asp Ile Pro Val Pro Met Ala Ser Gly Leu Pro Arg Val Leu Leu
450                 455                 460

Pro Ala Ser Val Val Asp Ser Ser Leu Cys Gly Gly Ser Gly Arg
465                 470                 475                 480

Leu Tyr Val Glu

<210> SEQ ID NO 3
<211> LENGTH: 928
<212> TYPE: PRT
<213> ORGANISM: Bacillus deramificans

<400> SEQUENCE: 3

Asp Gly Asn Thr Thr Thr Ile Ile Val His Tyr Phe Arg Pro Ala Gly
1               5                   10                  15

Asp Tyr Gln Pro Trp Ser Leu Trp Met Trp Pro Lys Asp Gly Gly Gly
            20                  25                  30

Ala Glu Tyr Asp Phe Asn Gln Pro Ala Asp Ser Phe Gly Ala Val Ala
            35                  40                  45

Ser Ala Asp Ile Pro Gly Asn Pro Ser Gln Val Gly Ile Ile Val Arg
50                  55                  60

Thr Gln Asp Trp Thr Lys Asp Val Ser Ala Asp Arg Tyr Ile Asp Leu
65                  70                  75                  80

Ser Lys Gly Asn Glu Val Trp Leu Val Glu Gly Asn Ser Gln Ile Phe
            85                  90                  95

Tyr Asn Glu Lys Asp Ala Glu Asp Ala Ala Lys Pro Ala Val Ser Asn
            100                 105                 110

Ala Tyr Leu Asp Ala Ser Asn Gln Val Leu Val Lys Leu Ser Gln Pro
            115                 120                 125

Leu Thr Leu Gly Glu Gly Ala Ser Gly Phe Thr Val His Asp Asp Thr
130                 135                 140

Ala Asn Lys Asp Ile Pro Val Thr Ser Val Lys Asp Ala Ser Leu Gly
145                 150                 155                 160

Gln Asp Val Thr Ala Val Leu Ala Gly Thr Phe Gln His Ile Phe Gly
            165                 170                 175

Gly Ser Asp Trp Ala Pro Asp Asn His Ser Thr Leu Leu Lys Lys Val
            180                 185                 190

Thr Asn Asn Leu Tyr Gln Phe Ser Gly Asp Leu Pro Glu Gly Asn Tyr
            195                 200                 205

Gln Tyr Lys Val Ala Leu Asn Asp Ser Trp Asn Asn Pro Ser Tyr Pro
            210                 215                 220

Ser Asp Asn Ile Asn Leu Thr Val Pro Ala Gly Gly Ala His Val Thr
225                 230                 235                 240

Phe Ser Tyr Ile Pro Ser Thr His Ala Val Tyr Asp Thr Ile Asn Asn
            245                 250                 255

Pro Asn Ala Asp Leu Gln Val Glu Ser Gly Val Lys Thr Asp Leu Val
            260                 265                 270

Thr Val Thr Leu Gly Glu Asp Pro Asp Val Ser His Thr Leu Ser Ile
            275                 280                 285

```
Gln Thr Asp Gly Tyr Gln Ala Lys Gln Val Ile Pro Arg Asn Val Leu
    290                 295                 300

Asn Ser Ser Gln Tyr Tyr Tyr Ser Gly Asp Asp Leu Gly Asn Thr Tyr
305                 310                 315                 320

Thr Gln Lys Ala Thr Thr Phe Lys Val Trp Ala Pro Thr Ser Thr Gln
                325                 330                 335

Val Asn Val Leu Leu Tyr Asp Ser Ala Thr Gly Ser Val Thr Lys Ile
            340                 345                 350

Val Pro Met Thr Ala Ser Gly His Gly Val Trp Glu Ala Thr Val Asn
        355                 360                 365

Gln Asn Leu Glu Asn Trp Tyr Tyr Met Tyr Glu Val Thr Gly Gln Gly
    370                 375                 380

Ser Thr Arg Thr Ala Val Asp Pro Tyr Ala Thr Ala Ile Ala Pro Asn
385                 390                 395                 400

Gly Thr Arg Gly Met Ile Val Asp Leu Ala Lys Thr Asp Pro Ala Gly
                405                 410                 415

Trp Asn Ser Asp Lys His Ile Thr Pro Lys Asn Ile Glu Asp Glu Val
            420                 425                 430

Ile Tyr Glu Met Asp Val Arg Asp Phe Ser Ile Asp Pro Asn Ser Gly
        435                 440                 445

Met Lys Asn Lys Gly Lys Tyr Leu Ala Leu Thr Glu Lys Gly Thr Lys
    450                 455                 460

Gly Pro Asp Asn Val Lys Thr Gly Ile Asp Ser Leu Lys Gln Leu Gly
465                 470                 475                 480

Ile Thr His Val Gln Leu Met Pro Val Phe Ala Ser Asn Ser Val Asp
                485                 490                 495

Glu Thr Asp Pro Thr Gln Asp Asn Trp Gly Tyr Asp Pro Arg Asn Tyr
            500                 505                 510

Asp Val Pro Glu Gly Gln Tyr Ala Thr Asn Ala Asn Gly Asn Ala Arg
        515                 520                 525

Ile Lys Glu Phe Lys Glu Met Val Leu Ser Leu His Arg Glu His Ile
    530                 535                 540

Gly Val Asn Met Asp Val Val Tyr Asn His Thr Phe Ala Thr Gln Ile
545                 550                 555                 560

Ser Asp Phe Asp Lys Ile Val Pro Glu Tyr Tyr Arg Thr Asp Asp
                565                 570                 575

Ala Gly Asn Tyr Thr Asn Gly Ser Gly Thr Gly Asn Glu Ile Ala Ala
            580                 585                 590

Glu Arg Pro Met Val Gln Lys Phe Ile Ile Asp Ser Leu Lys Tyr Trp
        595                 600                 605

Val Asn Glu Tyr His Ile Asp Gly Phe Arg Phe Asp Leu Met Ala Leu
    610                 615                 620

Leu Gly Lys Asp Thr Met Ser Lys Ala Ala Ser Glu Leu His Ala Ile
625                 630                 635                 640

Asn Pro Gly Ile Ala Leu Tyr Gly Glu Pro Trp Thr Gly Gly Thr Ser
                645                 650                 655

Ala Leu Pro Asp Asp Gln Leu Leu Thr Lys Gly Ala Gln Lys Gly Met
            660                 665                 670

Gly Val Ala Val Phe Asn Asp Asn Leu Arg Asn Ala Leu Asp Gly Asn
        675                 680                 685

Val Phe Asp Ser Ser Ala Gln Gly Phe Ala Thr Gly Ala Thr Gly Leu
    690                 695                 700

Thr Asp Ala Ile Lys Asn Gly Val Glu Gly Ser Ile Asn Asp Phe Thr
```

```
                705                 710                 715                 720
Ser Ser Pro Gly Glu Thr Ile Asn Tyr Val Thr Ser His Asp Asn Tyr
                            725                 730                 735

Thr Leu Trp Asp Lys Ile Ala Leu Ser Asn Pro Asn Asp Ser Glu Ala
                    740                 745                 750

Asp Arg Ile Lys Met Asp Glu Leu Ala Gln Ala Val Met Thr Ser
                755                 760                 765

Gln Gly Val Pro Phe Met Gln Gly Glu Met Leu Arg Thr Lys
        770                 775                 780

Gly Gly Asn Asp Asn Ser Tyr Asn Ala Gly Asp Ala Val Asn Glu Phe
785                 790                 795                 800

Asp Trp Ser Arg Lys Ala Gln Tyr Pro Asp Val Phe Asn Tyr Tyr Ser
                    805                 810                 815

Gly Leu Ile His Leu Arg Leu Asp His Pro Ala Phe Arg Met Thr Thr
                820                 825                 830

Ala Asn Glu Ile Asn Ser His Leu Gln Phe Leu Asn Ser Pro Glu Asn
                835                 840                 845

Thr Val Ala Tyr Glu Leu Thr Asp His Val Asn Lys Asp Lys Trp Gly
        850                 855                 860

Asn Ile Ile Val Val Tyr Asn Pro Asn Lys Thr Val Ala Thr Ile Asn
865                 870                 875                 880

Leu Pro Ser Gly Lys Trp Ala Ile Asn Ala Thr Ser Gly Lys Val Gly
                885                 890                 895

Glu Ser Thr Leu Gly Gln Ala Glu Gly Ser Val Gln Val Pro Gly Ile
                900                 905                 910

Ser Met Met Ile Leu His Gln Glu Val Ser Pro Asp His Gly Lys Lys
                915                 920                 925

<210> SEQ ID NO 4
<211> LENGTH: 559
<212> TYPE: PRT
<213> ORGANISM: Gloeophyllum trabeum

<400> SEQUENCE: 4

Gln Ser Val Asp Ser Tyr Val Gly Ser Glu Gly Pro Ile Ala Lys Ala
1               5                   10                  15

Gly Val Leu Ala Asn Ile Gly Pro Asn Gly Ser Lys Ala Ser Gly Ala
                20                  25                  30

Ala Ala Gly Val Val Val Ala Ser Pro Ser Lys Ser Asp Pro Asp Tyr
            35                  40                  45

Trp Tyr Thr Trp Thr Arg Asp Ser Ser Leu Val Phe Lys Ser Leu Ile
    50                  55                  60

Asp Gln Tyr Thr Thr Gly Ile Asp Ser Thr Ser Ser Leu Arg Ser Leu
65                  70                  75                  80

Ile Asp Ser Phe Val Ile Ala Glu Ala Asn Ile Gln Gln Val Pro Asn
                85                  90                  95

Pro Ser Gly Thr Leu Thr Gly Gly Leu Gly Glu Pro Lys Phe Asn
            100                 105                 110

Val Asp Glu Thr Ala Phe Thr Gly Pro Trp Gly Arg Pro Gln Arg Asp
        115                 120                 125

Gly Pro Ala Leu Arg Ala Thr Ala Leu Ile Thr Tyr Gly Asn Trp Leu
    130                 135                 140

Leu Ser Asn Gly Asn Thr Thr Trp Val Thr Ser Thr Leu Trp Pro Ile
145                 150                 155                 160
```

```
Ile Gln Asn Asp Leu Asn Tyr Val Val Gln Tyr Trp Asn Gln Thr Thr
                165                 170                 175

Phe Asp Leu Trp Glu Val Asn Ser Ser Phe Thr Thr Ala
        180                 185                 190

Val Gln His Arg Ala Leu Arg Glu Gly Ala Ala Phe Ala Thr Lys Ile
        195                 200                 205

Gly Gln Thr Ser Ser Val Ser Ser Tyr Thr Thr Gln Ala Ala Asn Leu
        210                 215                 220

Leu Cys Phe Leu Gln Ser Tyr Trp Asn Pro Thr Ser Gly Tyr Ile Thr
225                 230                 235                 240

Ala Asn Thr Gly Gly Gly Arg Ser Gly Lys Asp Ala Asn Thr Leu Leu
                245                 250                 255

Ala Ser Ile His Thr Tyr Asp Pro Ser Ala Gly Cys Asp Ala Thr Thr
                260                 265                 270

Phe Gln Pro Cys Ser Asp Lys Ala Leu Ser Asn Leu Lys Val Tyr Val
                275                 280                 285

Asp Ser Phe Arg Ser Val Tyr Ser Ile Asn Ser Gly Ile Ala Ser Asn
            290                 295                 300

Ala Ala Val Ala Thr Gly Arg Tyr Pro Glu Asp Ser Tyr Gln Gly Gly
305                 310                 315                 320

Asn Pro Trp Tyr Leu Thr Thr Phe Ala Val Ala Glu Gln Leu Tyr Asp
                325                 330                 335

Ala Leu Asn Val Trp Ala Ala Gln Gly Ser Leu Asn Val Thr Ser Ile
                340                 345                 350

Ser Leu Pro Phe Phe Gln Gln Phe Ser Ser Ser Val Thr Ala Gly Thr
                355                 360                 365

Tyr Ala Ser Ser Ser Thr Thr Tyr Thr Thr Leu Thr Ser Ala Ile Lys
            370                 375                 380

Ser Phe Ala Asp Gly Phe Val Ala Ile Asn Ala Gln Tyr Thr Pro Ser
385                 390                 395                 400

Asn Gly Gly Leu Ala Glu Gln Phe Ser Arg Ser Asn Gly Ala Pro Val
                405                 410                 415

Ser Ala Val Asp Leu Thr Trp Ser Tyr Ala Ser Ala Leu Thr Ala Phe
                420                 425                 430

Glu Ala Arg Asn Asn Thr Gln Phe Ala Gly Trp Gly Ala Val Gly Leu
                435                 440                 445

Thr Val Pro Thr Ser Cys Ser Ser Asn Ser Gly Gly Gly Gly Gly Ser
            450                 455                 460

Thr Val Ala Val Thr Phe Asn Val Asn Ala Gln Thr Val Trp Gly Glu
465                 470                 475                 480

Asn Ile Tyr Ile Thr Gly Ser Val Asp Ala Leu Ser Asn Trp Ser Pro
                485                 490                 495

Asp Asn Ala Leu Leu Leu Ser Ser Ala Asn Tyr Pro Thr Trp Ser Ile
                500                 505                 510

Thr Val Asn Leu Pro Ala Ser Thr Ala Ile Gln Tyr Lys Tyr Ile Arg
                515                 520                 525

Lys Asn Asn Gly Ala Val Thr Trp Glu Ser Asp Pro Asn Asn Ser Ile
            530                 535                 540

Thr Thr Pro Ala Ser Gly Ser Val Thr Glu Asn Asp Thr Trp Arg
545                 550                 555

<210> SEQ ID NO 5
<211> LENGTH: 583
<212> TYPE: PRT
```

<213> ORGANISM: Rhizomucor pusillus

<400> SEQUENCE: 5

```
Ala Thr Ser Asp Asp Trp Lys Gly Lys Ala Ile Tyr Gln Leu Leu Thr
1               5                   10                  15
Asp Arg Phe Gly Arg Ala Asp Asp Ser Thr Ser Asn Cys Ser Asn Leu
            20                  25                  30
Ser Asn Tyr Cys Gly Gly Thr Tyr Glu Gly Ile Thr Lys His Leu Asp
        35                  40                  45
Tyr Ile Ser Gly Met Gly Phe Asp Ala Ile Trp Ile Ser Pro Ile Pro
    50                  55                  60
Lys Asn Ser Asp Gly Gly Tyr His Gly Tyr Trp Ala Thr Asp Phe Tyr
65                  70                  75                  80
Gln Leu Asn Ser Asn Phe Gly Asp Glu Ser Gln Leu Lys Ala Leu Ile
                85                  90                  95
Gln Ala Ala His Glu Arg Asp Met Tyr Val Met Leu Asp Val Val Ala
            100                 105                 110
Asn His Ala Gly Pro Thr Ser Asn Gly Tyr Ser Gly Tyr Thr Phe Asp
        115                 120                 125
Asp Ala Ser Leu Tyr His Pro Lys Cys Thr Ile Asp Tyr Asn Asn Gln
    130                 135                 140
Thr Ser Ile Glu Gln Cys Trp Val Ala Asp Glu Leu Pro Asp Ile Asp
145                 150                 155                 160
Thr Glu Asn Ser Asp Asn Val Ala Ile Leu Asn Asp Ile Val Ser Gly
                165                 170                 175
Trp Val Gly Asn Tyr Ser Phe Asp Gly Ile Arg Ile Asp Thr Val Lys
            180                 185                 190
His Ile Arg Lys Asp Phe Trp Thr Gly Tyr Ala Glu Ala Ala Gly Val
        195                 200                 205
Phe Ala Thr Gly Glu Val Phe Asn Gly Asp Pro Ala Tyr Val Gly Pro
    210                 215                 220
Tyr Gln Lys Tyr Leu Pro Ser Leu Ile Asn Tyr Pro Met Tyr Tyr Ala
225                 230                 235                 240
Leu Asn Asp Val Phe Val Ser Lys Ser Lys Gly Phe Ser Arg Ile Ser
                245                 250                 255
Glu Met Leu Gly Ser Asn Arg Asn Ala Phe Glu Asp Thr Ser Val Leu
            260                 265                 270
Thr Thr Phe Val Asp Asn His Asp Asn Pro Arg Phe Leu Asn Ser Gln
        275                 280                 285
Ser Asp Lys Ala Leu Phe Lys Asn Ala Leu Thr Tyr Val Leu Leu Gly
    290                 295                 300
Glu Gly Ile Pro Ile Val Tyr Tyr Gly Ser Glu Gln Gly Phe Ser Gly
305                 310                 315                 320
Gly Ala Asp Pro Ala Asn Arg Glu Val Leu Trp Thr Thr Asn Tyr Asp
                325                 330                 335
Thr Ser Ser Asp Leu Tyr Gln Phe Ile Lys Thr Val Asn Ser Val Arg
            340                 345                 350
Met Lys Ser Asn Lys Ala Val Tyr Met Asp Ile Tyr Val Gly Asp Asn
        355                 360                 365
Ala Tyr Ala Phe Lys His Gly Asp Ala Leu Val Val Leu Asn Asn Tyr
    370                 375                 380
Gly Ser Gly Ser Thr Asn Gln Val Ser Phe Ser Val Ser Gly Lys Phe
385                 390                 395                 400
```

```
Asp Ser Gly Ala Ser Leu Met Asp Ile Val Ser Asn Ile Thr Thr Thr
                405                 410                 415

Val Ser Ser Asp Gly Thr Val Thr Phe Asn Leu Lys Asp Gly Leu Pro
            420                 425                 430

Ala Ile Phe Thr Ser Ala Thr Gly Gly Thr Thr Thr Ala Thr Pro
        435                 440                 445

Thr Gly Ser Gly Ser Val Thr Ser Ser Lys Thr Thr Ala Thr Ala
    450                 455                 460

Ser Lys Thr Ser Thr Ser Thr Ser Ser Thr Ser Cys Thr Thr Pro Thr
465                 470                 475                 480

Ala Val Ala Val Thr Phe Asp Leu Thr Ala Thr Thr Thr Tyr Gly Glu
                485                 490                 495

Asn Ile Tyr Leu Val Gly Ser Ile Ser Gln Leu Gly Asp Trp Glu Thr
            500                 505                 510

Ser Asp Gly Ile Ala Leu Ser Ala Asp Lys Tyr Thr Ser Ser Asp Pro
        515                 520                 525

Leu Trp Tyr Val Thr Val Thr Leu Pro Ala Gly Glu Ser Phe Glu Tyr
    530                 535                 540

Lys Phe Ile Arg Ile Glu Ser Asp Asp Ser Val Glu Trp Glu Ser Asp
545                 550                 555                 560

Pro Asn Arg Glu Tyr Thr Val Pro Gln Ala Cys Gly Thr Ser Thr Ala
                565                 570                 575

Thr Val Thr Asp Thr Trp Arg
            580

<210> SEQ ID NO 6
<211> LENGTH: 573
<212> TYPE: PRT
<213> ORGANISM: Gloeophyllum sepiarium

<400> SEQUENCE: 6

Met Tyr Arg Phe Leu Val Cys Ala Leu Gly Leu Ala Ala Ser Val Leu
1               5                   10                  15

Ala Gln Ser Val Asp Ser Tyr Val Ser Ser Glu Gly Pro Ile Ala Lys
            20                  25                  30

Ala Gly Val Leu Ala Asn Ile Gly Pro Asn Gly Ser Lys Ala Ser Gly
        35                  40                  45

Ala Ser Ala Gly Val Val Ala Ser Pro Ser Thr Ser Asp Pro Asp
    50                  55                  60

Tyr Trp Tyr Thr Trp Thr Arg Asp Ser Ser Leu Val Phe Lys Ser Leu
65                  70                  75                  80

Ile Asp Gln Tyr Thr Thr Gly Ile Asp Ser Thr Ser Ser Leu Arg Thr
                85                  90                  95

Leu Ile Asp Asp Phe Val Thr Ala Glu Ala Asn Leu Gln Gln Val Ser
            100                 105                 110

Asn Pro Ser Gly Thr Leu Thr Gly Gly Leu Gly Glu Pro Lys Phe
        115                 120                 125

Asn Val Asp Glu Thr Ala Phe Thr Gly Ala Trp Gly Arg Pro Gln Arg
    130                 135                 140

Asp Gly Pro Ala Leu Arg Ser Thr Ala Leu Ile Thr Tyr Gly Asn Trp
145                 150                 155                 160

Leu Leu Ser Asn Gly Asn Thr Ser Tyr Val Thr Ser Asn Leu Trp Pro
                165                 170                 175

Ile Ile Gln Asn Asp Leu Gly Tyr Val Val Ser Tyr Trp Asn Gln Ser
            180                 185                 190
```

```
Thr Tyr Asp Leu Trp Glu Glu Val Asp Ser Ser Phe Phe Thr Thr
            195                 200                 205

Ala Val Gln His Arg Ala Leu Arg Glu Gly Ala Ala Phe Ala Thr Ala
        210                 215                 220

Ile Gly Gln Thr Ser Gln Val Ser Ser Tyr Thr Thr Gln Ala Asp Asn
225                 230                 235                 240

Leu Leu Cys Phe Leu Gln Ser Tyr Trp Asn Pro Ser Gly Gly Tyr Ile
                245                 250                 255

Thr Ala Asn Thr Gly Gly Arg Ser Gly Lys Asp Ala Asn Thr Leu
            260                 265                 270

Leu Ala Ser Ile His Thr Tyr Asp Pro Ser Ala Gly Cys Asp Ala Ala
                275                 280                 285

Thr Phe Gln Pro Cys Ser Asp Lys Ala Leu Ser Asn Leu Lys Val Tyr
        290                 295                 300

Val Asp Ser Phe Arg Ser Val Tyr Ser Ile Asn Ser Gly Val Ala Ser
305                 310                 315                 320

Asn Ala Ala Val Ala Thr Gly Arg Tyr Pro Glu Asp Ser Tyr Gln Gly
                325                 330                 335

Gly Asn Pro Trp Tyr Leu Thr Thr Phe Ala Val Ala Glu Gln Leu Tyr
            340                 345                 350

Asp Ala Leu Asn Val Trp Glu Ser Gln Gly Ser Leu Glu Val Thr Ser
                355                 360                 365

Thr Ser Leu Ala Phe Phe Gln Gln Phe Ser Ser Gly Val Thr Ala Gly
        370                 375                 380

Thr Tyr Ser Ser Ser Ser Ser Thr Tyr Ser Thr Leu Thr Ser Ala Ile
385                 390                 395                 400

Lys Asn Phe Ala Asp Gly Phe Val Ala Ile Asn Ala Lys Tyr Thr Pro
                405                 410                 415

Ser Asn Gly Gly Leu Ala Glu Gln Tyr Ser Lys Ser Asp Gly Ser Pro
            420                 425                 430

Leu Ser Ala Val Asp Leu Thr Trp Ser Tyr Ala Ser Ala Leu Thr Ala
        435                 440                 445

Phe Glu Ala Arg Asn Asn Thr Gln Phe Ala Gly Trp Gly Ala Ala Gly
        450                 455                 460

Leu Thr Val Pro Ser Ser Cys Ser Gly Asn Ser Gly Gly Pro Thr Val
465                 470                 475                 480

Ala Val Thr Phe Asn Val Asn Ala Glu Thr Val Trp Gly Glu Asn Ile
                485                 490                 495

Tyr Leu Thr Gly Ser Val Asp Ala Leu Glu Asn Trp Ser Ala Asp Asn
            500                 505                 510

Ala Leu Leu Leu Ser Ser Ala Asn Tyr Pro Thr Trp Ser Ile Thr Val
        515                 520                 525

Asn Leu Pro Ala Ser Thr Ala Ile Glu Tyr Lys Tyr Ile Arg Lys Asn
530                 535                 540

Asn Gly Ala Val Thr Trp Glu Ser Asp Pro Asn Asn Ser Ile Thr Thr
545                 550                 555                 560

Pro Ala Ser Gly Ser Thr Thr Glu Asn Asp Thr Trp Arg
                565                 570

<210> SEQ ID NO 7
<211> LENGTH: 573
<212> TYPE: PRT
<213> ORGANISM: Gloeophyllym sepiarium
```

<400> SEQUENCE: 7

```
Met Tyr Arg Phe Leu Val Cys Ala Leu Gly Leu Ala Ala Ser Val Leu
1               5                   10                  15

Ala Gln Ser Val Asp Ser Tyr Val Ser Ser Glu Gly Pro Ile Ala Lys
            20                  25                  30

Ala Gly Val Leu Ala Asn Ile Gly Pro Asn Gly Ser Lys Ala Ser Gly
        35                  40                  45

Ala Ser Ala Gly Val Val Ala Ser Pro Ser Thr Ser Asp Pro Asp
    50                  55                  60

Tyr Trp Tyr Thr Trp Thr Arg Asp Ser Ser Leu Val Phe Lys Ser Leu
65                  70                  75                  80

Ile Asp Gln Tyr Thr Thr Gly Ile Asp Ser Thr Ser Leu Arg Thr
                85                  90                  95

Leu Ile Asp Asp Phe Val Thr Ala Glu Ala Asn Leu Gln Gln Val Ser
                100                 105                 110

Asn Pro Ser Gly Thr Leu Thr Thr Gly Gly Leu Gly Glu Pro Lys Phe
            115                 120                 125

Asn Val Asp Glu Thr Ala Phe Thr Gly Ala Trp Gly Arg Pro Gln Arg
130                 135                 140

Asp Gly Ser Ala Leu Arg Ser Thr Ala Leu Ile Thr Tyr Gly Asn Trp
145                 150                 155                 160

Leu Leu Ser Asn Gly Asn Thr Ser Tyr Val Thr Ser Lys Leu Trp Pro
                165                 170                 175

Ile Ile Gln Asn Asp Leu Gly Tyr Val Val Ser Tyr Trp Asn Gln Ser
                180                 185                 190

Thr Tyr Asp Leu Trp Glu Glu Val Asp Ser Ser Phe Phe Thr Thr
            195                 200                 205

Ala Val Gln His Arg Ala Leu Arg Glu Gly Ala Ala Phe Ala Thr Ala
                210                 215                 220

Ile Gly Gln Thr Ser Gln Val Ser Ser Tyr Thr Thr Gln Ala Asp Asn
225                 230                 235                 240

Leu Leu Cys Phe Leu Gln Ser Tyr Trp Asn Pro Ser Gly Gly Tyr Ile
                245                 250                 255

Thr Ala Asn Thr Gly Gly Gly Arg Ser Gly Lys Asp Ala Asn Thr Leu
            260                 265                 270

Leu Ala Ser Ile His Thr Tyr Asp Pro Ser Ala Gly Cys Asp Ala Ala
                275                 280                 285

Thr Phe Gln Pro Cys Ser Asp Lys Ala Leu Ser Asn Leu Lys Val Tyr
    290                 295                 300

Val Asp Ser Phe Arg Ser Val Tyr Ser Ile Asn Ser Gly Ile Ala Ser
305                 310                 315                 320

Asn Ala Ala Val Ala Thr Gly Arg Tyr Pro Glu Asp Ser Tyr Gln Gly
                325                 330                 335

Gly Asn Pro Trp Tyr Leu Thr Thr Phe Ala Val Ala Glu Gln Leu Tyr
            340                 345                 350

Asp Ala Leu Asn Val Trp Glu Ser Gln Gly Ser Leu Glu Val Thr Ser
                355                 360                 365

Thr Ser Leu Ala Phe Phe Gln Gln Phe Ser Ser Gly Val Thr Ala Gly
    370                 375                 380

Thr Tyr Ser Ser Ser Ser Ser Thr Tyr Ser Ser Leu Thr Ser Ala Ile
385                 390                 395                 400

Lys Ser Phe Ala Asp Gly Phe Val Thr Ile Asn Ala Lys Tyr Thr Pro
                405                 410                 415
```

```
Ser Asn Gly Gly Leu Ala Glu Gln Tyr Ser Lys Ser Asp Gly Ser Pro
            420                 425                 430

Leu Ser Ala Val Asp Leu Thr Trp Ser Tyr Ala Ser Ala Leu Thr Ala
        435                 440                 445

Phe Glu Ala Arg Asn Asp Thr Gln Phe Ala Gly Trp Gly Ala Ala Gly
    450                 455                 460

Leu Thr Val Pro Ser Ser Cys Ser Gly Asn Ser Gly Gly Pro Thr Val
465                 470                 475                 480

Ala Val Thr Phe Asn Val Asn Ala Glu Thr Val Trp Gly Glu Asn Ile
                485                 490                 495

Tyr Leu Thr Gly Ser Val Asp Ala Leu Glu Asn Trp Ser Ala Asp Asn
            500                 505                 510

Ala Leu Leu Leu Ser Ser Ala Asn Tyr Pro Thr Trp Ser Ile Thr Val
        515                 520                 525

Asn Leu Pro Ala Ser Thr Ala Ile Glu Tyr Lys Tyr Ile Arg Lys Asn
    530                 535                 540

Asn Gly Ala Val Thr Trp Glu Ser Asp Pro Asn Asn Ser Ile Thr Thr
545                 550                 555                 560

Pro Ala Ser Gly Ser Thr Thr Glu Asn Asp Thr Trp Arg
                565                 570

<210> SEQ ID NO 8
<211> LENGTH: 573
<212> TYPE: PRT
<213> ORGANISM: Gloeophyllum trabeum

<400> SEQUENCE: 8

Met Tyr Arg Phe Leu Val Cys Ala Leu Gly Leu Ala Ala Thr Val Leu
1               5                   10                  15

Ala Gln Ser Val Asp Ser Tyr Val Ser Ser Glu Gly Pro Ile Ala Lys
            20                  25                  30

Ala Gly Val Leu Ala Asn Ile Gly Pro Asn Gly Ser Lys Ala Ser Gly
        35                  40                  45

Ala Ser Ala Gly Val Val Ala Ser Pro Ser Thr Ser Asp Pro Asp
    50                  55                  60

Tyr Trp Tyr Thr Trp Thr Arg Asp Ser Ser Leu Val Phe Lys Ser Leu
65                  70                  75                  80

Ile Asp Gln Tyr Thr Thr Gly Ile Asp Ser Thr Ser Ser Leu Arg Thr
                85                  90                  95

Leu Ile Asp Asp Phe Val Thr Ala Glu Ala Asn Leu Gln Gln Val Ser
            100                 105                 110

Asn Pro Ser Gly Thr Leu Thr Thr Gly Gly Leu Gly Glu Pro Lys Phe
        115                 120                 125

Asn Val Asp Glu Thr Ala Phe Thr Gly Ala Trp Gly Arg Pro Gln Arg
    130                 135                 140

Asp Gly Pro Ala Leu Arg Ser Thr Ala Leu Ile Thr Tyr Gly Asn Trp
145                 150                 155                 160

Leu Leu Ser Asn Gly Asn Thr Ser Tyr Val Thr Ser Ile Leu Trp Pro
                165                 170                 175

Ile Ile Gln Asn Asp Leu Gly Tyr Val Ser Tyr Trp Asn Gln Ser
            180                 185                 190

Thr Tyr Asp Leu Trp Glu Glu Val Asp Ser Ser Ser Phe Phe Thr Thr
        195                 200                 205

Ala Val Gln His Arg Ala Leu Arg Glu Gly Ala Ala Phe Ala Thr Ala
```

```
            210                 215                 220
Ile Gly Gln Thr Ser Gln Val Ser Ser Tyr Thr Thr Gln Ala Asp Asn
225                 230                 235                 240

Leu Leu Cys Phe Leu Gln Ser Tyr Trp Asn Pro Ser Gly Gly Tyr Ile
                245                 250                 255

Thr Ala Asn Thr Gly Gly Arg Ser Gly Lys Asp Ala Asn Thr Leu
                260                 265                 270

Leu Ala Ser Ile His Thr Tyr Asp Pro Ser Ala Gly Cys Asp Ala Ala
                275                 280                 285

Thr Phe Gln Pro Cys Ser Asp Lys Ala Leu Ser Asn Leu Lys Val Tyr
            290                 295                 300

Phe Asp Ser Phe Arg Ser Val Tyr Ser Ile Asn Ser Gly Val Ala Ser
305                 310                 315                 320

Asn Ala Ala Val Ala Thr Gly Arg Tyr Pro Glu Asp Ser Tyr Gln Gly
                325                 330                 335

Gly Asn Pro Trp Tyr Leu Thr Thr Phe Ala Val Ala Glu Gln Leu Tyr
                340                 345                 350

Asp Ala Leu Asn Val Trp Glu Ser Gln Gly Ser Leu Glu Val Thr Ser
                355                 360                 365

Thr Ser Leu Ala Phe Phe Gln Gln Phe Ser Ser Gly Val Thr Ala Gly
            370                 375                 380

Thr Tyr Ser Ser Ser Ser Ser Thr Tyr Ser Thr Leu Thr Ser Ala Ile
385                 390                 395                 400

Lys Asn Phe Ala Asp Gly Phe Val Ala Ile Asn Ala Lys Tyr Thr Pro
                405                 410                 415

Ser Asn Gly Gly Leu Ala Glu Gln Tyr Ser Lys Ser Asp Gly Ser Pro
                420                 425                 430

Leu Ser Ala Val Asp Leu Thr Trp Ser Tyr Ala Ser Ala Leu Thr Ala
            435                 440                 445

Phe Glu Ala Arg Asn Asn Thr Gln Phe Ala Gly Trp Gly Ala Ala Gly
            450                 455                 460

Leu Thr Val Pro Ser Ser Cys Ser Gly Asn Ser Gly Gly Pro Thr Val
465                 470                 475                 480

Ala Val Thr Phe Asn Val Asn Ala Glu Thr Val Trp Gly Glu Asn Ile
                485                 490                 495

Tyr Leu Thr Gly Ser Val Asp Ala Leu Glu Asn Trp Ser Ala Asp Asn
                500                 505                 510

Ala Leu Leu Leu Ser Ser Ala Asn Tyr Pro Thr Trp Ser Ile Thr Val
            515                 520                 525

Asn Leu Pro Ala Ser Thr Ala Ile Glu Tyr Lys Tyr Ile Arg Lys Asn
530                 535                 540

Asn Gly Ala Val Thr Trp Glu Ser Asp Pro Asn Asn Ser Ile Thr Thr
545                 550                 555                 560

Pro Ala Ser Gly Ser Thr Thr Glu Asn Asp Thr Trp Arg
                565                 570

<210> SEQ ID NO 9
<211> LENGTH: 573
<212> TYPE: PRT
<213> ORGANISM: Gloeophyllum sepiarium

<400> SEQUENCE: 9

Met Tyr Arg Phe Leu Val Cys Ala Leu Gly Leu Ala Ala Ser Val Leu
1               5                   10                  15
```

```
Ala Gln Ser Val Asp Ser Tyr Val Ser Ser Glu Gly Pro Ile Ala Lys
            20                  25                  30

Ala Gly Val Leu Ala Asn Ile Gly Pro Asn Gly Ser Lys Ala Ser Gly
        35                  40                  45

Ala Ser Ala Gly Val Val Ala Ser Pro Ser Thr Ser Asp Pro Asp
    50                  55                  60

Tyr Trp Tyr Thr Trp Thr Arg Asp Ser Ser Leu Val Phe Lys Ser Leu
65                  70                  75                  80

Ile Asp Gln Tyr Thr Thr Gly Ile Asp Ser Thr Ser Ser Leu Arg Thr
                85                  90                  95

Leu Ile Asp Asp Phe Val Thr Ala Glu Ala Asn Leu Gln Gln Val Ser
            100                 105                 110

Asn Pro Ser Gly Thr Leu Thr Thr Gly Gly Leu Gly Glu Pro Lys Phe
        115                 120                 125

Asn Val Asp Glu Thr Ala Phe Thr Gly Ala Trp Gly Arg Pro Gln Arg
    130                 135                 140

Asp Gly Pro Ala Leu Arg Ser Thr Ala Leu Ile Thr Tyr Gly Asn Trp
145                 150                 155                 160

Leu Leu Ser Asn Gly Asn Thr Ser Tyr Val Thr Ser Asn Leu Trp Pro
            165                 170                 175

Ile Ile Gln Asn Asp Leu Gly Tyr Val Val Ser Tyr Trp Asn Gln Ser
            180                 185                 190

Thr Tyr Asp Leu Trp Glu Glu Val Asp Ser Ser Ser Phe Phe Thr Thr
        195                 200                 205

Ala Val Gln His Arg Ala Leu Arg Glu Gly Ala Ala Phe Ala Thr Ala
    210                 215                 220

Ile Gly Gln Thr Ser Gln Val Ser Ser Tyr Thr Thr Gln Ala Asp Asn
225                 230                 235                 240

Leu Leu Cys Phe Leu Gln Ser Tyr Trp Asn Pro Ser Gly Gly Tyr Ile
            245                 250                 255

Thr Ala Asn Thr Gly Gly Gly Arg Ser Gly Lys Asp Ala Asn Thr Leu
        260                 265                 270

Leu Ala Ser Ile His Thr Tyr Asp Pro Ser Ala Gly Cys Asp Ala Ala
    275                 280                 285

Thr Phe Gln Pro Cys Ser Asp Lys Ala Leu Ser Asn Leu Lys Val Tyr
290                 295                 300

Val Asp Ser Phe Arg Ser Val Tyr Ser Ile Asn Ser Gly Ile Ala Ser
305                 310                 315                 320

Asn Ala Ala Val Ala Thr Gly Arg Tyr Pro Glu Asp Ser Tyr Gln Gly
            325                 330                 335

Gly Asn Pro Trp Tyr Leu Thr Thr Phe Ala Val Ala Glu Gln Leu Tyr
        340                 345                 350

Asp Ala Leu Asn Val Trp Glu Leu Gln Gly Ser Leu Glu Val Thr Ser
    355                 360                 365

Thr Ser Leu Ala Phe Phe Gln Gln Phe Ser Ser Gly Val Thr Ala Gly
370                 375                 380

Thr Tyr Ser Ser Ser Ser Ser Thr Tyr Ser Thr Leu Thr Ser Ala Ile
385                 390                 395                 400

Lys Ser Phe Ala Asp Gly Phe Val Ala Ile Asn Ala Lys Tyr Thr Pro
            405                 410                 415

Ser Asn Gly Gly Leu Ala Glu Gln Tyr Ser Lys Ser Asp Gly Ser Pro
        420                 425                 430

Leu Ser Ala Val Asp Leu Thr Trp Ser Tyr Ala Ser Ala Leu Thr Ala
```

```
                    435                 440                 445

Phe Glu Ala Arg Asn Asp Thr Gln Phe Ala Gly Trp Gly Ala Ala Ser
450                 455                 460

Leu Thr Val Pro Ser Ser Cys Ser Gly Asn Ser Gly Gly Pro Thr Val
465                 470                 475                 480

Ala Val Thr Phe Asn Val Asn Ala Glu Thr Val Trp Gly Glu Asn Ile
                485                 490                 495

Tyr Leu Thr Gly Ser Val Asp Ala Leu Glu Asn Trp Ser Ala Asp Asn
                500                 505                 510

Ala Leu Leu Leu Ser Ser Ala Asn Tyr Pro Thr Trp Ser Ile Thr Val
                515                 520                 525

Asn Leu Pro Ala Ser Thr Ala Ile Glu Tyr Lys Tyr Ile Arg Lys Asn
                530                 535                 540

Asn Gly Ala Val Thr Trp Glu Ser Asp Pro Asn Asn Ser Ile Thr Thr
545                 550                 555                 560

Pro Ala Ser Gly Ser Thr Thr Glu Asn Asp Thr Trp Arg
                565                 570

<210> SEQ ID NO 10
<211> LENGTH: 573
<212> TYPE: PRT
<213> ORGANISM: Gloeophyllum sepiarium

<400> SEQUENCE: 10

Met Tyr Arg Phe Leu Val Cys Ala Leu Gly Leu Ala Ala Thr Val Leu
1               5                   10                  15

Ala Gln Ser Val Asp Ser Tyr Val Ser Ser Glu Gly Pro Val Ala Lys
                20                  25                  30

Ala Gly Val Leu Ala Asn Ile Gly Pro Asn Gly Ser Lys Ala Ser Gly
            35                  40                  45

Ala Ser Ala Gly Val Val Val Ala Ser Pro Ser Thr Ser Asp Pro Asp
        50                  55                  60

Tyr Trp Tyr Thr Trp Thr Arg Asp Ser Ser Leu Val Phe Lys Ser Leu
65                  70                  75                  80

Ile Asp Gln Tyr Thr Thr Gly Ile Asp Ser Thr Ser Ser Leu Arg Thr
                85                  90                  95

Leu Ile Asp Asp Phe Val Thr Ala Glu Ala Asn Leu Gln Gln Val Ser
            100                 105                 110

Asn Pro Ser Gly Thr Leu Thr Thr Gly Gly Leu Gly Glu Pro Lys Phe
        115                 120                 125

Asn Val Asp Glu Thr Ala Phe Thr Gly Ala Trp Gly Arg Pro Gln Arg
    130                 135                 140

Asp Gly Pro Ala Leu Arg Ser Thr Ala Leu Ile Thr Tyr Gly Asn Trp
145                 150                 155                 160

Leu Leu Ser Asn Gly Asn Thr Ser Tyr Val Thr Ser Asn Leu Trp Pro
                165                 170                 175

Ile Ile Gln Asn Asp Leu Gly Tyr Val Val Ser Tyr Trp Asn Gln Ser
            180                 185                 190

Thr Tyr Asp Leu Trp Glu Glu Val Asp Ser Ser Ser Phe Phe Thr Thr
        195                 200                 205

Ala Val Gln His Arg Ala Leu Arg Glu Gly Ala Ala Phe Ala Thr Ala
    210                 215                 220

Ile Gly Gln Thr Ser Gln Val Ser Ser Tyr Thr Thr Gln Ala Asp Asn
225                 230                 235                 240
```

```
Leu Leu Cys Phe Leu Gln Ser Tyr Trp Asn Pro Ser Gly Gly Tyr Ile
                245                 250                 255

Thr Ala Asn Thr Gly Gly Gly Arg Ser Gly Lys Asp Ala Asn Thr Leu
            260                 265                 270

Leu Ala Ser Ile His Thr Tyr Asp Pro Ser Ala Gly Cys Asp Ala Ala
        275                 280                 285

Thr Phe Gln Pro Cys Ser Asp Lys Ala Leu Ser Asn Leu Lys Val Tyr
    290                 295                 300

Val Asp Ser Phe Arg Ser Ile Tyr Ser Ile Asn Ser Gly Ile Ala Ser
305                 310                 315                 320

Asn Ala Ala Val Ala Thr Gly Arg Tyr Pro Glu Asp Ser Tyr Gln Gly
                325                 330                 335

Gly Asn Pro Trp Tyr Leu Thr Thr Phe Ala Val Ala Glu Gln Leu Tyr
            340                 345                 350

Asp Ala Leu Asn Val Trp Glu Ser Gln Gly Ser Leu Glu Val Thr Ser
        355                 360                 365

Thr Ser Leu Ala Phe Phe Gln Gln Phe Ser Ser Gly Val Thr Ala Gly
    370                 375                 380

Thr Tyr Ser Ser Ser Ser Ser Thr Tyr Ser Thr Leu Thr Ser Ala Ile
385                 390                 395                 400

Lys Ser Phe Ala Asp Gly Phe Val Ala Ile Asn Ala Lys Tyr Thr Pro
                405                 410                 415

Ser Asn Gly Gly Leu Ala Glu Gln Tyr Ser Lys Ser Asp Gly Ser Pro
            420                 425                 430

Leu Ser Ala Val Asp Leu Thr Trp Ser Tyr Ala Ser Ala Leu Thr Ala
        435                 440                 445

Phe Glu Ala Arg Asn Asp Thr Gln Phe Ala Gly Trp Gly Ala Ala Gly
    450                 455                 460

Leu Thr Val Pro Ser Ser Cys Ser Gly Asn Ser Gly Gly Pro Thr Val
465                 470                 475                 480

Ala Val Thr Phe Asn Val Asn Ala Glu Thr Val Trp Gly Glu Asn Ile
                485                 490                 495

Tyr Leu Thr Gly Ser Val Asp Ala Leu Glu Asn Trp Ser Ala Asp Asn
            500                 505                 510

Ala Leu Leu Leu Ser Ser Ala Asn Tyr Pro Thr Trp Ser Ile Thr Val
        515                 520                 525

Asn Leu Pro Ala Ser Thr Ala Ile Glu Tyr Lys Tyr Ile Arg Lys Asn
    530                 535                 540

Asn Gly Ala Val Thr Trp Glu Ser Asp Pro Asn Asn Ser Ile Thr Thr
545                 550                 555                 560

Pro Ala Ser Gly Ser Thr Thr Glu Asn Asp Thr Trp Arg
                565                 570

<210> SEQ ID NO 11
<211> LENGTH: 573
<212> TYPE: PRT
<213> ORGANISM: Gloeophyllum sp

<400> SEQUENCE: 11

Met Tyr Arg Phe Leu Val Cys Ala Leu Gly Leu Ala Ala Thr Val Leu
1               5                   10                  15

Ala Gln Ser Val Asp Ser Tyr Val Ser Ser Glu Gly Pro Val Ala Lys
            20                  25                  30

Ala Gly Val Leu Ala Asn Ile Gly Pro Asn Gly Ser Lys Ala Ser Gly
        35                  40                  45
```

-continued

```
Ala Ser Ala Gly Val Val Ala Ser Pro Ser Thr Ser Asp Pro Asp
        50              55              60

Tyr Trp Tyr Thr Trp Thr Arg Asp Ser Ser Leu Val Phe Lys Ser Leu
65              70              75              80

Ile Asp Gln Tyr Thr Thr Gly Ile Asp Ser Thr Ser Ser Leu Arg Thr
                85              90              95

Leu Ile Asp Asp Phe Val Thr Ala Glu Ala Asn Leu Gln Gln Val Ser
            100             105             110

Asn Pro Ser Gly Thr Leu Thr Thr Gly Gly Leu Gly Glu Pro Lys Phe
        115             120             125

Asn Val Asp Glu Thr Ala Phe Thr Gly Ala Trp Gly Arg Pro Gln Arg
130             135             140

Asp Gly Pro Ala Leu Arg Ser Thr Ala Leu Ile Thr Tyr Gly Asn Trp
145             150             155             160

Leu Leu Ser Asn Gly Asn Thr Ser Tyr Val Thr Ser Asn Leu Trp Pro
                165             170             175

Ile Ile Gln Asn Asp Leu Gly Tyr Val Val Ser Tyr Trp Asn Gln Ser
            180             185             190

Thr Tyr Asp Leu Trp Glu Glu Val Asp Ser Ser Ser Phe Phe Thr Thr
    195             200             205

Ala Val Gln His Arg Ala Leu Arg Glu Gly Ala Ala Phe Ala Thr Ala
    210             215             220

Ile Gly Gln Thr Ser Gln Val Ser Ser Tyr Thr Thr Gln Ala Asp Asn
225             230             235             240

Leu Leu Cys Phe Leu Gln Ser Tyr Trp Asn Pro Ser Gly Gly Tyr Ile
                245             250             255

Thr Ala Asn Thr Gly Gly Gly Arg Ser Gly Lys Asp Ala Asn Thr Leu
            260             265             270

Leu Ala Ser Ile His Thr Tyr Asp Pro Ser Ala Gly Cys Asp Ala Ala
        275             280             285

Thr Phe Gln Pro Cys Ser Asp Lys Ala Leu Ser Asn Leu Lys Val Tyr
    290             295             300

Val Asp Ser Phe Arg Ser Ile Tyr Ser Ile Asn Ser Gly Ile Ala Ser
305             310             315             320

Asn Ala Ala Val Ala Thr Gly Arg Tyr Pro Glu Asp Ser Tyr Gln Gly
                325             330             335

Gly Asn Pro Trp Tyr Leu Thr Thr Phe Ala Val Ala Glu Gln Leu Tyr
            340             345             350

Asp Ala Leu Asn Val Trp Glu Ser Gln Gly Ser Leu Glu Val Thr Ser
        355             360             365

Thr Ser Leu Ala Phe Gln Gln Phe Ser Ser Gly Val Thr Ala Gly
    370             375             380

Thr Tyr Ser Ser Ser Ser Ser Thr Tyr Ser Thr Leu Thr Ser Ala Ile
385             390             395             400

Lys Ser Phe Ala Asp Gly Phe Val Ala Ile Asn Ala Lys Tyr Thr Pro
                405             410             415

Ser Asn Gly Gly Leu Ala Glu Gln Tyr Ser Lys Ser Asp Gly Ser Pro
            420             425             430

Leu Ser Ala Val Asp Leu Thr Trp Ser Tyr Ala Ser Ala Leu Thr Ala
        435             440             445

Phe Glu Ala Arg Asn Asp Thr Gln Phe Ala Gly Trp Gly Ala Ala Gly
    450             455             460
```

```
Leu Thr Val Pro Ser Ser Cys Ser Gly Asn Ser Gly Gly Pro Thr Val
465                 470                 475                 480

Ala Val Thr Phe Asn Val Asn Ala Glu Thr Val Trp Gly Glu Asn Ile
            485                 490                 495

Tyr Leu Thr Gly Ser Val Asp Ala Leu Glu Asn Trp Ser Ala Asp Asn
        500                 505                 510

Ala Leu Leu Ser Ser Val Asn Tyr Pro Thr Trp Ser Ile Thr Val
    515                 520                 525

Asn Leu Pro Ala Ser Thr Ala Ile Glu Tyr Lys Tyr Ile Arg Lys Asn
530                 535                 540

Asn Gly Ala Val Thr Trp Glu Ser Asp Pro Asn Asn Ser Ile Thr Thr
545                 550                 555                 560

Pro Ala Ser Gly Ser Thr Thr Glu Asn Asp Thr Trp Arg
                565                 570

<210> SEQ ID NO 12
<211> LENGTH: 573
<212> TYPE: PRT
<213> ORGANISM: Gloeophyllum trabeum

<400> SEQUENCE: 12

Met Tyr Arg Phe Leu Val Cys Ala Leu Gly Leu Ala Ala Ser Val Leu
1               5                   10                  15

Ala Gln Ser Val Asp Ser Tyr Val Ser Ser Glu Gly Pro Ile Ala Lys
            20                  25                  30

Ala Gly Val Leu Ala Asn Ile Gly Pro Asn Gly Ser Lys Ala Ser Gly
        35                  40                  45

Ala Ser Ala Gly Val Val Val Ala Ser Pro Ser Thr Ser Asp Pro Asp
50                  55                  60

Tyr Trp Tyr Thr Trp Thr Arg Asp Ser Ser Leu Val Phe Lys Ser Leu
65                  70                  75                  80

Ile Asp Gln Tyr Thr Thr Gly Ile Asp Gly Thr Ser Ser Leu Arg Thr
                85                  90                  95

Leu Ile Asp Asp Phe Val Thr Ala Glu Ala Asn Leu Gln Gln Val Ser
            100                 105                 110

Asn Pro Ser Gly Thr Leu Thr Thr Gly Gly Leu Gly Glu Pro Lys Phe
        115                 120                 125

Asn Val Asp Glu Thr Ala Phe Thr Gly Ala Trp Gly Arg Pro Gln Arg
    130                 135                 140

Asp Gly Pro Ala Leu Arg Ser Thr Ala Leu Ile Thr Tyr Gly Asn Trp
145                 150                 155                 160

Leu Leu Ser Asn Gly Asn Thr Ser Tyr Val Thr Ser Asn Leu Trp Pro
                165                 170                 175

Ile Ile Gln Asn Asp Leu Gly Tyr Val Val Ser Tyr Trp Asn Gln Ser
            180                 185                 190

Thr Tyr Asp Leu Trp Glu Glu Val Asp Ser Ser Ser Phe Phe Thr Thr
        195                 200                 205

Ala Val Gln His Arg Ala Leu Arg Glu Gly Ala Ala Phe Ala Thr Ala
    210                 215                 220

Ile Gly Gln Thr Ser Gln Val Ser Ser Tyr Thr Thr Gln Ala Asp Asn
225                 230                 235                 240

Leu Leu Cys Phe Leu Gln Ser Tyr Trp Asn Pro Ser Gly Gly Tyr Ile
                245                 250                 255

Thr Ala Asn Thr Gly Gly Gly Arg Ser Gly Lys Asp Ala Asn Thr Leu
            260                 265                 270
```

```
Leu Ala Ser Ile His Thr Tyr Asp Pro Ser Ala Gly Cys Asp Ala Ala
            275                 280                 285

Thr Phe Gln Pro Cys Ser Asp Lys Ala Leu Ser Asn Leu Lys Val Tyr
    290                 295                 300

Val Asp Ser Phe Arg Ser Val Tyr Ser Ile Asn Ser Gly Ile Ala Ser
305                 310                 315                 320

Asn Ala Ala Val Ala Thr Gly Arg Tyr Pro Glu Asp Ser Tyr Gln Gly
                325                 330                 335

Gly Asn Pro Trp Tyr Leu Thr Thr Phe Ala Val Ala Glu Gln Leu Tyr
            340                 345                 350

Asp Ala Leu Asn Val Trp Glu Ser Gln Gly Ser Leu Glu Val Thr Ser
        355                 360                 365

Thr Ser Leu Ala Phe Phe Gln Gln Phe Ser Ser Gly Val Thr Ala Gly
    370                 375                 380

Thr Tyr Ser Ser Ser Ser Ser Thr Tyr Ser Thr Leu Thr Ser Ala Ile
385                 390                 395                 400

Lys Ser Phe Ala Asp Gly Phe Val Ala Val Asn Ala Lys Tyr Thr Pro
                405                 410                 415

Ser Asn Gly Gly Leu Ala Glu Gln Tyr Ser Lys Ser Asp Gly Ser Pro
            420                 425                 430

Leu Ser Ala Val Asp Leu Thr Trp Ser Tyr Ala Ser Ala Leu Thr Ala
        435                 440                 445

Phe Glu Ala Arg Asn Asn Thr Gln Phe Ala Gly Trp Gly Ala Ala Gly
    450                 455                 460

Leu Thr Val Pro Ser Ser Cys Ser Gly Asn Ser Gly Gly Pro Thr Val
465                 470                 475                 480

Ala Val Thr Phe Asn Val Asn Ala Glu Thr Val Trp Gly Glu Asn Ile
                485                 490                 495

Tyr Leu Thr Gly Ser Val Asp Ala Leu Glu Asn Trp Ser Ala Asp Asn
            500                 505                 510

Ala Leu Leu Leu Ser Ser Ala Asn Tyr Pro Thr Trp Ser Ile Thr Val
        515                 520                 525

Asn Leu Pro Ala Ser Thr Ala Ile Glu Tyr Lys Tyr Ile Arg Lys Asn
    530                 535                 540

Asn Gly Ala Val Thr Trp Glu Ser Asp Pro Asn Asn Ser Ile Thr Thr
545                 550                 555                 560

Pro Ala Ser Gly Ser Thr Thr Glu Asn Asp Thr Trp Arg
                565                 570

<210> SEQ ID NO 13
<211> LENGTH: 576
<212> TYPE: PRT
<213> ORGANISM: Gloeophyllum trabeum

<400> SEQUENCE: 13

Met Tyr Arg Phe Leu Val Cys Ala Leu Gly Leu Leu Gly Thr Val Leu
1               5                   10                  15

Ala Gln Ser Val Asp Ser Tyr Val Gly Ser Glu Gly Pro Ile Ala Lys
            20                  25                  30

Ala Gly Val Leu Ala Asn Ile Gly Pro Asn Gly Ser Lys Ala Ser Gly
        35                  40                  45

Ala Ala Ala Gly Val Val Ala Ser Pro Ser Lys Ser Asp Pro Asp
    50                  55                  60

Tyr Trp Tyr Thr Trp Thr Arg Asp Ser Ser Leu Val Phe Lys Ser Leu
```

```
                65                  70                  75                  80

Ile Asp Gln Tyr Thr Thr Gly Ile Asp Ser Thr Ser Ser Leu Arg Ser
                    85                  90                  95

Leu Ile Asp Ser Phe Val Ile Ala Glu Ala Asn Ile Gln Gln Val Ser
                100                 105                 110

Asn Pro Ser Gly Thr Leu Thr Thr Gly Gly Leu Gly Glu Pro Lys Phe
                115                 120                 125

Asn Val Asp Glu Thr Ala Phe Thr Gly Ala Trp Gly Arg Pro Gln Arg
130                 135                 140

Asp Gly Pro Ala Leu Arg Ala Thr Ala Leu Ile Thr Tyr Gly Asn Trp
145                 150                 155                 160

Leu Leu Ser Asn Gly Asn Thr Thr Trp Val Thr Ser Thr Leu Trp Pro
                165                 170                 175

Ile Ile Gln Asn Asp Leu Asn Tyr Val Val Gln Tyr Trp Asn Gln Thr
                180                 185                 190

Thr Phe Asp Leu Trp Glu Glu Val Asn Ser Ser Phe Phe Thr Thr
                195                 200                 205

Ala Val Gln His Arg Ala Leu Arg Glu Gly Ala Ala Phe Ala Thr Lys
                210                 215                 220

Ile Gly Gln Thr Ser Ser Val Ser Ser Tyr Thr Thr Gln Ala Ala Asn
225                 230                 235                 240

Leu Leu Cys Phe Leu Gln Ser Tyr Trp Asn Pro Thr Ser Gly Tyr Ile
                245                 250                 255

Thr Ala Asn Thr Gly Gly Gly Arg Ser Gly Lys Asp Ala Asn Thr Leu
                260                 265                 270

Leu Ala Ser Ile His Thr Tyr Asp Pro Ser Ala Gly Cys Asp Ala Thr
                275                 280                 285

Thr Phe Gln Pro Cys Ser Asp Lys Ala Leu Ser Asn Leu Lys Val Tyr
                290                 295                 300

Val Asp Ser Phe Arg Ser Val Tyr Ser Ile Asn Ser Gly Ile Ala Ser
305                 310                 315                 320

Asn Ala Ala Val Ala Thr Gly Arg Tyr Pro Glu Asp Ser Tyr Gln Gly
                325                 330                 335

Gly Asn Pro Trp Tyr Leu Thr Thr Phe Ala Val Ala Glu Gln Leu Tyr
                340                 345                 350

Asp Ala Leu Asn Val Trp Ala Ala Gln Gly Ser Leu Asn Val Thr Ser
                355                 360                 365

Ile Ser Leu Pro Phe Phe Gln Gln Phe Ser Ser Val Thr Ala Gly
                370                 375                 380

Thr Tyr Ala Ser Ser Ser Thr Thr Tyr Thr Thr Leu Thr Ser Ala Ile
385                 390                 395                 400

Lys Ser Phe Ala Asp Gly Phe Val Ala Ile Asn Ala Gln Tyr Thr Pro
                405                 410                 415

Ser Asn Gly Gly Leu Ala Glu Gln Phe Ser Arg Ser Asn Gly Ser Pro
                420                 425                 430

Val Ser Ala Val Asp Leu Thr Trp Ser Tyr Ala Ser Ala Leu Thr Ala
                435                 440                 445

Phe Glu Ala Arg Asn Asn Thr Gln Phe Ala Gly Trp Gly Ala Val Gly
                450                 455                 460

Leu Thr Val Pro Thr Ser Cys Ser Ser Asn Ser Gly Gly Gly Gly
465                 470                 475                 480

Ser Thr Val Ala Val Thr Phe Asn Val Asn Ala Gln Thr Val Trp Gly
                485                 490                 495
```

```
Glu Asn Ile Tyr Ile Thr Gly Ser Val Asp Ala Leu Ser Asn Trp Ser
            500                 505                 510

Pro Asp Asn Ala Leu Leu Ser Ser Ala Asn Tyr Pro Thr Trp Ser
            515                 520                 525

Ile Thr Val Asn Leu Pro Ala Ser Thr Ala Ile Gln Tyr Lys Tyr Ile
            530                 535                 540

Arg Lys Asn Asn Gly Ala Val Thr Trp Glu Ser Asp Pro Asn Ser
545                 550                 555                 560

Ile Thr Thr Pro Ala Ser Gly Ser Val Thr Glu Asn Asp Thr Trp Arg
                565                 570                 575
```

<210> SEQ ID NO 14
<211> LENGTH: 576
<212> TYPE: PRT
<213> ORGANISM: Gloeophyllum trabeum

<400> SEQUENCE: 14

```
Met Tyr Arg Phe Leu Val Cys Ala Leu Gly Leu Gly Thr Val Leu
1               5                   10                  15

Ala Gln Ser Val Asp Ser Tyr Val Gly Ser Glu Gly Pro Ile Ala Lys
            20                  25                  30

Ala Gly Val Leu Ala Asn Ile Gly Pro Asn Gly Ser Lys Ala Ser Gly
        35                  40                  45

Ala Ala Gly Val Val Ala Ser Pro Ser Lys Ser Asp Pro Asp
    50                  55                  60

Tyr Trp Tyr Thr Trp Thr Arg Asp Ser Ser Leu Val Phe Lys Ser Leu
65                  70                  75                  80

Ile Asp Gln Tyr Thr Thr Gly Ile Asp Ser Thr Ser Ser Leu Arg Ser
                85                  90                  95

Leu Ile Asp Ser Phe Val Ile Ala Glu Ala Asn Ile Gln Gln Val Ser
            100                 105                 110

Asn Pro Ser Gly Thr Leu Thr Thr Gly Gly Leu Gly Glu Pro Lys Phe
        115                 120                 125

Asn Val Asp Glu Thr Ala Phe Thr Gly Ala Trp Gly Arg Pro Gln Arg
    130                 135                 140

Asp Gly Pro Ala Leu Arg Ala Thr Ala Leu Ile Thr Tyr Gly Asn Trp
145                 150                 155                 160

Leu Leu Ser Asn Gly Asn Thr Thr Trp Val Thr Ser Thr Leu Trp Pro
                165                 170                 175

Ile Ile Gln Asn Asp Leu Asn Tyr Val Val Gln Tyr Trp Asn Gln Thr
            180                 185                 190

Thr Phe Asp Leu Trp Glu Glu Val Asn Ser Ser Phe Phe Thr Thr
        195                 200                 205

Ala Val Gln His Arg Ala Leu Arg Glu Gly Ala Ala Phe Ala Thr Lys
    210                 215                 220

Ile Gly Gln Thr Ser Ser Val Ser Ser Tyr Thr Thr Gln Ala Ala Asn
225                 230                 235                 240

Leu Leu Cys Phe Leu Gln Ser Tyr Trp Asn Pro Thr Ser Gly Tyr Ile
                245                 250                 255

Thr Ala Asn Thr Gly Gly Gly Arg Ser Gly Lys Asp Ala Asn Thr Leu
            260                 265                 270

Leu Ala Ser Ile His Thr Tyr Asp Pro Ser Ala Gly Cys Asp Ala Thr
        275                 280                 285

Thr Phe Gln Pro Cys Ser Asp Lys Ala Leu Ser Asn Leu Lys Val Tyr
```

```
            290                 295                 300
Val Asp Ser Phe Arg Ser Val Tyr Ser Ile Asn Ser Gly Ile Ala Ser
305                 310                 315                 320

Asn Ala Ala Val Ala Thr Gly Arg Tyr Pro Glu Asp Ser Tyr Gln Gly
                325                 330                 335

Gly Asn Pro Trp Tyr Leu Thr Thr Phe Ala Val Ala Glu Gln Leu Tyr
            340                 345                 350

Asp Ala Leu Asn Val Trp Ala Ala Gln Gly Ser Leu Asn Val Thr Ser
            355                 360                 365

Ile Ser Leu Pro Phe Phe Gln Gln Phe Ser Ser Val Thr Ala Gly
            370                 375                 380

Thr Tyr Ala Ser Ser Ser Thr Thr Tyr Thr Thr Leu Thr Ser Ala Ile
385                 390                 395                 400

Lys Ser Phe Ala Asp Gly Phe Val Ala Ile Asn Ala Gln Tyr Thr Pro
                405                 410                 415

Ser Asn Gly Gly Leu Ala Glu Gln Phe Ser Arg Ser Asn Gly Ala Pro
            420                 425                 430

Val Ser Ala Val Asp Leu Thr Trp Ser Tyr Ala Ser Ala Leu Thr Ala
            435                 440                 445

Phe Glu Ala Arg Asn Asn Thr Gln Phe Ala Gly Trp Gly Ala Val Gly
            450                 455                 460

Leu Thr Val Pro Thr Ser Cys Ser Ser Asn Ser Gly Gly Gly Gly
465                 470                 475                 480

Ser Thr Val Ala Val Thr Phe Asn Val Asn Ala Gln Thr Val Trp Gly
                485                 490                 495

Glu Asn Ile Tyr Ile Thr Gly Ser Val Asp Ala Leu Ser Asn Trp Ser
            500                 505                 510

Pro Asp Asn Ala Leu Leu Leu Ser Ser Ala Asn Tyr Pro Thr Trp Ser
            515                 520                 525

Ile Thr Val Asn Leu Pro Ala Ser Thr Ala Ile Gln Tyr Lys Tyr Ile
            530                 535                 540

Arg Lys Asn Asn Gly Ala Val Thr Trp Glu Ser Asp Pro Asn Asn Ser
545                 550                 555                 560

Ile Thr Thr Pro Ala Ser Gly Ser Val Thr Glu Asn Asp Thr Trp Arg
                565                 570                 575

<210> SEQ ID NO 15
<211> LENGTH: 618
<212> TYPE: PRT
<213> ORGANISM: Talaromyces emersonii

<400> SEQUENCE: 15

Met Ala Ser Leu Val Ala Gly Ala Leu Cys Ile Leu Gly Leu Thr Pro
1               5                   10                  15

Ala Ala Phe Ala Arg Ala Pro Val Ala Ala Arg Ala Thr Gly Ser Leu
                20                  25                  30

Asp Ser Phe Leu Ala Thr Glu Thr Pro Ile Ala Leu Gln Gly Val Leu
            35                  40                  45

Asn Asn Ile Gly Pro Asn Gly Ala Asp Val Ala Gly Ala Ser Ala Gly
        50                  55                  60

Ile Val Val Ala Ser Pro Ser Arg Ser Asp Pro Asn Tyr Phe Tyr Ser
65                  70                  75                  80

Trp Thr Arg Asp Ala Ala Leu Thr Ala Lys Tyr Leu Val Asp Ala Phe
                85                  90                  95
```

-continued

```
Ile Ala Gly Asn Lys Asp Leu Glu Gln Thr Ile Gln Gln Tyr Ile Ser
                100                 105                 110
Ala Gln Ala Lys Val Gln Thr Ile Ser Asn Pro Ser Gly Asp Leu Ser
            115                 120                 125
Thr Gly Gly Leu Gly Glu Pro Lys Phe Asn Val Asn Glu Thr Ala Phe
        130                 135                 140
Thr Gly Pro Trp Gly Arg Pro Gln Arg Asp Gly Pro Ala Leu Arg Ala
145                 150                 155                 160
Thr Ala Leu Ile Ala Tyr Ala Asn Tyr Leu Ile Asp Asn Gly Glu Ala
                165                 170                 175
Ser Thr Ala Asp Glu Ile Ile Trp Pro Ile Val Gln Asn Asp Leu Ser
            180                 185                 190
Tyr Ile Thr Gln Tyr Trp Asn Ser Ser Thr Phe Asp Leu Trp Glu Glu
        195                 200                 205
Val Glu Gly Ser Ser Phe Phe Thr Ala Val Gln His Arg Ala Leu
210                 215                 220
Val Glu Gly Asn Ala Leu Ala Thr Arg Leu Asn His Thr Cys Ser Asn
225                 230                 235                 240
Cys Val Ser Gln Ala Pro Gln Val Leu Cys Phe Leu Gln Ser Tyr Trp
                245                 250                 255
Thr Gly Ser Tyr Val Leu Ala Asn Phe Gly Gly Ser Gly Arg Ser Gly
            260                 265                 270
Lys Asp Val Asn Ser Ile Leu Gly Ser Ile His Thr Phe Asp Pro Ala
        275                 280                 285
Gly Gly Cys Asp Asp Ser Thr Phe Gln Pro Cys Ser Ala Arg Ala Leu
        290                 295                 300
Ala Asn His Lys Val Val Thr Asp Ser Phe Arg Ser Ile Tyr Ala Ile
305                 310                 315                 320
Asn Ser Gly Ile Ala Glu Gly Ser Ala Val Ala Val Gly Arg Tyr Pro
                325                 330                 335
Glu Asp Val Tyr Gln Gly Gly Asn Pro Trp Tyr Leu Ala Thr Ala Ala
            340                 345                 350
Ala Ala Glu Gln Leu Tyr Asp Ala Ile Tyr Gln Trp Lys Lys Ile Gly
        355                 360                 365
Ser Ile Ser Ile Thr Asp Val Ser Leu Pro Phe Phe Gln Asp Ile Tyr
370                 375                 380
Pro Ser Ala Ala Val Gly Thr Tyr Asn Ser Gly Ser Thr Thr Phe Asn
385                 390                 395                 400
Asp Ile Ile Ser Ala Val Gln Thr Tyr Gly Asp Gly Tyr Leu Ser Ile
                405                 410                 415
Val Glu Lys Tyr Thr Pro Ser Asp Gly Ser Leu Thr Glu Gln Phe Ser
            420                 425                 430
Arg Thr Asp Gly Thr Pro Leu Ser Ala Ser Ala Leu Thr Trp Ser Tyr
        435                 440                 445
Ala Ser Leu Leu Thr Ala Ser Ala Arg Arg Gln Ser Val Val Pro Ala
        450                 455                 460
Ser Trp Gly Glu Ser Ser Ala Ser Ser Val Pro Ala Val Cys Ser Ala
465                 470                 475                 480
Thr Ser Ala Thr Gly Pro Tyr Ser Thr Ala Thr Asn Thr Val Trp Pro
                485                 490                 495
Ser Ser Gly Ser Gly Ser Ser Thr Thr Ser Ser Ala Pro Cys Thr
            500                 505                 510
Thr Pro Thr Ser Val Ala Val Thr Phe Asp Glu Ile Val Ser Thr Ser
```

```
                515                 520                 525

Tyr Gly Glu Thr Ile Tyr Leu Ala Gly Ser Ile Pro Glu Leu Gly Asn
            530                 535                 540

Trp Ser Thr Ala Ser Ala Ile Pro Leu Arg Ala Asp Ala Tyr Thr Asn
545                 550                 555                 560

Ser Asn Pro Leu Trp Tyr Val Thr Val Asn Leu Pro Pro Gly Thr Ser
                565                 570                 575

Phe Glu Tyr Lys Phe Lys Asn Gln Thr Asp Gly Thr Ile Val Trp
            580                 585                 590

Glu Asp Asp Pro Asn Arg Ser Tyr Thr Val Pro Ala Tyr Cys Gly Gln
                595                 600                 605

Thr Thr Ala Ile Leu Asp Asp Ser Trp Gln
            610                 615

<210> SEQ ID NO 16
<211> LENGTH: 828
<212> TYPE: PRT
<213> ORGANISM: Artificial sequence
<220> FEATURE:
<223> OTHER INFORMATION: Hybrid pullulanase

<400> SEQUENCE: 16

Asp Ser Thr Ser Thr Glu Val Ile Val His Tyr His Arg Phe Asp Ser
1               5                   10                  15

Asn Tyr Ala Asn Trp Asp Leu Trp Met Trp Pro Tyr Gln Pro Val Asn
                20                  25                  30

Gly Asn Gly Ala Ala Tyr Glu Phe Ser Gly Lys Asp Asp Phe Gly Val
            35                  40                  45

Lys Ala Asp Val Gln Val Pro Gly Asp Thr Gln Val Gly Leu Ile
50                  55                  60

Val Arg Thr Asn Asp Trp Ser Gln Lys Asn Thr Ser Asp Asp Leu His
65              70                  75                  80

Ile Asp Leu Thr Lys Gly His Glu Ile Trp Ile Val Gln Gly Asp Pro
                85                  90                  95

Asn Ile Tyr Tyr Asn Leu Ser Asp Ala Gln Ala Ala Thr Pro Lys
            100                 105                 110

Val Ser Asn Ala Tyr Leu Asp Asn Glu Lys Thr Val Leu Ala Lys Leu
            115                 120                 125

Thr Asn Pro Met Thr Leu Ser Asp Gly Ser Ser Gly Phe Thr Val Thr
            130                 135                 140

Asp Lys Thr Thr Gly Glu Gln Ile Pro Val Thr Ala Ala Thr Asn Ala
145                 150                 155                 160

Asn Ser Ala Ser Ser Glu Gln Thr Asp Leu Val Gln Leu Thr Leu
                165                 170                 175

Ala Ser Ala Pro Asp Val Ser His Thr Ile Gln Val Gly Ala Ala Gly
            180                 185                 190

Tyr Glu Ala Val Asn Leu Ile Pro Arg Asn Val Leu Asp Ser Ser Gln
            195                 200                 205

Tyr Tyr Tyr Ser Gly Asp Asp Leu Gly Asn Thr Tyr Thr His Lys Ala
            210                 215                 220

Thr Thr Phe Lys Val Trp Ala Pro Thr Ser Gln Val Asn Val Leu
225                 230                 235                 240

Leu Tyr Asn Ser Ala Thr Gly Ser Val Thr Lys Thr Val Pro Met Thr
                245                 250                 255

Ala Ser Gly His Gly Val Trp Glu Ala Thr Val Asn Gln Asn Leu Glu
```

-continued

Asn Trp Tyr Tyr Met Tyr Glu Val Thr Gly Gln Gly Ser Thr Arg Thr
260                 265                 270
Ala Val Asp Pro Tyr Ala Thr Ala Ile Ala Pro Asn Gly Thr Arg Gly
    275                 280                 285
Met Ile Val Asp Leu Ala Lys Thr Asp Pro Ala Gly Trp Asn Ser Asp
290                 295                 300
Lys His Ile Thr Pro Lys Asn Ile Glu Asp Glu Val Ile Tyr Glu Met
305                 310                 315                 320
Asp Val Arg Asp Phe Ser Ile Asp Pro Asn Ser Gly Met Lys Asn Lys
        325                 330                 335
Gly Lys Tyr Leu Ala Leu Thr Glu Lys Gly Thr Lys Gly Pro Asp Gly
            340                 345                 350
Val Lys Thr Gly Ile Asp Ser Leu Lys Gln Leu Gly Ile Thr His Val
    355                 360                 365
Gln Leu Met Pro Val Phe Ala Phe Ala Ser Val Asp Glu Thr Asp Pro
370                 375                 380
Thr Gln Asp Asn Trp Gly Tyr Asp Pro Arg Asn Tyr Asp Val Pro Glu
385                 390                 395                 400
Gly Gln Tyr Ala Thr Asn Ala Asn Gly Thr Ala Arg Ile Lys Glu Phe
        405                 410                 415
Lys Glu Met Val Leu Ser Leu His Arg Glu His Ile Gly Val Asn Met
            420                 425                 430
Asp Val Val Tyr Asn His Thr Phe Ala Thr Gln Ile Ser Asp Phe Asp
    435                 440                 445
Lys Ile Val Pro Glu Tyr Tyr Arg Thr Asp Ala Gly Asn Tyr
450                 455                 460
Thr Asn Gly Ser Gly Thr Gly Asn Glu Ile Ala Ser Glu Arg Pro Met
465                 470                 475                 480
Val Gln Lys Phe Ile Ile Asp Ser Leu Lys Tyr Trp Val Asn Glu Tyr
        485                 490                 495
His Ile Asp Gly Phe Arg Phe Asp Leu Met Ala Leu Leu Gly Lys Asp
            500                 505                 510
Thr Met Ser Lys Ala Ala Ser Glu Leu His Ala Ile Asn Pro Gly Ile
    515                 520                 525
Ala Leu Tyr Gly Glu Pro Trp Thr Gly Gly Thr Ser Ala Leu Pro Glu
530                 535                 540
Asp Gln Leu Leu Thr Lys Gly Ala Gln Lys Gly Met Gly Val Ala Val
545                 550                 555                 560
Phe Asn Asp Asn Leu Arg Asn Ala Leu Asp Gly Asn Val Phe Asp Ser
        565                 570                 575
Ser Ala Gln Gly Phe Ala Thr Gly Ala Thr Gly Leu Thr Asp Ala Ile
            580                 585                 590
Lys Asn Gly Val Glu Gly Ser Ile Asn Asp Phe Thr Ser Ser Pro Gly
    595                 600                 605
Glu Thr Ile Asn Tyr Val Thr Ser His Asp Asn Tyr Thr Leu Trp Asp
610                 615                 620
Lys Ile Ala Leu Ser Asn Pro Asn Asp Ser Glu Ala Asp Arg Ile Lys
625                 630                 635                 640
Met Asp Glu Leu Ala Gln Ala Val Val Met Thr Ser Gln Gly Val Pro
        645                 650                 655
Phe Met Gln Gly Gly Glu Glu Met Leu Arg Thr Lys Gly Gly Asn Asp
            660                 665                 670

-continued

```
Asn Ser Tyr Asn Ala Gly Asp Thr Val Asn Glu Phe Asp Trp Ser Arg
    690                 695                 700

Lys Ala Gln Tyr Pro Asp Val Phe Asn Tyr Tyr Ser Gly Leu Ile His
705                 710                 715                 720

Leu Arg Leu Asp His Pro Ala Phe Arg Met Thr Thr Ala Asn Glu Ile
                725                 730                 735

Asn Ser His Leu Gln Phe Leu Asn Ser Pro Glu Asn Thr Val Ala Tyr
            740                 745                 750

Glu Leu Thr Asp His Val Asn Lys Asp Lys Trp Gly Asn Ile Ile Val
        755                 760                 765

Val Tyr Asn Pro Asn Lys Thr Ala Ala Thr Ile Asn Leu Pro Ser Gly
770                 775                 780

Lys Trp Ala Ile Asn Ala Thr Ser Gly Lys Val Gly Glu Ser Thr Leu
785                 790                 795                 800

Gly Gln Ala Glu Gly Ser Val Gln Val Pro Gly Ile Ser Met Met Ile
                805                 810                 815

Leu His Gln Glu Val Ser Pro Asp His Gly Lys Lys
            820                 825

<210> SEQ ID NO 17
<211> LENGTH: 928
<212> TYPE: PRT
<213> ORGANISM: Artificial sequence
<220> FEATURE:
<223> OTHER INFORMATION: hybrid pullulanase

<400> SEQUENCE: 17

Ala Ser Ser Thr Glu Val Ile Val His Tyr His Arg Phe Asp Ala Asn
1               5                   10                  15

Tyr Ala Asn Trp Asp Leu Trp Met Trp Pro Tyr Gln Pro Val Asn Gly
            20                  25                  30

Asn Gly Ala Ala Tyr Glu Phe Ser Gly Thr Asp Glu Phe Gly Val Thr
        35                  40                  45

Ala Asp Val Gln Val Pro Gly Asp Asn Thr Gln Val Gly Leu Ile Val
50                  55                  60

Arg Lys Asn Asp Trp Ser Gln Lys Asn Thr Pro Asp Asp Leu His Ile
65                  70                  75                  80

Asp Leu Ser Lys Gly His Glu Val Trp Ile Asn Gln Gly Asp Pro Thr
                85                  90                  95

Ile Tyr Tyr Asn Leu Asn Asp Ala Glu Ala Ala Val Pro Ala Val
            100                 105                 110

Ser Asn Ala Tyr Leu Asp Asn Glu Lys Thr Val Leu Ala Lys Leu Ser
        115                 120                 125

Ser Pro Met Thr Leu Thr Asp Gly Ala Ser Gly Phe Thr Val Thr Asp
    130                 135                 140

Glu Thr Thr Gly Glu Gln Ile Pro Val Val Ser Ala Glu Ser Ala Asn
145                 150                 155                 160

Pro Val Thr Ala Val Leu Val Gly Asp Phe Gln Gln Ala Leu Gly Ala
                165                 170                 175

Ser Gly Asn Trp Ser Pro Asp Asp His Thr Lys Leu Ser Lys Ile
        180                 185                 190

Asn Ser Asn Leu Tyr Gln Phe Thr Gly Thr Leu Pro Ala Gly Thr Tyr
    195                 200                 205

Gln Tyr Lys Val Ala Leu Asp His Ser Trp Ser Ala Ser Tyr Pro Asn
210                 215                 220
```

```
Asn Asn Val Asn Leu Thr Val Pro Ala Gly Gly Thr Lys Val Thr Phe
225                 230                 235                 240

Thr Tyr Ile Pro Ser Thr His Gln Val Phe Asp Ser Ile Asn Asn Pro
            245                 250                 255

Asp Gln Thr Phe Pro Ser Ser Ala Gly Thr Gln Ser Asp Leu Val
        260                 265                 270

Gln Leu Thr Leu Ala Ser Ala Pro Asp Ile Thr His Asp Leu Gln Val
        275                 280                 285

Val Ala Asp Gly Tyr Lys Gly Lys Ile Leu Pro Arg Asn Val Leu
    290                 295                 300

Asn Leu Pro Arg Tyr Tyr Tyr Ser Gly Asn Asp Leu Gly Asn Val Tyr
305                 310                 315                 320

Ser Asn Lys Ala Thr Ala Phe Arg Val Trp Ala Pro Thr Ala Ser Asp
                325                 330                 335

Val Gln Leu Leu Leu Tyr Asn Ser Glu Thr Gly Pro Val Thr Lys Gln
            340                 345                 350

Leu Glu Met Gln Lys Ser Asp Asn Gly Thr Trp Lys Leu Lys Val Pro
            355                 360                 365

Gly Asn Leu Lys Asn Trp Tyr Tyr Leu Tyr Gln Val Thr Val Asn Gly
370                 375                 380

Lys Thr Gln Thr Ala Val Asp Pro Tyr Val Arg Ala Ile Ser Val Asn
385                 390                 395                 400

Ala Thr Arg Gly Met Ile Val Asp Leu Glu Asp Thr Asn Pro Pro Gly
                405                 410                 415

Trp Lys Glu Asp His Gln Gln Thr Pro Ala Asn Pro Val Asp Glu Val
            420                 425                 430

Ile Tyr Glu Val His Val Arg Asp Phe Ser Ile Asp Ala Asn Ser Gly
            435                 440                 445

Met Lys Asn Lys Gly Lys Tyr Leu Ala Phe Thr Glu His Gly Thr Lys
    450                 455                 460

Gly Pro Asp Gly Val Lys Thr Gly Ile Asp Ser Leu Lys Glu Leu Gly
465                 470                 475                 480

Ile Asn Ala Val Gln Leu Gln Pro Ile Glu Glu Phe Ala Ser Ile Asp
                485                 490                 495

Glu Thr Gln Pro Asn Met Tyr Asn Trp Gly Tyr Asp Pro Arg Asn Tyr
            500                 505                 510

Asn Val Pro Glu Gly Ala Tyr Ala Thr Thr Pro Glu Gly Thr Ala Arg
            515                 520                 525

Ile Thr Glu Phe Lys Gln Leu Ile Gln Ser Ile His Lys Asp Arg Ile
        530                 535                 540

Ala Ile Asn Met Asp Val Val Tyr Asn His Thr Phe Ser Thr Leu Ile
545                 550                 555                 560

Ser Asp Phe Asp Lys Ile Val Pro Gln Tyr Tyr Tyr Arg Thr Asp Asp
                565                 570                 575

Ala Gly Asn Tyr Thr Asn Gly Ser Gly Val Gly Asn Glu Phe Ala Thr
            580                 585                 590

Glu His Pro Met Ala Arg Lys Phe Val Leu Asp Ser Leu Lys Tyr Trp
        595                 600                 605

Val Thr Gln Tyr His Ile Asp Gly Phe Arg Phe Asp Leu Met Ala Leu
    610                 615                 620

Leu Gly Lys Asn Thr Met Ala Glu Ala Ser Lys Glu Leu His Ala Ile
625                 630                 635                 640
```

```
Asn Pro Gly Ile Val Leu Tyr Gly Glu Pro Trp Thr Gly Gly Thr Ser
                645                 650                 655
Gly Ile Thr Gly Asp Gln Leu Leu Thr Lys Gly Val Gln Lys Gly Leu
            660                 665                 670
Gly Ile Gly Val Phe Asn Asp Asn Leu Arg Asn Ala Leu Asp Gly Asn
            675                 680                 685
Val Phe Asp Ser Ser Ala Gln Gly Phe Ala Thr Gly Ala Thr Gly Leu
        690                 695                 700
Thr Asp Ala Ile Lys Arg Gly Val Glu Gly Ser Ile Asn Asp Phe Thr
705                 710                 715                 720
Ser Ser Pro Ser Glu Thr Ile Asn Tyr Val Ser Cys His Asp Asn Tyr
                725                 730                 735
Thr Leu Trp Asp Lys Ile Ala Leu Ser Asn Pro Asn Asp Ser Glu Ala
            740                 745                 750
Asp Arg Ile Lys Met Asp Glu Leu Ala Gln Ala Val Val Met Thr Ser
            755                 760                 765
Gln Gly Val Pro Phe Met Gln Gly Gly Glu Glu Met Leu Arg Thr Lys
        770                 775                 780
Gly Gly Asn Asp Asn Ser Tyr Asn Ala Gly Asp Thr Val Asn Glu Phe
785                 790                 795                 800
Asp Trp Ser Arg Lys Ala Gln Tyr Pro Asp Val Phe Asn Tyr Tyr Ser
                805                 810                 815
Gly Leu Ile His Leu Arg Leu Asp His Pro Ala Phe Arg Met Thr Thr
            820                 825                 830
Ala Asn Glu Ile Asn Ser His Leu Gln Phe Leu Asn Ser Pro Glu Asn
            835                 840                 845
Thr Val Ala Tyr Glu Leu Thr Asp His Val Asn Lys Asp Lys Trp Gly
        850                 855                 860
Asn Ile Ile Val Val Tyr Asn Pro Asn Lys Thr Ala Ala Thr Ile Asn
865                 870                 875                 880
Leu Pro Ser Gly Lys Trp Ala Ile Asn Ala Thr Ser Gly Lys Val Gly
                885                 890                 895
Glu Ser Thr Leu Gly Gln Ala Glu Gly Ser Val Gln Val Pro Gly Ile
            900                 905                 910
Ser Met Met Ile Leu His Gln Glu Val Ser Pro Asp His Gly Lys Lys
            915                 920                 925

<210> SEQ ID NO 18
<211> LENGTH: 928
<212> TYPE: PRT
<213> ORGANISM: Artificial sequence
<220> FEATURE:
<223> OTHER INFORMATION: Hybrid pullulanase

<400> SEQUENCE: 18

Ala Ser Ser Thr Glu Val Ile Val His Tyr His Arg Phe Asp Ala Asn
1               5                   10                  15
Tyr Ala Asn Trp Asp Leu Trp Met Trp Pro Tyr Gln Pro Val Asn Gly
            20                  25                  30
Asn Gly Ala Ala Tyr Glu Phe Ser Gly Thr Asp Glu Phe Gly Val Thr
        35                  40                  45
Ala Asp Val Gln Val Pro Gly Asp Asn Thr Gln Val Gly Leu Ile Val
    50                  55                  60
Arg Lys Asn Asp Trp Ser Gln Lys Asn Thr Pro Asp Asp Leu His Ile
65                  70                  75                  80
```

Asp Leu Ser Lys Gly His Glu Val Trp Ile Asn Gln Gly Asp Pro Thr
                85                  90                  95

Ile Tyr Tyr Asn Leu Asn Asp Ala Glu Ala Ala Val Pro Ala Val
            100                 105                 110

Ser Asn Ala Tyr Leu Asp Asn Glu Lys Thr Val Leu Ala Lys Leu Ser
            115                 120                 125

Ser Pro Met Thr Leu Thr Asp Gly Ala Ser Gly Phe Thr Val Thr Asp
            130                 135                 140

Glu Thr Thr Gly Glu Gln Ile Pro Val Val Ser Ala Glu Ser Ala Asn
145                 150                 155                 160

Pro Val Thr Ala Val Leu Val Gly Asp Phe Gln Gln Ala Leu Gly Ala
                165                 170                 175

Ser Gly Asn Trp Ser Pro Asp Asp His Thr Lys Leu Ser Lys Ile
            180                 185                 190

Asn Ser Asn Leu Tyr Gln Phe Thr Gly Thr Leu Pro Ala Gly Thr Tyr
            195                 200                 205

Gln Tyr Lys Val Ala Leu Asp His Ser Trp Ser Ala Ser Tyr Pro Asn
            210                 215                 220

Asn Asn Val Asn Leu Thr Val Pro Ala Gly Gly Thr Lys Val Thr Phe
225                 230                 235                 240

Thr Tyr Ile Pro Ser Thr His Gln Val Phe Asp Ser Ile Asn Asn Pro
                245                 250                 255

Asp Gln Thr Phe Pro Ser Ser Ser Ala Gly Thr Gln Ser Asp Leu Val
                260                 265                 270

Gln Leu Thr Leu Ala Ser Ala Pro Asp Ile Thr His Asp Leu Gln Val
            275                 280                 285

Val Ala Asp Gly Tyr Lys Gly Gly Lys Ile Leu Pro Arg Asn Val Leu
            290                 295                 300

Asn Leu Pro Arg Tyr Tyr Ser Gly Asn Asp Leu Gly Asn Val Tyr
305                 310                 315                 320

Ser Asn Lys Ala Thr Ala Phe Arg Val Trp Ala Pro Thr Ala Ser Asp
                325                 330                 335

Val Gln Leu Leu Leu Tyr Asn Ser Glu Thr Gly Pro Val Thr Lys Gln
            340                 345                 350

Leu Glu Met Gln Lys Ser Asp Asn Gly Thr Trp Lys Leu Lys Val Pro
            355                 360                 365

Gly Asn Leu Lys Asn Trp Tyr Tyr Leu Tyr Gln Val Thr Val Asn Gly
            370                 375                 380

Lys Thr Gln Thr Ala Val Asp Pro Tyr Val Arg Ala Ile Ser Val Asn
385                 390                 395                 400

Ala Thr Arg Gly Met Ile Val Asp Leu Glu Asp Thr Asn Pro Pro Gly
                405                 410                 415

Trp Lys Glu Asp His Gln Gln Thr Pro Ala Asn Pro Val Asp Glu Val
            420                 425                 430

Ile Tyr Glu Val His Val Arg Asp Phe Ser Ile Asp Ala Asn Ser Gly
            435                 440                 445

Met Lys Asn Lys Gly Lys Tyr Leu Ala Phe Thr Glu His Gly Thr Lys
450                 455                 460

Gly Pro Asp Gly Val Lys Thr Gly Ile Asp Ser Leu Lys Glu Leu Gly
465                 470                 475                 480

Ile Asn Ala Val Gln Leu Gln Pro Ile Glu Glu Phe Ala Ser Ile Asp
                485                 490                 495

Glu Thr Gln Pro Asn Met Tyr Asn Trp Gly Tyr Asp Pro Arg Asn Tyr

```
            500                 505                 510
Asn Val Pro Glu Gly Ala Tyr Ala Thr Thr Pro Glu Gly Thr Ala Arg
            515                 520                 525

Ile Thr Glu Phe Lys Gln Leu Ile Gln Ser Ile His Lys Asp Arg Ile
            530                 535                 540

Ala Ile Asn Met Asp Val Val Tyr Asn His Thr Phe Ala Thr Gln Ile
545                 550                 555                 560

Ser Asp Phe Asp Lys Ile Val Pro Glu Tyr Tyr Arg Thr Asp
            565                 570                 575

Ala Gly Asn Tyr Thr Asn Gly Ser Gly Thr Gly Asn Glu Ile Ala Ala
            580                 585                 590

Glu Arg Pro Met Val Gln Lys Phe Ile Ile Asp Ser Leu Lys Tyr Trp
            595                 600                 605

Val Asn Glu Tyr His Ile Asp Gly Phe Arg Phe Asp Leu Met Ala Leu
            610                 615                 620

Leu Gly Lys Asp Thr Met Ser Lys Ala Ala Ser Glu Leu His Ala Ile
625                 630                 635                 640

Asn Pro Gly Ile Ala Leu Tyr Gly Glu Pro Trp Thr Gly Gly Thr Ser
            645                 650                 655

Ala Leu Pro Glu Asp Gln Leu Leu Thr Lys Gly Ala Gln Lys Gly Met
            660                 665                 670

Gly Val Ala Val Phe Asn Asp Asn Leu Arg Asn Ala Leu Asp Gly Asn
            675                 680                 685

Val Phe Asp Ser Ser Ala Gln Gly Phe Ala Thr Gly Ala Thr Gly Leu
            690                 695                 700

Thr Asp Ala Ile Lys Arg Gly Val Glu Gly Ser Ile Asn Asp Phe Thr
705                 710                 715                 720

Ser Ser Pro Ser Glu Thr Ile Asn Tyr Val Ser Cys His Asp Asn Tyr
            725                 730                 735

Thr Leu Trp Asp Lys Ile Ala Leu Ser Asn Pro Asn Asp Ser Glu Ala
            740                 745                 750

Asp Arg Ile Lys Met Asp Glu Leu Ala Gln Ala Val Val Met Thr Ser
            755                 760                 765

Gln Gly Val Pro Phe Met Gln Gly Gly Glu Met Leu Arg Thr Lys
            770                 775                 780

Gly Gly Asn Asp Asn Ser Tyr Asn Ala Gly Asp Thr Val Asn Glu Phe
785                 790                 795                 800

Asp Trp Ser Arg Lys Ala Gln Tyr Pro Asp Val Phe Asn Tyr Tyr Ser
            805                 810                 815

Gly Leu Ile His Leu Arg Leu Asp His Pro Ala Phe Arg Met Thr Thr
            820                 825                 830

Ala Asn Glu Ile Asn Ser His Leu Gln Phe Leu Asn Ser Pro Glu Asn
            835                 840                 845

Thr Val Ala Tyr Glu Leu Thr Asp His Val Asn Lys Asp Lys Trp Gly
            850                 855                 860

Asn Ile Ile Val Val Tyr Asn Pro Asn Lys Thr Ala Ala Thr Ile Asn
865                 870                 875                 880

Leu Pro Ser Gly Lys Trp Ala Ile Asn Ala Thr Ser Gly Lys Val Gly
            885                 890                 895

Glu Ser Thr Leu Gly Gln Ala Glu Gly Ser Val Gln Val Pro Gly Ile
            900                 905                 910

Ser Met Met Ile Leu His Gln Glu Val Ser Pro Asp His Gly Lys Lys
            915                 920                 925
```

<210> SEQ ID NO 19
<211> LENGTH: 471
<212> TYPE: PRT
<213> ORGANISM: Rhizomucor pusillus

<400> SEQUENCE: 19

```
Met Lys Phe Ser Ile Ser Leu Ser Ala Ala Ile Val Leu Phe Ala Ala
1               5                   10                  15

Ala Thr Ser Leu Ala Ser Pro Leu Pro Gln Gln Gln Arg Tyr Gly Lys
            20                  25                  30

Arg Ala Thr Ser Asp Asp Trp Lys Ser Lys Ala Ile Tyr Gln Leu Leu
        35                  40                  45

Thr Asp Arg Phe Gly Arg Ala Asp Asp Ser Thr Ser Asn Cys Ser Asn
    50                  55                  60

Leu Ser Asn Tyr Cys Gly Gly Thr Tyr Glu Gly Ile Thr Lys His Leu
65                  70                  75                  80

Asp Tyr Ile Ser Gly Met Gly Phe Asp Ala Ile Trp Ile Ser Pro Ile
                85                  90                  95

Pro Lys Asn Ser Asp Gly Gly Tyr His Gly Tyr Trp Ala Thr Asp Phe
            100                 105                 110

Tyr Gln Leu Asn Ser Asn Phe Gly Asp Glu Ser Gln Leu Lys Ala Leu
        115                 120                 125

Ile Gln Ala Ala His Glu Arg Asp Met Tyr Val Met Leu Asp Val Val
    130                 135                 140

Ala Asn His Ala Gly Pro Thr Ser Asn Gly Tyr Ser Gly Tyr Thr Phe
145                 150                 155                 160

Gly Asp Ala Ser Leu Tyr His Pro Lys Cys Thr Ile Asp Tyr Asn Asp
                165                 170                 175

Gln Thr Ser Ile Glu Gln Cys Trp Val Ala Asp Glu Leu Pro Asp Ile
            180                 185                 190

Asp Thr Glu Asn Ser Asp Asn Val Ala Ile Leu Asn Asp Ile Val Ser
        195                 200                 205

Gly Trp Val Gly Asn Tyr Ser Phe Asp Gly Ile Arg Ile Asp Thr Val
    210                 215                 220

Lys His Ile Arg Lys Asp Phe Trp Thr Gly Tyr Ala Glu Ala Ala Gly
225                 230                 235                 240

Val Phe Ala Thr Gly Glu Val Phe Asn Gly Asp Pro Ala Tyr Val Gly
                245                 250                 255

Pro Tyr Gln Lys Tyr Leu Pro Ser Leu Ile Asn Tyr Pro Met Tyr Tyr
            260                 265                 270

Ala Leu Asn Asp Val Phe Val Ser Lys Ser Lys Gly Phe Ser Arg Ile
        275                 280                 285

Ser Glu Met Leu Gly Ser Asn Arg Asn Ala Phe Glu Asp Thr Ser Val
    290                 295                 300

Leu Thr Thr Phe Val Asp Asn His Asp Asn Pro Arg Phe Leu Asn Ser
305                 310                 315                 320

Gln Ser Asp Lys Ala Leu Phe Lys Asn Ala Leu Thr Tyr Val Leu Leu
                325                 330                 335

Gly Glu Gly Ile Pro Ile Val Tyr Tyr Gly Ser Glu Gln Gly Phe Ser
            340                 345                 350

Gly Gly Ala Asp Pro Ala Asn Arg Glu Val Leu Trp Thr Thr Asn Tyr
        355                 360                 365

Asp Thr Ser Ser Asp Leu Tyr Gln Phe Ile Lys Thr Val Asn Ser Val
```

```
              370               375               380
Arg Met Lys Ser Asn Lys Ala Val Tyr Met Asp Ile Tyr Val Gly Asp
385                 390                 395                 400

Asn Ala Tyr Ala Phe Lys His Gly Asp Ala Leu Val Val Leu Asn Asn
                405                 410                 415

Tyr Gly Ser Gly Ser Thr Asn Gln Val Ser Phe Ser Val Ser Gly Lys
            420                 425                 430

Phe Asp Ser Gly Ala Ser Leu Met Asp Ile Val Ser Asn Ile Thr Thr
        435                 440                 445

Thr Val Ser Ser Asp Gly Thr Val Thr Phe Asn Leu Lys Asp Gly Leu
    450                 455                 460

Pro Ala Ile Phe Thr Ser Ala
465                 470

<210> SEQ ID NO 20
<211> LENGTH: 514
<212> TYPE: PRT
<213> ORGANISM: B. stearothermophilus

<400> SEQUENCE: 20

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Ala Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Ser Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Asp Val Arg Ser Gln Thr Gly
                245                 250                 255

Lys Pro Leu Phe Thr Val Gly Glu Tyr Trp Ser Tyr Asp Ile Asn Lys
            260                 265                 270
```

Leu His Asn Tyr Ile Met Lys Thr Asn Gly Thr Met Ser Leu Phe Asp
            275                 280                 285

Ala Pro Leu His Asn Lys Phe Tyr Thr Ala Ser Lys Ser Gly Gly Thr
290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
            355                 360                 365

Tyr Tyr Gly Ile Pro Gln Tyr Asn Ile Pro Ser Leu Lys Ser Lys Ile
370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Trp Ser Ile Thr Thr
                485                 490                 495

Arg Pro Trp Thr Asp Glu Phe Val Arg Trp Thr Glu Pro Arg Leu Val
            500                 505                 510

Ala Trp

<210> SEQ ID NO 21
<211> LENGTH: 483
<212> TYPE: PRT
<213> ORGANISM: Bacillus licheniformis

<400> SEQUENCE: 21

Ala Asn Leu Asn Gly Thr Leu Met Gln Tyr Phe Glu Trp Tyr Met Pro
1               5                   10                  15

Asn Asp Gly Gln His Trp Arg Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
                180                 185                 190

Tyr Asp Tyr Leu Met Tyr Ala Asp Ile Asp Tyr Asp His Pro Asp Val
                195                 200                 205

Ala Ala Glu Ile Lys Arg Trp Gly Thr Trp Tyr Ala Asn Glu Leu Gln
210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
                260                 265                 270

Tyr Leu Asn Lys Thr Asn Phe Asn His Ser Val Phe Asp Val Pro Leu
                275                 280                 285

His Tyr Gln Phe His Ala Ala Ser Thr Gln Gly Gly Gly Tyr Asp Met
290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
                340                 345                 350

Thr Arg Glu Ser Gly Tyr Pro Gln Val Phe Tyr Gly Asp Met Tyr Gly
                355                 360                 365

Thr Lys Gly Asp Ser Gln Arg Glu Ile Pro Ala Leu Lys His Lys Ile
                370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
                420                 425                 430

Gly Gly Ala Lys Arg Met Tyr Val Gly Arg Gln Asn Ala Gly Glu Thr
                435                 440                 445

Trp His Asp Ile Thr Gly Asn Arg Ser Glu Pro Val Val Ile Asn Ser
450                 455                 460

Glu Gly Trp Gly Glu Phe His Val Asn Gly Gly Ser Val Ser Ile Tyr
465                 470                 475                 480

Val Gln Arg

<210> SEQ ID NO 22
<211> LENGTH: 483
<212> TYPE: PRT
<213> ORGANISM: Bacillus amyloliquefaciens

<400> SEQUENCE: 22

Val Asn Gly Thr Leu Met Gln Tyr Phe Glu Trp Tyr Thr Pro Asn Asp
1               5                   10                  15

-continued

```
Gly Gln His Trp Lys Arg Leu Gln Asn Asp Ala Glu His Leu Ser Asp
             20                  25                  30
Ile Gly Ile Thr Ala Val Trp Ile Pro Pro Ala Tyr Lys Gly Leu Ser
         35                  40                  45
Gln Ser Asp Asn Gly Tyr Gly Pro Tyr Asp Leu Tyr Asp Leu Gly Glu
     50                  55                  60
Phe Gln Gln Lys Gly Thr Val Arg Thr Lys Tyr Gly Thr Lys Ser Glu
 65                  70                  75                  80
Leu Gln Asp Ala Ile Gly Ser Leu His Ser Arg Asn Val Gln Val Tyr
                 85                  90                  95
Gly Asp Val Val Leu Asn His Lys Ala Gly Ala Asp Ala Thr Glu Asp
            100                 105                 110
Val Thr Ala Val Glu Val Asn Pro Ala Asn Arg Asn Gln Glu Thr Ser
        115                 120                 125
Glu Glu Tyr Gln Ile Lys Ala Trp Thr Asp Phe Arg Phe Pro Gly Arg
    130                 135                 140
Gly Asn Thr Tyr Ser Asp Phe Lys Trp His Trp Tyr His Phe Asp Gly
145                 150                 155                 160
Ala Asp Trp Asp Glu Ser Arg Lys Ile Ser Arg Ile Phe Lys Phe Arg
                165                 170                 175
Gly Glu Gly Lys Ala Trp Asp Trp Glu Val Ser Ser Glu Asn Gly Asn
            180                 185                 190
Tyr Asp Tyr Leu Met Tyr Ala Asp Val Asp Tyr Asp His Pro Asp Val
        195                 200                 205
Val Ala Glu Thr Lys Lys Trp Gly Ile Trp Tyr Ala Asn Glu Leu Ser
    210                 215                 220
Leu Asp Gly Phe Arg Ile Asp Ala Ala Lys His Ile Lys Phe Ser Phe
225                 230                 235                 240
Leu Arg Asp Trp Val Gln Ala Val Arg Gln Ala Thr Gly Lys Glu Met
                245                 250                 255
Phe Thr Val Ala Glu Tyr Trp Gln Asn Asn Ala Gly Lys Leu Glu Asn
            260                 265                 270
Tyr Leu Asn Lys Thr Ser Phe Asn Gln Ser Val Phe Asp Val Pro Leu
        275                 280                 285
His Phe Asn Leu Gln Ala Ala Ser Ser Gln Gly Gly Tyr Asp Met
    290                 295                 300
Arg Arg Leu Leu Asp Gly Thr Val Val Ser Arg His Pro Glu Lys Ala
305                 310                 315                 320
Val Thr Phe Val Glu Asn His Asp Thr Gln Pro Gly Gln Ser Leu Glu
                325                 330                 335
Ser Thr Val Gln Thr Trp Phe Lys Pro Leu Ala Tyr Ala Phe Ile Leu
            340                 345                 350
Thr Arg Glu Ser Gly Tyr Pro Gln Val Phe Tyr Gly Asp Met Tyr Gly
        355                 360                 365
Thr Lys Gly Thr Ser Pro Lys Glu Ile Pro Ser Leu Lys Asp Asn Ile
    370                 375                 380
Glu Pro Ile Leu Lys Ala Arg Lys Glu Tyr Ala Tyr Gly Pro Gln His
385                 390                 395                 400
Asp Tyr Ile Asp His Pro Asp Val Ile Gly Trp Thr Arg Glu Gly Asp
                405                 410                 415
Ser Ser Ala Ala Lys Ser Gly Leu Ala Ala Leu Ile Thr Asp Gly Pro
            420                 425                 430
Gly Gly Ser Lys Arg Met Tyr Ala Gly Leu Lys Asn Ala Gly Glu Thr
```

```
                    435                 440                 445
Trp Tyr Asp Ile Thr Gly Asn Arg Ser Asp Thr Val Lys Ile Gly Ser
    450                 455                 460

Asp Gly Trp Gly Glu Phe His Val Asn Asp Gly Ser Val Ser Ile Tyr
465                 470                 475                 480

Val Gln Lys

<210> SEQ ID NO 23
<211> LENGTH: 483
<212> TYPE: PRT
<213> ORGANISM: Artificial sequence
<220> FEATURE:
<223> OTHER INFORMATION: Recombinant alpha-amylase conjugate

<400> SEQUENCE: 23

Ala Ala Val Asn Gly Thr Leu Met Gln Tyr Phe Glu Trp Tyr Thr Pro
1               5                   10                  15

Asn Asp Gly Gln His Trp Lys Arg Leu Gln Asn Asp Ala Glu His Leu
            20                  25                  30

Ser Asp Ile Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
        195                 200                 205

Ala Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
        275                 280                 285

His Tyr Gln Phe His Ala Ala Ser Thr Gln Gly Gly Gly Tyr Asp Met
    290                 295                 300

Arg Lys Leu Leu Asn Gly Thr Val Val Ser Lys His Pro Leu Lys Ser
305                 310                 315                 320
```

```
Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Asp Ser Gln Arg Glu Ile Pro Ala Leu Lys His Lys Ile
    370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
            420                 425                 430

Gly Gly Ala Lys Arg Met Tyr Val Gly Arg Gln Asn Ala Gly Glu Thr
        435                 440                 445

Trp His Asp Ile Thr Gly Asn Arg Ser Glu Pro Val Val Ile Asn Ser
    450                 455                 460

Glu Gly Trp Gly Glu Phe His Val Asn Gly Gly Ser Val Ser Ile Tyr
465                 470                 475                 480

Val Gln Arg

<210> SEQ ID NO 24
<211> LENGTH: 483
<212> TYPE: PRT
<213> ORGANISM: Artificial sequence
<220> FEATURE:
<223> OTHER INFORMATION: Bacillus hybrid alpha-amylase

<400> SEQUENCE: 24

Ala Ala Val Asn Gly Thr Leu Met Gln Tyr Phe Glu Trp Tyr Thr Pro
1               5                   10                  15

Asn Asp Gly Gln His Trp Lys Arg Leu Gln Asn Asp Ala Glu His Leu
                20                  25                  30

Ser Asp Ile Gly Ile Thr Ala Val Trp Ile Pro Pro Ala Tyr Lys Ala
            35                  40                  45

Ile Ser Gln Ala Asp Val Gly Tyr Gly Ala Tyr Asp Leu Tyr Asp Leu
        50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Ala Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
130                 135                 140

Gly Arg Gly Ser Thr Tyr Ser Asp Phe Lys Trp Tyr Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Thr Trp Asp Trp Glu Val Ser Asn Glu Phe Gly Asn
            180                 185                 190
```

```
Tyr Asp Tyr Leu Met Tyr Ala Asp Phe Asp Tyr Asp His Pro Asp Val
            195                 200                 205

Val Ala Glu Ile Lys Arg Trp Gly Thr Trp Tyr Ala Asn Glu Leu Gln
210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
            245                 250                 255

Phe Thr Val Ala Glu Tyr Trp Ser Asn Asp Leu Gly Ala Leu Glu Asn
            260                 265                 270

Tyr Leu Asn Lys Thr Asn Phe Asn His Ser Val Phe Asp Val Pro Leu
            275                 280                 285

His Tyr Gln Phe His Ala Ala Ser Thr Gln Gly Gly Gly Tyr Asp Met
290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
            325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
            355                 360                 365

Thr Lys Gly Asp Ser Gln Arg Glu Ile Pro Ala Leu Lys His Lys Ile
            370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
                420                 425                 430

Gly Gly Ala Lys Arg Met Tyr Val Gly Arg Gln Asn Ala Gly Glu Thr
            435                 440                 445

Trp His Asp Ile Thr Gly Asn Arg Ser Glu Pro Val Val Ile Asn Ser
450                 455                 460

Glu Gly Trp Gly Glu Phe His Val Asn Gly Gly Ser Val Ser Ile Tyr
465                 470                 475                 480

Val Gln Arg

<210> SEQ ID NO 25
<211> LENGTH: 483
<212> TYPE: PRT
<213> ORGANISM: Artificial sequence
<220> FEATURE:
<223> OTHER INFORMATION: Bacillus hybrid alpha-amylase variant

<400> SEQUENCE: 25

Ala Ala Val Asn Gly Thr Leu Met Gln Tyr Phe Glu Trp Tyr Thr Pro
1               5                   10                  15

Asn Asp Gly Gln His Trp Lys Arg Leu Gln Asn Asp Ala Glu His Leu
            20                  25                  30

Ser Asp Ile Gly Ile Thr Ala Val Trp Ile Pro Pro Ala Tyr Lys Ala
        35                  40                  45

Ile Ser Gln Ala Asp Val Gly Tyr Gly Ala Tyr Asp Leu Tyr Asp Leu
    50                  55                  60

Gly Glu Phe Trp Gln Lys Gly Thr Val Arg Thr Lys Tyr Gly Thr Lys
```

```
            65                  70                  75                  80
Gly Glu Leu Gln Ser Ala Ile Lys Ser Leu His Ser Arg Asp Ile Asn
                    85                  90                  95

Val Tyr Gly Asp Val Val Ile Asn His Lys Ala Gly Ala Asp Ala Thr
                100                 105                 110

Glu Asp Val Thr Ala Val Glu Val Asp Pro Ala Asp Arg Asn Arg Val
                115                 120                 125

Ile Ser Gly Glu His Leu Ile Lys Ala Trp Thr His Phe His Phe Pro
        130                 135                 140

Gly Arg Gly Ser Thr Tyr Ser Asp Phe Lys Trp Tyr Trp Tyr His Phe
145                 150                 155                 160

Asp Gly Thr Asp Trp Asp Glu Ser Arg Lys Leu Asn Arg Ile Tyr Leu
                165                 170                 175

Phe Gln Gly Lys Thr Trp Asp Trp Pro Val Ser Asn Glu Phe Gly Asn
                180                 185                 190

Tyr Asp Tyr Leu Met Tyr Ala Asp Tyr Asp Tyr Asp Tyr Pro Asp Val
                195                 200                 205

Val Ala Glu Ile Thr Arg Trp Gly Thr Trp Tyr Ala Asn Glu Leu Gln
        210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Ser Asn Asp Leu Gly Ala Leu Glu Asn
                260                 265                 270

Tyr Leu Asn Lys Thr Asn Phe Asn His Ser Val Phe Asp Val Pro Leu
                275                 280                 285

His Tyr Gln Phe His Ala Ala Ser Thr Gln Gly Gly Tyr Asp Met
        290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
                340                 345                 350

Thr Arg Glu Ser Gly Tyr Pro Ser Val Phe Tyr Gly Asp Met Tyr Gly
                355                 360                 365

Thr Lys Gly Asp Ser Gln Arg Glu Ile Pro Ala Leu Lys His Lys Ile
        370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Val
                405                 410                 415

Ser Ser Val Ala Asn Ser Gly Leu Ala Ala Leu Ile Thr Asp Gly Pro
                420                 425                 430

Gly Gly Ala Lys Trp Met Tyr Val Gly Arg Gln Asn Ala Gly Glu Thr
                435                 440                 445

Trp His Asp Ile Thr Gly Asn Arg Ser Glu Pro Val Val Ile Asn Ser
        450                 455                 460

Glu Gly Trp Gly Glu Phe His Val Asn Gly Gly Ser Val Ser Ile Tyr
465                 470                 475                 480

Val Gln Arg
```

COMPOSITIONS FOR PRODUCING GLUCOSE SYRUPS

CROSS-REFERENCE TO RELATED APPLICATIONS

This application is a 35 U.S.C. 371 national application of PCT/EP2015/052545 filed Feb. 6, 2015 which claims priority or the benefit under 35 U.S.C. 119 of European application nos. 14154239.9 and 14195687.0 filed Feb. 7, 2014 and Dec. 1, 2014, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to compositions comprising an alpha-amylase, a pullulanase and a glucoamylase. Furthermore the present invention relates to methods of producing glucose syrup comprising high % DX.

Description of the Related Art

Starch usually consists of about 80% amylopectin and 20% amylose. Amylopectin is a branched polysaccharide in which linear chains alpha-1,4 D-glucose residues are joined by alpha-1,6 glucosidic linkages. Amylopectin is partially degraded by alpha-amylase, which hydrolyzes the 1,4-alpha-glucosidic linkages to produce branched and linear oligosaccharides.

Alpha-amylases are used commercially for a variety of purposes such as in the initial stages of starch processing (e.g., liquefaction). Prolonged degradation of amylopectin by alpha-amylase results in the formation of so-called alpha-limit dextrins that are not susceptible to further hydrolysis by the alpha-amylase. Alpha-amylases (1,4-α-D-glucan glucanohydrolase, EC 3.2.1.1) constitute a group of enzymes which catalyze hydrolysis of starch and other linear and branched 1,4-glucosidic oligo- and polysaccharides.

Branched oligosaccharides can be hydrolyzed into linear oligosaccharides by a debranching enzyme. The remaining branched oligosaccharides can be depolymerized to D-glucose by glucoamylase, which hydrolyzes linear oligosaccharides into D-glucose.

Debranching enzymes which can attack amylopectin are divided into two classes: isoamylases (E.C. 3.2.1.68) and pullulanases (E.C. 3.2.1.41), respectively. Isoamylase hydrolyses alpha-1,6-D-glucosidic branch linkages in amylopectin and beta-limit dextrins and can be distinguished from pullulanases by the inability of isoamylase to attack pullulan, and by their limited action on alpha-limit dextrins.

It is well-known in the art to add isoamylases or pullulanases in starch conversion processes. Pullulanase is a starch debranching enzyme having pullulan 6-glucano-hydrolase activity (EC3.2.1.41) that catalyzes the hydrolysis the α-1,6-glycosidic bonds in pullulan, releasing maltotriose with reducing carbohydrate ends. Usually pullulanase is used in combination with an alpha amylase and/or a glucoamylase.

Pullulanases are known in the art. U.S. Pat. Nos. 6,074,854 and 5,817,498 disclose a pullulanase from *Bacillus deramificans*. WO2009/075682 disclose a pullulanase derived from *Bacillus acidopullulyticus*.

Glucoamylase (1,4-alpha-D-glucan glucohydrolase, EC 3.2.1.3) is an enzyme, which catalyzes the release of D-glucose from the non-reducing ends of starch or related oligo- and polysaccharide molecules. Glucoamylases are produced by several filamentous fungi and yeast, with those from *Aspergillus, Talaromyces, Penicillium*, and *Trametes* being particularly commercially important.

Commercially, glucoamylases are used to convert starchy material, which is already partially hydrolyzed by an alpha-amylase and e.g., a pullulanase, to glucose in the form of syrup.

Before the enzymatic treatment the starch material, such as whole grains, may be reduced in particle size, e.g., by milling, in order to open up the structure and allowing for further processing. In dry milling whole kernels are milled and used. Wet milling gives a good separation of germ and meal (starch granules and protein) and is often applied at locations where the starch hydrolyzate is used in the production of, e.g., syrups. Both dry and wet milling is well known in the art of starch processing and may be used in a process of the invention.

After milling, typically the starch material is liquefied. Liquefaction is carried out in the presence of an alpha-amylase, preferably a bacterial alpha-amylase and/or acid fungal alpha-amylase.

During liquefaction, the long-chained starch is degraded into branched and linear shorter units (maltodextrins) by an alpha-amylase. Liquefaction may be carried out as a three-step hot slurry process. The liquefaction process is carried out at between 70-95° C., such as 80-90° C., such as around 85° C., for about 10 minutes to 5 hours, typically for 1-2 hours. After such treatment, the liquefied starch will typically have a "dextrose equivalent" (DE) of 10-15.

Generally liquefaction and liquefaction conditions are well known in the art.

For the production of glucose syrup the liquefied starch material is saccharified. In a typical saccharification process, maltodextrins produced during liquefaction are converted into dextrose by adding a glucoamylase and a debranching enzyme, such as an isoamylase (U.S. Pat. No. 4,335,208) or a pullulanase. The temperature is lowered to 60° C., prior to the addition of the glucoamylase and debranching enzyme. The saccharification process proceeds for 24-72 hours. Prior to addition of the saccharifying enzymes, the pH is reduced to below 4.5, while maintaining a high temperature (above 95° C.), to inactivate the liquefying alpha-amylase.

For the production of syrup enzyme compositions used should at least comprise a glucoamylase and a pullulanase, however, often alpha-amylase activity will also be present, e.g. when using *Aspergillus niger* glucoamylase the *A. niger* alpha-amylase from the production host will also be present in the composition. It has surprisingly been found that in order to reach high % DX values of the syrup, e.g., above 95%, the level of alpha-amylase present in the composition should be carefully controlled.

The present invention provides compositions and methods for producing high glucose syrups having a % DX of around 96%.

Applications for higher DX syrups are: production of DMH (dextrose monohydrate), fermentation chemicals such as organic acids (such as citric acid, lactic acid, etc.) or amino acids (such as L-lysine, L-threonine, L-tryptophane, monosodium glutamate and L-cysteine), High fructose corn syrups, crystalline fructose and other specialty syrups.

SUMMARY OF THE INVENTION

In a first aspect, the present invention relates to a composition comprising an alpha-amylase, a pullulanase and a glucoamylase enzyme, wherein the ratio of pullulanase dose expressed as NPUN/g, to alpha-amylase dose expressed as FAU(A)/g or a KNU/g is at least 60.

In a second aspect, the present invention relates to a method of making glucose syrup from liquefied starch comprising, (a) contacting the liquefied starch with a glucoamylase, a pullulanase, and optionally an alpha-amylase wherein the ratio of pullulanase dose expressed as NPUN/gDS, to alpha-amylase dose expressed as FAU(A)/gDS or as KNU/gDS is at least 60, particularly at least 75, particularly at least 100, more particularly at least 150, more particularly at least 200, more particularly at least 250, more particularly at least 300, more particularly at least 400, more particularly at least 500, more particularly at least 600, more particularly at least 800 or if no alpha-amylase present the pullulanase is present in a dose of at least 0.5, particularly at least 0.75, particularly at least 1.0, particularly at least 1.5 NPUN/gDS, and (b) saccharifying the liquefied starch.

Definitions

Alpha-amylase: Alpha-amylases (1,4-alpha-D-glucan glucanohydrolase, E.C. 3.2.1.1) are a group of enzymes which catalyze the hydrolysis of starch and other linear and branched 1,4 glucosidic oligo- and polysaccharides. Alpha-amylases used according to the present invention may be obtained from fungal or bacterial sources. For purposes of the present invention, fungal alpha amylase activity can be determined as FAU(A) using the alpha amylase assay described in the Materials and Methods. Activity of bacterial alpha-amylases can be determined as Kilo Novo alpha-amylase Units (KNU) according to the procedure described in the paragraph "Kilo Novo alpha-amylase Units (KNU)" below.

Acid alpha-Amylase Units (FAU(A)): Acid alpha-amylase activity may be measured in FAU(A) (Acid Fungal Alpha-amylase Units). 1 FAU(A) is defined as the amount of enzyme which degrades 5.260 mg starch dry matter per hour under the standard conditions specified in the table "First reaction, starch degradation" below.

Acid alpha-amylase, an endo-alpha-amylase (1,4-alpha-D-glucan-glucanohydrolase, E.C. 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions.

FAU(A), the acid alpha-amylase activity is determined in accordance with the following description. The principle of the reaction is based on the two steps. In the first step, the enzyme acid alpha-amylase hydrolyzes starch into different oligosaccharides. In the second step, iodine forms a blue complex with starch but not with its degradation products. The intensity of color is therefore directly proportional to the concentration of starch. The activity is determined using reverse colorimetry as a reduction in the concentration of starch under specified analytic conditions.

| First reaction, starch degradation | |
|---|---|
| Substrate | Starch, approx. 0.3 g/L |
| Buffer | Citrate, approx. 0.05M |
| | CaCl2, 1.85 mM |
| pH | 2.50 ± 0.05 |
| Incubation temperature | 37° C. |
| Reaction time | 180 seconds |
| Enzyme working range | 0.01-0.04 FAU(A)/mL |

| Second reaction, starch-iodine complex | |
|---|---|
| Iodine | 0.0432 g/L |
| Incubation temperature | 37° C. |
| Reaction time | 60 seconds |
| Wavelength | 600 nm |

Kilo Novo Alpha-Amylase Units (KNU)

Bacterial alpha-amylase activity may be determined using potato starch as substrate. The method is based on breakdown of starch in solution by amylase and the fact that starch gives a blue-black colour in presence of iodine. As the enzyme reaction proceeds, aliquots of the reaction are withdrawn and analyzed for their starch content by mixing with an iodine solution. As starch is broken down, the blue-black colour in the presence of iodine fades and gradually turns into a reddish-brown colour. This is compared with a coloured glass standard. The end point is reached when the colour matches the glass standard.

One Kilo Novo alpha amylase Unit (KNU) is defined as the amount of enzyme which, under standard conditions as defined in the "KNU" table below (i.e., at 37° C.+/−0.05; 0.0003 M $Ca^{2+}$; and pH 5.6) dextrinizes 5260 mg/hour starch dry substance; e.g. Merck Amylum solubile.

| KNU | |
|---|---|
| Temperature | 37 ± 0.05° C. |
| pH | 5.6 |
| Substrate concentration | 4.63 mg dry weight/mL |
| Reaction time | 7-20 min, up to 1 hr |
| $Ca^{2+}$ concentration | approx. 0.0003M for reaction mix containing 2 mL sample solution |

Pullulanase: The term "pullulanase" means a starch debranching enzyme having pullulan 6-glucano-hydrolase activity (EC3.2.1.41) that catalyzes the hydrolyses the α-1, 6-glycosidic bonds in pullulan, releasing maltotriose with reducing carbohydrate ends. For purposes of the present invention, pullulanase activity is determined as NPUN according to the procedure described in the Materials and Methods and in the following paragraph.

Pullulanase activity (NPUN): The NPUN (New Pullulanase Unit Novozymes) is a unit of endopullulanase activity measured in the following procedure.

1 NPUN=One pullulanase unit (NPUN) is defined as the enzyme amount, which releases reducing ends equivalent to 0.35 μmol glucose per minute under the standard conditions specified in the table "First reaction, pullulan degradation" below.

In the first reaction, the substrate is equally present in both sample main and sample blank. However, the reaction of sample main is performed at pH 5.0, while there is no reaction in the sample blank at pH 9.6, where neither pullulanases nor amyloglucosidases (glucoamylase) are enzymatically active.

| First reaction, pullulan degradation | |
|---|---|
| Substrate | BH4 reduced pullulan, 5.3 g/L |
| Buffer (main) | Acetate, approx. 0.1M |
| | EDTA, 5.3 mM |
| | Acarbose, 0.018% |
| | (if sample contains glucoamylase) |

| First reaction, pullulan degradation | |
|---|---|
| pH (main) | 5.0 |
| Buffer (blank) | CHES, 42 mM |
| | acetate, 17 mM |
| | EDTA, 5.3 mM |
| pH (blank) | 9.6 |
| Incubation temperature | 50° C. |
| Reaction time | 540 seconds |
| Enzyme working range | 0.03-0.15 NPUN/mL |

In the second reaction, the pH is adjusted to approx. 9.6 and the glucose in samples is phosphorylated to non-reducing D-glucose-6-phosphate by glucokinase, which has optimal activity and stability in this range and is specific to glucose at pH 9 (ref. Goward, Biochem. J. 1986, 237, pp 415-420). This step depends on identical pH in sample main and sample blank to remove equal amounts of glucose in both.

| Second reaction, background glucose elimination | |
|---|---|
| Substrate | glucose in sample, after first reaction |
| Buffer | CHES, 58 mM (main) or 76 mM (blank) |
| | acetate, 43 mM (main) or 7.2 mM (blank) |
| | EDTA, 2.2 mM |
| | ATP, 1.11 mg/ml |
| | MgCl2, 4.4 mM |
| Glucokinase | 0.11 U/ml |
| pH | approx. 9.6 |
| Incubation temperature | 50° C. |
| Reaction time | 720 seconds |

Glucoamylase: The term glucoamylase (1,4-alpha-D-glucan glucohydrolase, EC 3.2.1.3) is defined as an enzyme, which catalyzes the release of D-glucose from the non-reducing ends of starch or related oligo- and polysaccharide molecules. For purposes of the present invention, glucoamylase activity is determined as AGU according to the procedure described in the Materials and Methods and in the following paragraph.

Glucoamylase activity (AGU): The Glucoamylase Unit (AGU) is defined as the amount of enzyme, which hydrolyzes 1 micromole maltose per minute in a 0.1 M acetate buffer at an incubation temperature 37° C., a pH of 4.3, a maltose starting concentration of 100 mM, and a reaction time of 6 minutes, thereby generating alpha-D-glucose. The definition applies to an enzyme working range of 0.5-4.0 AGU/mL.

After incubation, the reaction may be stopped with NaOH and the amounts of glucose measured using the following two-step color reaction method: Glucose is phosphorylated by ATP, in a reaction catalyzed by hexokinase. The glucose-6-phosphate formed is oxidized to 6-phosphogluconate by glucose-6-phosphate dehydrogenase. In this same reaction, an equimolar amount of NAD+ is reduced to NADH with a resulting increase in absorbance at 340 nm.

Reaction conditions are as specified in the table below:

| Color reaction | |
|---|---|
| Tris | approx. 35 mM |
| ATP | 0.7 mM |
| NAD+ | 0.7 mM |
| Mg$^{2+}$ | 1.8 mM |
| Hexokinase | >850 U/L |
| Glucose-6-P-DH | >850 U/L |

| Color reaction | |
|---|---|
| pH | approx. 7.8 |
| Temperature | 37.0° C. ± 1.0° C. |
| Reaction time | 420 sec |
| Wavelength | 340 nm |

Degree of polymerization (DP): DP refers to the number (n) of anhydroglucopyranose units in a given saccharide. Examples of DP1 are monosaccharides, such as glucose and fructose. DP2 are disaccharides, such as maltose and sucrose.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Mature polypeptide: The term "mature polypeptide" means a polypeptide in its final form following translation and any post-translational modifications, such as N-terminal processing, C-terminal truncation, glycosylation, phosphorylation, etc. According to some embodiments, the mature polypeptide of SEQ ID NO: 6 consists essentially of amino acids 18 to 573 of SEQ ID NO: 6, the mature polypeptide of SEQ ID NO: 7 consists essentially of amino acids 18 to 573 of SEQ ID NO: 7, the mature polypeptide of SEQ ID NO: 8 consists essentially of amino acids 18 to 573 of SEQ ID NO: 8, the mature polypeptide of SEQ ID NO: 5 consists essentially of amino acids 18 to 573 of SEQ ID NO: 9, the mature polypeptide of SEQ ID NO: 10 consists essentially of amino acids 18 to 573 of SEQ ID NO: 10, the mature polypeptide of SEQ ID NO: 11 consists essentially of amino acids 18 to 573 of SEQ ID NO: 11, the mature polypeptide of SEQ ID NO: 12 consists essentially of amino acids 18 to 573 of SEQ ID NO: 12, the mature polypeptide of SEQ ID NO: 13 consists essentially of amino acids 18 to 576 of SEQ ID NO: 13, the mature polypeptide of SEQ ID NO: 14 consists essentially of amino acids 18 to 576 of SEQ ID NO: 14.

In particular, the mature polypeptide of SEQ ID NO: 6 may consist of amino acids 18 to 573 of SEQ ID NO: 6.

The mature polypeptide of SEQ ID NO: 7 may consist of amino acids 18 to 573 of SEQ ID NO: 7.

The mature polypeptide of SEQ ID NO: 8 may consist of amino acids 18 to 573 of SEQ ID NO: 8.

The mature polypeptide of SEQ ID NO: 9 may consist of amino acids 18 to 573 of SEQ ID NO: 9.

The mature polypeptide of SEQ ID NO: 10 may consist of amino acids 18 to 573 of SEQ ID NO: 10.

The mature polypeptide of SEQ ID NO: 11 may consist of amino acids 18 to 573 of SEQ ID NO: 11.

The mature polypeptide of SEQ ID NO: 12 may consist of amino acids 18 to 573 of SEQ ID NO: 12.

The mature polypeptide of SEQ ID NO: 13 may consist of amino acids 18 to 576 of SEQ ID NO: 13.

The mature polypeptide of SEQ ID NO: 14 may consist of amino acids 18 to 576 of SEQ ID NO: 14.

In further embodiments, the mature polypeptide of SEQ ID NO: 6 consists of amino acids 18 to 573 of SEQ ID NO: 6, the mature polypeptide of SEQ ID NO: 7 consists of amino acids 18 to 573 of SEQ ID NO: 7, the mature polypeptide of SEQ ID NO: 8 consists of amino acids 18 to 573 of SEQ ID NO: 8, the mature polypeptide of SEQ ID NO: 9 consists of amino acids 18 to 573 of SEQ ID NO: 9, the mature polypeptide of SEQ ID NO: 10 consists of amino acids 18 to 573 of SEQ ID NO: 10, the mature polypeptide of SEQ ID NO: 11 consists of amino acids 18 to 573 of SEQ ID NO: 11, the mature polypeptide of SEQ ID NO: 12 consists of amino acids 18 to 573 of SEQ ID NO: 12, the mature polypeptide of SEQ ID NO: 13 consists of amino acids 18 to 576 of SEQ ID NO: 13, and the mature polypeptide of SEQ ID NO: 14 consists of amino acids 18 to 576 of SEQ ID NO: 14.

The prediction of mature polypeptide sequences may be based on the SignalP program (Nielsen et al., 1997, *Protein Engineering* 10: 1-6) that predicts amino acids 1 to 17 of SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13 and SEQ ID NO: 14 are a signal peptide. The sequence defined by amino acids 19 to 474 (particularly 19 to 471) of SEQ ID NO: 6, SEQ ID NO: 7, SEQ ID NO: 8, SEQ ID NO: 9, SEQ ID NO: 10, SEQ ID NO: 11, or SEQ ID NO: 12 or amino acids 19 to 471 of SEQ ID NO: 13 or of SEQ ID NO: 14 is the catalytic domain. The sequence defined by amino acids 480 to 573 of SEQ ID NO: 6, SEQ ID NO: 7, SEQ ID NO: 8, SEQ ID NO: 9, SEQ ID NO: 10, SEQ ID NO: 11 or SEQ ID NO: 12 or amino acids 483 to 576 of SEQ ID NO: 13 or SEQ ID NO: 14 is a starch binding domain.

According to other embodiments, the mature polypeptide of SEQ ID NO: 18 is defined by amino acids 22 to 450 of SEQ ID NO: 18.

In further embodiments, the mature peptide of SEQ ID NO: 19 is defined by amino acids 22-471 of SEQ ID NO: 19, whereas amino acids 1-21 are a signal peptide.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of Alignment–Total Number of Gaps in Alignment)

DETAILED DESCRIPTION OF THE INVENTION

The present invention relates to methods and compositions for producing high glucose syrup. In particular glucose syrups having % DX (% DP1) values above 95%.

It has surprisingly been found that in order to reach high % DX values of the syrup, e.g., above 95%, the level of alpha-amylase present in the composition should be carefully controlled.

The methods and compositions according to the invention provides glucose syrups with higher % DX when alpha-amylase levels are optimized so that at a given ratio of NPUN to AGU the NPUN/FAU(A) or NPUN/KNU is adjusted to be at least 60, particularly at least 80. The high % DX syrups can be obtained at industrially relevant substrate concentrations—typically more than 30% initial dry solids content (DS).

In one embodiment, the present invention relates to a method of making glucose syrup from liquefied starch comprising, (a) contacting the liquefied starch with a glucoamylase, a pullulanase, and optionally an alpha-amylase wherein the ratio of pullulanase dose expressed as NPUN/gDS, to alpha-amylase dose expressed as FAU(A)/gDS or KNU/gDS is at least 60, particularly at least 75, particularly at least 100, more particularly at least 150, more particularly at least 200, more particularly at least 250, more particularly at least 300, more particularly at least 400, more particularly at least 500, more particularly at least 600, more particularly at least 800 or if no alpha-amylase present the pullulanase is present in a dose of at least 0.5, particularly at least 0.75, particularly at least 1.0, particularly at least 1.5 NPUN/gDS, and (b) saccharifying the liquefied starch.

In some embodiments, the method comprises contacting the liquefied starch with a glucoamylase, a pullulanase, and optionally an alpha-amylase wherein the ratio of pullulanase dose expressed as NPUN/gDS, to alpha-amylase dose expressed as FAU(A)/gDS or KNU/gDS is within the range of 100-700, such as within the range of 200-600, such as within the range of 300-500, such as within the range of 350-500, such as within the range of 375-475, or such as within the range of 400-450.

According to other embodiments, the method comprises contacting the liquefied starch with a glucoamylase, a pullulanase, and optionally an alpha-amylase wherein the dose of alpha amylase is within the range of 0-0.008 FAU(A)/gDS and the dose of pullulanase is within the range of 0.5-1.5 NPUN/gDS.

In other embodiments, the dose of alpha amylase is within the range of 0-0.007 FAU(A)/g DS and the dose of pullulanase is within the range of 0.6-1.4 NPUN/g DS. In other embodiments the dose of alpha amylase is within the range of 0-0.006 FAU(A)/gDS and the dose of pullulanase is within the range of 0.7-1.3 NPUN/gDS.

In other embodiments, the dose of alpha amylase is within the range of 0-0.005 FAU(A)/gDS and the dose of pullulanase is within the range of 0.75-1.25 NPUN/gDS.

In other embodiments, the dose of alpha amylase is within the range of 0-0.004 FAU(A)/gDS and the dose of pullulanase is within the range of 0.8-1.2 NPUN/gDS.

In other embodiments, the dose of alpha amylase is within the range of 0-0.003 FAU(A)/gDS and the dose of pullulanase is within the range of 0.9-1.1 NPUN/gDS.

In other embodiments, the dose of alpha amylase is within the range of 0-0.0025 FAU(A)/g DS and the dose of pullulanase is within the range of 0.95-1 NPUN/g DS.

The ratio between pullulanase expressed as NPUN/gDS and glucoamylase expressed as AGU/gDS may in particular be within the range of 2-15, such as within the range of 2-10, within the range of 2-5, within the range of 3-5 or within the range of 3.5-4.

According to other embodiments, the method comprises contacting the liquefied starch with a glucoamylase, a pullulanase, and optionally an alpha-amylase wherein the dose of pullulanase is within the range of 0.5-1.5 NPUN/gDS and the dose of glucoamylase is within the range of 0.125-0.375 AGU/gDS.

In other embodiments, the dose of pullulanase is within the range of 0.6-1.4 NPUN/gDS and the dose of glucoamylase is within the range of 0.15-0.35 AGU/gDS.

In other embodiments, the dose of pullulanase is within the range of 0.7-1.3 NPUN/gDS and the dose of glucoamylase is within the range of 0.175-0.325 AGU/gDS.

In other embodiments, the dose of pullulanase is within the range of 0.8-1.2 NPUN/gDS and the dose of glucoamylase is within the range of 0.2-0.3 AGU/gDS.

At low levels of glucoamylase longer saccharification times may be needed. In one embodiment, the glucoamylase dose, expressed as AGU/gDS, is at least 0.1, particularly at least 0.15, particularly at least 0.18, particularly at least 0.2, more particularly at least 0.22, more particularly at least 0.23, more particularly at least 0.25, even more particularly at least 0.28.

Using the method and compositions according to the invention very high % DX values can be obtained. In a particular embodiment, the glucose syrup comprises a DP1 (% DX) of at least 95.8%, particularly at least 95.9%, particularly at least 96%, more particularly at least 96.1%.

Saccharification times may vary depending on enzyme dose. In one particular embodiment the saccharification time is at least 24 hrs, at least 30 hrs, at least 36 hrs, at least 48 hrs, at least 54 hrs, at least 60 hrs, at least 72 hrs.

In the process according to the invention, the starch hydrolysis/saccharification may in particular take place at a pH which is within the range of 3.5-5.0, such as at pH in the range of 4.0-4.5, and at a temperature, which is within the range of 59-70° C., such as in the range of 59-65° C. or such as in the range of 59-62° C.

The liquefied starch used as substrate for the saccharification process according to the invention may be a starch slurry or partially hydrolysed starch (liquefact or maltodextrin). In particular, the in starch slurry or partly hydrolysed starch may have a Dextrose equivalent (DE) in the range of 5-42, such as in the range of 5-30, in the range of 8-18 or such as in the range of 9-14.

The starch may be from any source, in particular from corn, wheat or tapioca. The starch slurry or partially hydrolysed starch may have residual alpha amylase activity from the liquefaction process present or it may have been deactivated, such as by reducing the pH to below 4.5, while maintaining a high temperature (above 95° C.), to inactivate the liquefying alpha-amylase.

The conductivity of said starch slurry or partially hydrolysed starch may in particular be within the range of 0-500 microS/cm. According to some embodiments the calcium content corresponds to 0-200 ppm free calcium.

In the process according to the invention, the starch hydrolysis/saccharification may in particular take place at a pH which is within the range of 3.5-5.0, such as at pH in the range of 4.0-4.7, and at a temperature, which is within the range of 58-70° C., such as in the range of 58-65° C., in the range of 59-65° C. or such as in the range of 59-62° C.

The composition comprising liquefied starch provided as a starting material; i.e. composition comprising liquefied starch provided the in step i) of the process may contain from 25-45% dry solids (% DS), such as from 25-40% DS.

The method according to the invention is applicable at industry relevant substrate doses. In one embodiment the initial dry solids content (DS) in the liquefied starch substrate is at least 25%, particularly at least 30%, more particularly at least 35%, even more particularly at least 40%.

Enzyme Compositions

The present invention also relates to compositions comprising a glucoamylase, a pullulanase and an alpha-amylase.

In a particular embodiment, the composition comprises an alpha-amylase, a pullulanase and a glucoamylase enzyme, wherein the ratio of pullulanase dose expressed as NPUN/g, to alpha-amylase dose expressed as FAU(A)/g or as KNU/g is at least 60.

More particularly, the composition comprises an alpha-amylase, a pullulanase and a glucoamylase enzyme, wherein the ratio of pullulanase dose expressed as NPUN/g, to alpha-amylase dose expressed as FAU(A)/g or as KNU/g is at least 75, particularly at least 100, more particularly at least 150, more particularly at least 200, more particularly at least 250, more particularly at least 300, more particularly at least 400, more particularly at least 500, more particularly at least 600, more particularly at least 800.

In another embodiment, the ratio of pullulanase dose expressed as NPUN/g, to alpha-amylase dose expressed as FAU(A)/g or as KNU/g is in the range from 60-1000, more particularly 70-800, more particularly 80-600, more particularly 90-500, more particularly 100-400.

The ratio of pullulanase dose expressed as NPUN/g, to alpha-amylase dose expressed as FAU(A)/g or KNU/g may in particular be within the range of 100-700, such as within the range of 200-600, such as within the range of 300-500, such as within the range of 350-500, such as within the range of 375-475, or such as within the range of 400-450.

In a further aspect, the invention relates to a composition, wherein the ratio between pullulanase expressed as NPUN/g and glucoamylase expressed as AGU/g is at least 2, particularly at least 2.5, particularly at least 3, more particularly at least 3.5, more particularly at least 5, more particularly at least 10, even more particularly at least 15.

The ratio between pullulanase expressed as NPUN/g and glucoamylase expressed as AGU/g may in particular be within the range of 2-15, such as within the range of 2-10, within the range of 2-5, within the range of 3-5 or within the range of 3.5-4.

Pullulanase

Any pullulanase may be used in a process of the present invention. In an embodiment, the pullulanase is a pullulanase from *Bacillus deramificans*,e.g., disclosed in U.S. Pat. Nos. 6,074,854 and 5,817,498, or a pullulanase derived from *Bacillus acidopullulyticus*, e.g., disclosed in WO2009/075682 (SEQ ID 4; GENESEQP: AXB71624).

Commercially available pullulanases include Promozyme D2 available from Novozymes NS, Bagsvaerd, Denmark), Novozym 26062 (Novozymes) and Optimax L 1000 (DuPont-Genencor)

Glucoamylase

A glucoamylase used according to the invention may be derived from any suitable source, e.g., derived from a microorganism or a plant. Preferred glucoamylases are of fungal or bacterial origin, selected from the group consisting of *Aspergillus* glucoamylases, in particular *A. niger* G1 or G2 glucoamylase (Boel et al., 1984, *EMBO J.* 3 (5): 1097-

1102), or variants thereof, such as those disclosed in WO 92/00381, WO 00/04136 and WO 01/04273 (from Novozymes, Denmark); the *A. awamori* glucoamylase disclosed in WO 84/02921, *A. oryzae* glucoamylase (*Agric. Biol. Chem.*, 1991, 55 (4): 941-949), or variants or fragments thereof. Other *Aspergillus* glucoamylase variants include variants with enhanced thermal stability: G137A and G139A (Chen et al., 1996, *Prot. Eng.* 9: 499-505); D257E and D293E/Q (Chen et al., 1995, *Prot. Eng.* 8: 575-582); N182 (Chen et al., 1994, *Biochem. J.* 301: 275-281); disulphide bonds, A246C (Fierobe et al., 1996, *Biochemistry* 35: 8698-8704; and introduction of Pro residues in position A435 and S436 (Li et al., 1997, *Protein Eng.* 10: 1199-1204.

Other glucoamylases include *Athelia rolfsii* (previously denoted *Corticium rolfsii*) glucoamylase (see U.S. Pat. No. 4,727,026 and Nagasaka et al., 1998, "Purification and properties of the raw-starch-degrading glucoamylases from *Corticium rolfsii*, *Appl Microbiol Biotechnol* 50:323-330), *Talaromyces* glucoamylases, in particular derived from *Talaromyces emersonii* (WO 99/28448), *Talaromyces leycettanus* (U.S. Pat. No. Re. 32,153), *Talaromyces duponti*, and *Talaromyces thermophilus* (U.S. Pat. No. 4,587,215).

Contemplated fungal glucoamylases include *Trametes cingulata*, disclosed in WO 2006/069289.

In an embodiment, the glucoamylase is derived from a strain of the genus *Pycnoporus*, in particular a strain of *Pycnoporus* as described in WO 2011/066576 (SEQ ID NOs 2, 4 or 6), or from a strain of the genus *Gloephyllum*, in particular a strain of *Gloephyllum* as described in WO 2011/068803 (SEQ ID NO: 2, 4, 6, 8, 10, 12, 14 or 16) or a strain of the genus *Nigrofomes*, in particular a strain of *Nigrofomes* sp. disclosed in WO 2012/064351 (SEQ ID NO: 2) (all references hereby incorporated by reference) or a strain of *Penicillium*, in particular *Penicillium oxalicum* disclosed in WO2011/127802 (SEQ ID NO: 2) or WO2013/036526. Contemplated are also glucoamylases which exhibit a high identity to any of the above-mentioned glucoamylases, i.e., at least 70%, at least 75%, at least 80%, at least 85%, at least 90%, at least 95%, at least 96%, at least 97%, at least 98%, at least 99%, such as 100% identity to any one of the mature parts of the enzyme sequences mentioned above.

In an embodiment, the glucoamylase is derived from a strain of the genus *Trichoderma*, in particular as described in WO2009/048487, WO2009/048488, WO2008/045489, WO2011/022465, WO2012/001139.

Commercially available glucoamylase compositions include AMG 200L; AMG 300L; SAN™ SUPER, SAN™ EXTRA L, SPIRIZYME™ PLUS, SPIRIZYME™ FUEL, SPIRIZYME™ B4U, SPIRIZYME ULTRA™, SPIRIZYME EXCEL™ and AMG™ E (from Novozymes NS, Denmark); OPTIDEX™ 300, GC480™ and GC147™ (from Genencor Int., USA); AMIGASE™ and AMIGASE™ PLUS (from DSM); G-ZYME™ G900, G-ZYME™ and G990 ZR (from DuPont-Genencor)

Alpha-Amylase

Fungal alpha-amylases include alpha-amylases derived from a strain of the genus *Aspergillus*, such as, *Aspergillus oryzae*, *Aspergillus niger* and *Aspergillus kawachii* alpha-amylases.

A preferred acidic fungal alpha-amylase is a Fungamyl-like alpha-amylase which is derived from a strain of *Aspergillus oryzae*. According to the present invention, the term "Fungamyl-like alpha-amylase" indicates an alpha-amylase which exhibits a high identity, i.e., more than 70%, more than 75%, more than 80%, more than 85% more than 90%, more than 95%, more than 96%, more than 97%, more than 98%, more than 99% or even 100% identity to the mature part of the amino acid sequence shown in SEQ ID NO: 10 in WO 96/23874.

Another preferred acidic alpha-amylase is derived from a strain *Aspergillus niger*. In a preferred embodiment, the acid fungal alpha-amylase is the one from *A. niger* disclosed as "AMYA_ASPNG" in the Swiss-prot/TeEMBL database under the primary accession no. P56271 and described in WO 89/01969 (Example 3).

Other contemplated wild-type alpha-amylases include those derived from a strain of the genera *Rhizomucor* and *Meripilus*, preferably a strain of *Rhizomucor pusillus* (WO 2004/055178 incorporated by reference) or *Meripilus giganteus*.

In a preferred embodiment, the alpha-amylase is derived from *Aspergillus kawachii* and disclosed by Kaneko et al., 1996, *J. Ferment. Bioeng.* 81: 292-298, "Molecular-cloning and determination of the nucleotide-sequence of a gene encoding an acid-stable alpha-amylase from *Aspergillus kawachii*"; and further as EMBL:#AB008370.

The fungal alpha-amylase may also be a wild-type enzyme comprising a starch-binding domain (SBD) and an alpha-amylase catalytic domain (i.e., non-hybrid), or a variant thereof. In an embodiment the wild-type alpha-amylase is derived from a strain of *Aspergillus kawachii*.

Fungal Hybrid Alpha-Amylase

In a preferred embodiment, the alpha amylase is a fungal acid alpha-amylase is a hybrid alpha-amylase. Preferred examples of fungal hybrid alpha-amylases include the ones disclosed in WO 2005/003311 or U.S. application publication no. 2005/0054071 (Novozymes) or U.S. application No. 60/638,614 (Novozymes) which is hereby incorporated by reference. A hybrid alpha-amylase may comprise an alpha-amylase catalytic domain (CD) and a carbohydrate-binding domain/module (CBM), such as a starch binding domain, and optional a linker.

Specific examples of contemplated hybrid alpha-amylases include those disclosed in Table 1 to 5 of the examples in U.S. application No. 60/638,614, including Fungamyl variant with catalytic domain JA118 and *Athelia rolfsii* SBD (SEQ ID NO:100 in U.S. 60/638,614), *Rhizomucor pusillus* alpha-amylase with *Athelia rolfsii* AMG linker and SBD (SEQ ID NO:101 in U.S. 60/638,614), *Rhizomucor pusillus* alpha-amylase with *Aspergillus niger* glucoamylase linker and SBD (which is disclosed in Table 5 as a combination of amino acid sequences SEQ ID NO: 20, SEQ ID NO: 72 and SEQ ID NO: 96 in U.S. application Ser. No. 11/316,535) or as V039 in Table 5 in WO 2006/069290, and *Meripilus giganteus* alpha-amylase with *Athelia rolfsii* glucoamylase linker and SBD (SEQ ID NO: 102 in U.S. application No. 60/638,614). Other specifically contemplated hybrid alpha-amylases are any of the ones listed in Tables 3, 4, 5, and 6 in Example 4 in U.S. application Ser. No. 11/316,535 and WO 2006/069290 (hereby incorporated by reference).

Other specific examples of contemplated hybrid alpha-amylases include those disclosed in U.S. application publication no. 2005/0054071, including those disclosed in Table 3 on page 15, such as *Aspergillus niger* alpha-amylase with *Aspergillus kawachii* linker and starch binding domain.

Contemplated are also alpha-amylases which exhibit a high identity to any of above mention alpha-amylases, i.e., more than 70%, more than 75%, more than 80%, more than 85% more than 90%, more than 95%, more than 96%, more than 97%, more than 98%, more than 99% or even 100% identity to the mature enzyme sequences.

Bacterial Alpha-Amylase

Bacterial alpha-amylases useful in the processes according to the invention include alpha-amylases derived from a strain of the genus *Bacillus*, such as *Bacillus licheniformis* and *Bacillus stearothermophilus*.

Commercial Alpha-Amylase Products

Preferred commercial compositions comprising alpha-amylase include MYCOLASE™ (DSM), BAN™, TERMAMYL™ SC, FUNGAMYL™, LIQUOZYME™ X, LIQUOZYME™ SC and SAN™ SUPER, SAN™ EXTRA L (Novozymes NS) and CLARASE™ L-40,000, DEXLO™, SPEZYME™ FRED, SPEZYME™ AA, SPEZYME™ ALPHA, SPEZYME™ DELTA AA, GC358, GC980, SPEZYME™ CL and SPEZYME™ RSL (DuPont-Genencor), FUELZYME™ (from Verenium Corp, USA).

In a particular embodiment, the composition according to the invention comprises an alpha amylase, a glucoamylase (AMG), and a pullulanase, and wherein the alpha amylase is selected from *Aspergillus niger* or *Rhizomucor pusillus* alpha amylases, or variants thereof, the glucoamylase is selected from *Aspergillus niger, Talaromyces emersonii, Trametes cingulata* or *Gloeophyllum trabeum* glucoamylases, or variants thereof, and the pullulanase is selected from *Bacillus deramificans* or *Bacillus acidopullulyticus* pullulanases, or hybrids and/or variants thereof.

In further particular embodiments, the composition according to the invention comprises a glucoamylase which comprises/consists essentially of/consists of an amino acid sequence selected from the group consisting of:
  i) The amino acid sequence set forth in any one of SEQ ID NO: 1, 4, 6, 7, 8, 9, 10, 11, 12, 13, 14 and 15 or a mature polypeptide thereof;
  ii) A subsequence of the amino acid sequence set forth in any one of SEQ ID NOs: 1, 4, 6, 7, 8, 9, 10, 11, 12, 13, 14 and 15 or of said mature polypeptide thereof;
  iii) An amino acid sequence, which has at least 70%, such as at least 75%, at least 80%, at least 85%, at least 90%, at least 91%, at least 92%, at least 93%, at least 94%, at least 95%, at least 96%, at least 97%, at least 98%, at least 99%, such as at least 99.5% sequence identity to any one of the amino acids sequences set forth in i) and ii).

When the glucoamylase comprises a subsequence as defined in ii) or an amino acid sequence as defined in iii), it preferably has at least 75%, such as at least 80%, at least 85%, at least 90% or such as at least 95% of the glucoamylase activity of the respective amino acid defined in i) of which it is a subsequence or variant, when tested as set forth above in relation to the definition of "Glucoamylase activity (AGU)".

In other embodiments, the composition according to the invention comprises an alpha-amylase, which comprises/consists essentially of/consists of an amino acid sequence selected from the group consisting of:
  i) The amino acid sequence set forth in any one of SEQ ID NOs: 2, 5, 19, 20, 21, 22, 23, 24 and 25 or a mature polypeptide thereof;
  ii) A subsequence of the amino acid sequence set forth in any one of SEQ ID NOs: 2, 5, 19, 20, 21, 22, 23, 24 and 25 or of said mature polypeptide thereof;
  iii) A variant amino acid sequence, which has at least 70%, such as at least 75%, at least 80%, at least 85%, at least 90%, at least 91%, at least 92%, at least 93%, at least 94%, at least 95%, at least 96%, at least 97%, at least 98%, at least 99%, such as at least 99.5% sequence identity to any one of the amino acids sequences set forth in i) and ii).

When the alpha-amylase defined above is a subsequence or a variant, it preferably has at least 75%, such as at least 80%, at least 85%, at least 90% or such as at least 95% of the alpha-amylase activity of the respective alpha-amylase selected from SEQ ID NOs: 2, 5, 19, 20, 21, 22, 23, 24 and 25 or the mature polypeptide thereof, of which it is a subsequence or variant, when tested as set forth above in relation to the definition of "Acid alpha-Amylase Units (FAU(A))" or "Kilo Novo alpha-amylase Units (KNU)": In the present context an alpha-amylase comprising an amino acid sequences selected from the group consisting of SEQ ID NOs: 2, 5 and 19 or the mature polypeptide thereof, is considered to be a fungal alpha amylase and activity is tested as provided in relation to the above definition of "Acid alpha-Amylase Units (FAU(A))". An alpha-amylase comprising an amino acid sequences selected from the group consisting of SEQ ID NOs: 20-25 or the mature polypeptide thereof is considered to be a bacterial alpha amylase and activity is tested as provided in relation to the above definition of "Kilo Novo alpha-amylase Units (KNU)"

In particular embodiments, the alpha-amylase comprising or consisting of the amino acid sequence defined in iii) is a variant of an alpha-amylase comprising or consisting of the amino sequence defined in SEQ ID NO: 20 or a mature polypeptide thereof, wherein the following mutations have been made: I181*/G182*/N193F (using the amino acid numbering in SEQ ID NO: 20).

According to other embodiments, the alpha-amylase comprising or consisting of the amino acid sequence defined in iii) is a variant of an alpha-amylase comprising or consisting of the amino sequence defined in SEQ ID NO: 23 or a mature polypeptide thereof, wherein the following mutations have been made: H156Y+A181T+N190F+A209V+Q264S (using the amino acid numbering in SEQ ID NO: 21).

In even further embodiments, the alpha-amylase comprising or consisting of the amino acid sequence defined in iii) is a variant of an alpha-amylase comprising or consisting of the amino sequence defined in SEQ ID NO: 23 or a mature polypeptide thereof, wherein the following mutations have been made: G48A+T49I+G107A+H156Y+A181T+N190F+I201F+A209V+Q264S (using the numbering in SEQ ID NO: 21).

In still other embodiments, the composition according to the invention comprises a pullulanase, which comprises/consists essentially of/consists of an amino acid sequence selected from the group consisting of:
  i) The amino acid sequence set forth in any one of SEQ ID NOs: 3, 16, 17 and 18 or a mature polypeptide thereof;
  ii) A subsequence of the amino acid sequence set forth in any one of SEQ ID NOs: 3, 16, 17 and 18 or of said mature polypeptide thereof;
  iii) An amino acid sequence, which has at least 70%, such as at least 75%, at least 80%, at least 85%, at least 90%, at least 91%, at least 92%, at least 93%, at least 94%, at least 95%, at least 96%, at least 97%, at least 98%, at least 99%, such as at least 99.5% sequence identity to any one of the amino acids sequences set forth in i) and ii).

When the pullulanase comprises a subsequence as defined in ii) or a variant amino acid sequence as defined in iii), it preferably has at least 75%, such as at least 80%, at least 85%, at least 90% or such as at least 95% of the pullulanase activity of the respective amino acid defined in i) of which it is a subsequence or variant, when tested as set forth above in relation to the definition of "Pullulanase activity (NPUN)".

Within the scope of the present invention are embodiments wherein the glucoamylase comprises or consists of an amino acid sequence selected from the group consisting of:
i) The amino acid sequence set forth in SEQ ID NO: 4 or a mature polypeptide thereof;
ii) a subsequence of the amino acid sequence set forth in SEQ ID NO: 4 or of said mature polypeptide thereof; and
iii) a variant amino acid sequence, which has at least 70%, such as at least 75%, at least 80%, at least 85%, at least 90%, at least 91%, at least 92%, at least 93%, at least 94%, at least 95%, at least 96%, at least 97%, at least 98%, at least 99%, such as at least 99.5% sequence identity to any one of the amino acids sequences set forth in i) and ii);
wherein the pullulanase comprises or consists of an amino acid sequence selected from the group consisting of:
iv) The amino acid sequence set forth in any one of SEQ ID NOs: 3, 16, 17 and 18 or a mature polypeptide thereof;
v) A subsequence of the amino acid sequence set forth in any one of SEQ ID NOs: 3, 16, 17 and 18 or of said mature polypeptide thereof; and
vi) A variant amino acid sequence, which has at least 70%, such as at least 75%, at least 80%, at least 85%, at least 90%, at least 91%, at least 92%, at least 93%, at least 94%, at least 95%, at least 96%, at least 97%, at least 98%, at least 99%, such as at least 99.5% sequence identity to any one of the amino acids sequences set forth in iv) and v); and
wherein the alpha-amylase comprises or consists of an amino acid sequence selected from the group consisting of:
vii) The amino acid sequence set forth in SEQ ID NO: 5 or a mature polypeptide thereof;
viii) A subsequence of the amino acid sequence set forth in SEQ ID NO: 5 or of said mature polypeptide thereof; and
ix) A variant amino acid sequence, which has at least 70%, such as at least 75%, at least 80%, at least 85%, at least 90%, at least 91%, at least 92%, at least 93%, at least 94%, at least 95%, at least 96%, at least 97%, at least 98%, at least 99%, such as at least 99.5% sequence identity to any one of the amino acids sequences set forth in vii) and viii).

When said glucoamylase is a subsequence or a variant amino acid sequence as defined above, it preferably has at least 75%, such as at least 80%, at least 85%, at least 90% or such as at least 95% of the glucoamylase activity of the respective amino acid sequence (e.g. the amino acid sequence set forth in SEQ ID NO: 4 or a mature polypeptide thereof) of which it is a subsequence or variant, when tested as set forth above in relation to the definition of "Glucoamylase activity (AGU)".

When said pullulanase is a subsequence or a variant amino acid sequence as defined above, it preferably has at least 75%, such as at least 80%, at least 85%, at least 90% or such as at least 95% of the pullulanase activity of the respective amino acid sequence (e.g. the amino acid sequence set forth in any one of SEQ ID NOs: 3, 16, 17 and 18 or a mature polypeptide thereof) of which it is a subsequence or variant, when tested as set forth above in relation to the definition of "Pullulanase activity (NPUN)".

When the alpha-amylase defined above is a subsequence or a variant, it preferably has at least 75%, such as at least 80%, at least 85%, at least 90% or such as at least 95% of the alpha-amylase activity of the respective alpha-amylase selected from SEQ ID NOs: 5 or of the mature polypeptide thereof, of which it is a subsequence or variant, when tested as set forth above in relation to the definition of "Acid alpha-Amylase Units (FAU(A))".

In a particular embodiment, the glucoamylase is selected from the glucoamylase disclosed in SEQ ID NO: 1 or the mature polypeptide thereof, and a glucoamylase having a sequence identity to the polypeptide of SEQ ID NO: 1 or the mature polypeptide thereof, of at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which has glucoamylase activity; e.g. at least 75%, such as at least 80%, at least 85%, at least 90% or such as at least 95% of the glucoamylase activity of the glucoamylase disclosed in SEQ ID NO: 1 or the mature polypeptide thereof, when tested as set forth above in relation to the definition of "Glucoamylase activity (AGU)".

In another particular embodiment, the glucoamylase is selected from the glucoamylase disclosed in SEQ ID NO: 4 or the mature polypeptide thereof, and a glucoamylase having a sequence identity to the mature polypeptide of SEQ ID NO: 4 or the mature polypeptide thereof, of at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which has glucoamylase activity; e.g. at least 75%, such as at least 80%, at least 85%, at least 90% or such as at least 95% of the glucoamylase activity of the glucoamylase disclosed in SEQ ID NO: 4 or the mature polypeptide thereof, when tested as set forth above in relation to the definition of "Glucoamylase activity (AGU)".

In a particular embodiment, the alpha-amylase is selected from the alpha-amylase disclosed in SEQ ID NO: 2 or an alpha-amylase having a sequence identity to the polypeptide of SEQ ID NO: 2 or the mature polypeptide thereof, of at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which has alpha-amylase activity; e.g. e.g. at least 75%, such as at least 80%, at least 85%, at least 90% or such as at least 95% of the alpha-amylase activity of the alpha-amylase disclosed in SEQ ID NO: 2 or the mature polypeptide thereof, when tested as set forth above in relation to the definition of "Acid alpha-Amylase Units (FAU(A))". In another particular embodiment the alpha-amylase is selected from the alpha-amylases disclosed in SEQ ID NO: 5 or an alpha-amylase having a sequence identity to the polypeptide of SEQ ID NO: 5 or the mature polypeptide thereof, of at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which has alpha-amylase activity; e.g. at least 75%, such as at least 80%, at least 85%, at least 90% or such as at least 95% of the alpha-amylase activity of the alpha-amylase disclosed in SEQ ID NO: 5 or the mature polypeptide thereof, when tested as set forth above in relation to the definition of "Acid alpha-Amylase Units (FAU(A))".

In a particular embodiment, the pullulanase is selected from the pullulanase disclosed in SEQ ID NO: 3 or the mature polypeptide thereof, and a pullulanase having a sequence identity to the polypeptide of SEQ ID NO: 3 or the mature polypeptide thereof, of at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which has pullulanase activity; e.g. at least 75%, such as at least 80%, at least 85%, at least 90% or such as at least 95% of the pullulanase activity of the amino acid sequence set forth in SEQ ID NO: 3 or a mature polypeptide thereof, when tested as set forth above in relation to the definition of "Pullulanase activity (NPUN)".

In a further specific embodiment, the composition comprises
i) a glucoamylase is selected from the glucoamylases disclosed in SEQ ID NO: 1 or the mature polypeptide thereof, and a glucoamylase having a sequence identity to the mature polypeptide of SEQ ID NO: 1 of at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which has glucoamylase activity; e.g. at least 75%, such as at least 80%, at least 85%, at least 90% or such as at least 95% of the glucoamylase activity of the glucoamylases disclosed in SEQ ID NO: 1 or the mature polypeptide thereof, when tested as set forth above in relation to the definition of "Glucoamylase activity (AGU)";
ii) an alpha-amylase selected from the alpha-amylase disclosed in SEQ ID NO: 2 or the mature polypeptide thereof, and an alpha-amylase having a sequence identity to the mature polypeptide of SEQ ID NO: 2 of at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which has alpha-amylase activity; e.g. at least 75%, such as at least 80%, at least 85%, at least 90% or such as at least 95% of the alpha-amylase activity of the alpha-amylase disclosed in SEQ ID NO: 2 or the mature polypeptide thereof, when tested as set forth above in relation to the definition of "Acid alpha-Amylase Units (FAU(A))"; and
iii) a pullulanase selected from a pullulanase disclosed in SEQ ID NO: 3 or the mature polypeptide thereof, and a pullulanase having a sequence identity to the mature polypeptide of SEQ ID NO: 3 of at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which has pullulanase activity; e.g. at least 75%, such as at least 80%, at least 85%, at least 90% or such as at least 95% of the pullulanase activity of the amino acid sequence set forth in SEQ ID NO: 3 or a mature polypeptide thereof, when tested as set forth above in relation to the definition of "Pullulanase activity (NPUN)".

Particularly, the composition may comprise:
i) a glucoamylase selected from the glucoamylase disclosed in SEQ ID NO: 1 or the mature polypeptide thereof, and a glucoamylase having a sequence identity to the mature polypeptide of SEQ ID NO: 1 or the mature polypeptide thereof, of at least 90% which has glucoamylase activity; e.g. at least 90% of the glucoamylase activity of the glucoamylase disclosed in SEQ ID NO: 1 or the mature polypeptide thereof, when tested as set forth above in relation to the definition of "Glucoamylase activity (AGU)";
ii) an alpha-amylase selected from the alpha-amylase disclosed in SEQ ID NO: 2 or the mature polypeptide thereof, and an alpha-amylase having a sequence identity to the mature polypeptide of SEQ ID NO: 2 or the mature polypeptide thereof of at least 90%, which has alpha-amylase activity; e.g. at least 90% of the alpha-amylase activity of the alpha-amylase disclosed in SEQ ID NO: 2 or the mature polypeptide thereof, when tested as set forth above in relation to the definition of "Acid alpha-Amylase Units (FAU(A))"; and
iii) a pullulanase selected from a pullulanase disclosed in SEQ ID NO: 3 or the mature polypeptide thereof, and a pullulanase having a sequence identity to the mature polypeptide of SEQ ID NO: 3 or the mature polypeptide thereof of at least 90%, which has pullulanase activity; e.g. at least 90% of the pullulanase activity of the amino acid sequence set forth in SEQ ID NO: 3 or a mature polypeptide thereof, when tested as set forth above in relation to the definition of "Pullulanase activity (NPUN)".

Particularly, the composition may comprise:
i) a glucoamylase selected from the glucoamylase disclosed in SEQ ID NO: 1 or the mature polypeptide thereof, and a glucoamylase having a sequence identity to the glucoamylase of SEQ ID NO: 1 or the mature polypeptide thereof of at least 95% which has glucoamylase activity; e.g. at least 95% of the glucoamylase activity of the glucoamylases disclosed in SEQ ID NO: 1 or the mature polypeptide thereof, when tested as set forth above in relation to the definition of "Glucoamylase activity (AGU)";
ii) an alpha-amylase selected from the alpha-amylase disclosed in SEQ ID NO: 2 or the mature polypeptide thereof, and an alpha-amylase having a sequence identity to the mature polypeptide of SEQ ID NO: 2 of at least 95%, which has alpha-amylase activity; e.g. at least 95% of the alpha-amylase activity of the alpha-amylase disclosed in SEQ ID NO: 2 or the mature polypeptide thereof, when tested as set forth above in relation to the definition of "Acid alpha-Amylase Units (FAU(A))";
iii) and a pullulanase selected from a pullulanase disclosed in SEQ ID NO: 3 or the mature polypeptide thereof, and a pullulanase having a sequence identity to the mature polypeptide of SEQ ID NO: 3 of at least 95%, which has pullulanase activity; e.g. at least 95% of the pullulanase activity of the amino acid sequence set forth in SEQ ID NO: 3 or the mature polypeptide thereof, when tested as set forth above in relation to the definition of "Pullulanase activity (NPUN)".

Particularly, the composition may comprise:
i) a glucoamylase selected from the glucoamylase disclosed in SEQ ID NO: 1 or the mature polypeptide thereof, and a glucoamylase having a sequence identity to the mature polypeptide of SEQ ID NO: 1 of at least 97% which has glucoamylase activity; e.g. at least 95% of the glucoamylase activity of the glucoamylases disclosed in SEQ ID NO: 1 or the mature polypeptide thereof, when tested as set forth above in relation to the definition of "Glucoamylase activity (AGU)";
ii) an alpha-amylase selected from the alpha-amylase disclosed in SEQ ID NO: 2 or the mature polypeptide thereof, and an alpha-amylase having a sequence identity to the mature polypeptide of SEQ ID NO: 2 of at least 97%, which has alpha-amylase activity; e.g. at least 95% of the alpha-amylase activity of the alpha-amylase disclosed in SEQ ID NO: 2 or the mature polypeptide thereof, when tested as set forth above in relation to the definition of "Acid alpha-Amylase Units (FAU(A))";
iii) and a pullulanase selected from a pullulanase disclosed in SEQ ID NO: 3 or the mature polypeptide thereof, and a pullulanase having a sequence identity to the mature polypeptide of SEQ ID NO: 3 of at least 97%, which has pullulanase activity; e.g. at least 95% of the pullulanase activity of the amino acid sequence set forth in SEQ ID NO: 3 or a mature polypeptide thereof, when tested as set forth above in relation to the definition of "Pullulanase activity (NPUN)".

Particularly, the composition may comprise:
i) a glucoamylase selected from the glucoamylases disclosed in SEQ ID NO: 1 or the mature polypeptide thereof, and a glucoamylase having a sequence identity to the mature polypeptide of SEQ ID NO: 1 of at least 99% which has glucoamylase activity; e.g. at least 95% of the glucoamylase activity of the glucoamylase disclosed in SEQ ID NO: 1 or the mature polypeptide thereof, when tested as set forth above in relation to the definition of "Glucoamylase activity (AGU)";

ii) an alpha-amylase selected from the alpha-amylase disclosed in SEQ ID NO: 2 or the mature polypeptide thereof, and an alpha-amylase having a sequence identity to the mature polypeptide of SEQ ID NO: 2 of at least 99%, which has alpha-amylase activity; e.g. at least 95% of the alpha-amylase activity of the alpha-amylase disclosed in SEQ ID NO: 2 or the mature polypeptide thereof, when tested as set forth above in relation to the definition of "Acid alpha-Amylase Units (FAU(A))";

iii) and a pullulanase selected from a pullulanase disclosed in SEQ ID NO: 3 or the mature polypeptide thereof, and a pullulanase having a sequence identity to the mature polypeptide of SEQ ID NO: 3 of at least 99%, which has pullulanase activity; e.g. at least 95% of the pullulanase activity of the amino acid sequence set forth in SEQ ID NO: 3 or a mature polypeptide thereof, when tested as set forth above in relation to the definition of "Pullulanase activity (NPUN)".

In a further specific embodiment, the composition comprises:

i) a glucoamylase is selected from the glucoamylase disclosed in SEQ ID NO: 4 or the mature polypeptide thereof, and a glucoamylase having a sequence identity to the mature polypeptide of SEQ ID NO: 4 of at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which has glucoamylase activity; e.g. at least 75%, such as at least 80%, at least 85%, at least 90% or such as at least 95% of the glucoamylase activity of the glucoamylase disclosed in SEQ ID NO: 4 or the mature polypeptide thereof, when tested as set forth above in relation to the definition of "Glucoamylase activity (AGU)";

ii) an alpha-amylase selected from the alpha-amylase disclosed in SEQ ID NO: 5 or the mature polypeptide thereof, and an alpha-amylase having a sequence identity to the mature polypeptide of SEQ ID NO: 5 of at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which has alpha-amylase activity; e.g. at least 75%, such as at least 80%, at least 85%, at least 90% or such as at least 95% of the alpha-amylase activity of the alpha-amylase disclosed in SEQ ID NO: 5 or the mature polypeptide thereof, when tested as set forth above in relation to the definition of "Acid alpha-Amylase Units (FAU(A))", and iii) a pullulanase selected from a pullulanase disclosed in SEQ ID NO: 3 or the mature polypeptide thereof, and a pullulanase having a sequence identity to the mature polypeptide of SEQ ID NO: 3 of at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which has pullulanase activity; e.g. at least 75%, such as at least 80%, at least 85%, at least 90% or such as at least 95% of the pullulanase activity of the amino acid sequence set forth in SEQ ID NO: 3 or a mature polypeptide thereof, when tested as set forth above in relation to the definition of "Pullulanase activity (NPUN)".

Particularly, the composition may comprise:

i) a glucoamylase selected from the glucoamylase disclosed in SEQ ID NO: 4 or the mature polypeptide thereof, and a glucoamylase having a sequence identity to the mature polypeptide of SEQ ID NO: 4 of at least 90% which has glucoamylase activity e.g. at least 90% of the glucoamylase activity of the glucoamylase disclosed in SEQ ID NO: 4 or the mature polypeptide thereof, when tested as set forth above in relation to the definition of "Glucoamylase activity (AGU)";

ii) an alpha-amylase selected from the alpha-amylase disclosed in SEQ ID NO: 5 or the mature polypeptide thereof, and an alpha-amylase having a sequence identity to the mature polypeptide of SEQ ID NO: 5 of at least 90%, which has alpha-amylase activity; e.g. at least 95% of the alpha-amylase activity of the alpha-amylase disclosed in SEQ ID NO: 5 or the mature polypeptide thereof, when tested as set forth above in relation to the definition of "Acid alpha-Amylase Units (FAU(A))"; and iii) a pullulanase selected from a pullulanase disclosed in SEQ ID NO: 3 or the mature polypeptide thereof, and a pullulanase having a sequence identity to the mature polypeptide of SEQ ID NO: 3 of at least 90%, which has pullulanase activity e.g. at least 90% of the pullulanase activity of the amino acid sequence set forth in SEQ ID NO: 3 or a mature polypeptide thereof, when tested as set forth above in relation to the definition of "Pullulanase activity (NPUN)".

Particularly, the composition may comprise:

i) a glucoamylase selected from the glucoamylase disclosed in SEQ ID NO: 4 or the mature polypeptide thereof, and a glucoamylase having a sequence identity to the mature polypeptide of SEQ ID NO: 4 of at least 95% which has glucoamylase activity e.g. at least 95% of the glucoamylase activity of the glucoamylase disclosed in SEQ ID NO: 4 or the mature polypeptide thereof, when tested as set forth above in relation to the definition of "Glucoamylase activity (AGU)";

ii) an alpha-amylase selected from the alpha-amylase disclosed in SEQ ID NO: 5 or the mature polypeptide thereof, and an alpha-amylase having a sequence identity to the mature polypeptide of SEQ ID NO: 5 of at least 95%, which has alpha-amylase activity; e.g. at least 95% of the alpha-amylase activity of the alpha-amylase disclosed in SEQ ID NO: 5 or the mature polypeptide thereof, when tested as set forth above in relation to the definition of "Acid alpha-Amylase Units (FAU(A))"; and iii) a pullulanase selected from a pullulanase disclosed in SEQ ID NO: 3 or the mature polypeptide thereof, and a pullulanase having a sequence identity to the mature polypeptide of SEQ ID NO: 3 of at least 95%, which has pullulanase activity; e.g. at least 95% of the pullulanase activity of the amino acid sequence set forth in SEQ ID NO: 3 or a mature polypeptide thereof, when tested as set forth above in relation to the definition of "Pullulanase activity (NPUN)".

Particularly, the composition may comprise:

i) a glucoamylase selected from the glucoamylase disclosed in SEQ ID NO: 4 or the mature polypeptide thereof, and a glucoamylase having a sequence identity to the mature polypeptide of SEQ ID NO: 4 of at least 97% which has glucoamylase activity e.g. at least 95% of the glucoamylase activity of the glucoamylase disclosed in SEQ ID NO: 4 or the mature polypeptide thereof, when tested as set forth above in relation to the definition of "Glucoamylase activity (AGU)";

ii) an alpha-amylase selected from the alpha-amylase disclosed in SEQ ID NO: 5 or the mature polypeptide thereof, and an alpha-amylase having a sequence identity to the mature polypeptide of SEQ ID NO: 5 of at least 97%, which has alpha-amylase activity; e.g. at least 95% of the alpha-amylase activity of the alpha-amylase disclosed in SEQ ID NO: 5 or the mature polypeptide thereof, when tested as set forth above in relation to the definition of "Acid alpha-Amylase Units (FAU(A))"; and iii) a pullulanase selected from a pullulanase disclosed in SEQ ID NO: 3 or the mature polypeptide thereof, and a pullulanase having a sequence identity to the mature polypeptide of SEQ ID NO: 3 of at least 97%, which has pullulanase activity e.g. at least 95% of the pullulanase activity of the amino acid sequence set forth in SEQ ID NO: 3 or a mature polypeptide thereof, when tested as set forth above in relation to the definition of "Pullulanase activity (NPUN)".

Particularly, the composition may comprise:

i) a glucoamylase selected from the glucoamylases disclosed in SEQ ID NO: 4 or the mature polypeptide thereof, and a glucoamylase having a sequence identity to the mature polypeptide of SEQ ID NO: 4 of at least 99% which has glucoamylase activity e.g. at least 95% of the glucoamylase activity of the glucoamylase disclosed in SEQ ID NO: 4 or the mature polypeptide thereof, when tested as set forth above in relation to the definition of "Glucoamylase activity (AGU)";

ii) an alpha-amylase selected from the alpha-amylase disclosed in SEQ ID NO: 5 or the mature polypeptide thereof, and an alpha-amylase having a sequence identity to the mature polypeptide of SEQ ID NO: 5 of at least 99%, which has alpha-amylase activity; e.g. at least 95% of the alpha-amylase activity of the alpha-amylase disclosed in SEQ ID NO: 5 or the mature polypeptide thereof, when tested as set forth above in relation to the definition of "Acid alpha-Amylase Units (FAU(A))";

iii) and a pullulanase selected from a pullulanase disclosed in SEQ ID NO: 3 or the mature polypeptide thereof, and a pullulanase having a sequence identity to the mature polypeptide of SEQ ID NO: 3 of at least 99%, which has pullulanase activity; e.g. at least 95% of the pullulanase activity of the amino acid sequence set forth in SEQ ID NO: 3 or a mature polypeptide thereof, when tested as set forth above in relation to the definition of "Pullulanase activity (NPUN)".

The compositions may be prepared in accordance with methods known in the art and may be in the form of a liquid or a dry composition. The compositions may be stabilized in accordance with methods known in the art.

Uses

The composition according to the invention may be used in a saccharification process to produce glucose syrup. Therefore in a further aspect, the invention relates to a method of making glucose syrup from liquefied starch comprising, contacting the liquefied starch with a composition according to the invention.

The present invention is further described by the following examples that should not be construed as limiting the scope of the invention.

EXAMPLES

Material and Methods
Glucoamylase Activity
Glucoamylase Activity (AGU)

The Glucoamylase Unit (AGU) is defined as the amount of enzyme, which hydrolyzes 1 micromole maltose per minute under the standard conditions (37° C., pH 4.3, substrate: maltose 100 mM, buffer: acetate 0.1 M, reaction time 6 minutes as set out in the glucoamylase incubation below), thereby generating glucose.

| glucoamylase incubation: | |
| --- | --- |
| Substrate: | maltose 100 mM |
| Buffer: | acetate 0.1M |
| pH: | 4.30 ± 0.05 |
| Incubation temperature: | 37° C. ± 1 |
| Reaction time: | 6 minutes |
| Enzyme working range: | 0.5-4.0 AGU/mL |

The analysis principle is described by 3 reaction steps:
Step 1 is an enzyme reaction:
Glucoamylase (AMG), EC 3.2.1.3 (exo-alpha-1,4-glucan-glucohydrolase), hydrolyzes maltose to form alpha-D-glucose. After incubation, the reaction is stopped with NaOH.
Steps 2 and 3 result in an endpoint reaction:
Glucose is phosphorylated by ATP, in a reaction catalyzed by hexokinase. The glucose-6-phosphate formed is oxidized to 6-phosphogluconate by glucose-6-phosphate dehydrogenase. In this same reaction, an equimolar amount of NAD+ is reduced to NADH with a resulting increase in absorbance at 340 nm. An autoanalyzer system such as Konelab 30 Analyzer (Thermo Fisher Scientific) may be used.

| Color reaction | |
| --- | --- |
| Tris | approx. 35 mM |
| ATP | 0.7 mM |
| NAD+ | 0.7 mM |
| $Mg^{2+}$ | 1.8 mM |
| Hexokinase | >850 U/L |
| Glucose-6-P-DH | >850 U/L |
| pH | approx. 7.8 |
| Temperature | 37.0° C. ± 1.0° C. |
| Reaction time | 420 sec |
| Wavelength | 340 nm |

Acid Alpha-Amylase Activity

When used according to the present invention, the activity of any acid alpha-amylase may be measured in FAU(A) (Acid Fungal Alpha-amylase Units).
Acid Alpha-Amylase Activity (FAU(A))

Acid alpha-amylase activity may be measured in FAU(A) (Acid Fungal Alpha-amylase Units). 1 FAU(A) is defined as the amount of enzyme which degrades 5.260 mg starch dry matter per hour under standard conditions.

Acid alpha-amylase, an endo-alpha-amylase (1,4-alpha-D-glucan-glucanohydrolase, E.C. 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions.

FAU(A), the acid alpha-amylase activity is determined in accordance with the following description, and is measured relative to a Novozymes standard which is available on request from Novozymes NS, Denmark. The principle of the reaction is based on the two steps. In the first step the enzyme acid alpha-amylase hydrolyzes starch into different oligosaccharides. In the second step iodine forms a blue complex with starch but not with its degradation products.

The intensity of color is therefore directly proportional to the concentration of starch. The activity is determined using reverse colorimetry as a reduction in the concentration of starch under specified analytic conditions.

| First reaction, starch degradation | |
|---|---|
| Substrate | Starch, approx. 0.3 g/L |
| Buffer | Citrate, approx. 0.05M |
| | CaCl2, 1.85 mM |
| pH | 2.50 ± 0.05 |
| Incubation temperature | 37° C. |
| Reaction time | 180 seconds |
| Enzyme working range | 0.01-0.04 FAU(A)/mL |

| Second reaction, starch-iodine complex | |
|---|---|
| Iodine | 0.0432 g/L |
| Incubation temperature | 37° C. |
| Reaction time | 60 seconds |
| Wavelength | 600 nm |

If further details are preferred, these can be found in EB-SM-0510.02 available on request from Novozymes NS, Denmark, and incorporated by reference Pullulanase Activity Endo-pullulanases hydrolyse α-1,6-glycosidic bonds in pullulan (—BH4 reduced to reduce background reducing sugar), releasing maltotriose units with reducing carbohydrate ends. Pullulanase is a pullulan 6-glucano-hydrolase with the enzyme classification number E.C.3.2.1.41.

The NPUN (New Pullulanase Unit Novozymes) is a unit of endopullulanase activity measured in the following procedure, and is measured relative to a Novozymes standard which is available on request from Novozymes NS, Denmark.

1 NPUN=One pullulanase unit (NPUN) is defined as the enzyme amount, which releases reducing ends equivalent to 0.35 μmol glucose per minute under the standard conditions.

In the first reaction, the substrate is equally present in both sample main and sample blank. However, the reaction of sample main is performed at pH 5.0, while there is no reaction in the sample blank at pH 9.6, where neither pullulanases nor amyloglucosidases (glucoamylase) are enzymatically active.

| First reaction, pullulan degradation | |
|---|---|
| Substrate | BH4 reduced pullulan, 5.3 g/L |
| Buffer (main) | Acetate, approx. 0.1M |
| | EDTA, 5.3 mM |
| | Acarbose, 0.018% |
| | (if sample contains glucoamylase) |
| pH (main) | 5.0 |
| Buffer (blank) | CHES, 42 mM |
| | acetate, 17 mM |
| | EDTA, 5.3 mM |
| pH (blank) | 9.6 |
| Incubation temperature | 50° C. |
| Reaction time | 540 seconds |
| Enzyme working range | 0.03-0.15 NPUN/mL |

In the second reaction, the pH was adjusted to approx. 9.6 and the glucose in samples is phosphorylated to non-reducing D-glucose-6-phosphate by glucokinase, which has optimal activity and stability in this range and is specific to glucose at pH 9 (ref. Goward, Biochem. J. 1986, 237, pp 415-420). This step depends on identical pH in sample main and sample blank to remove equal amounts of glucose in both.

| Second reaction, background glucose elimination | |
|---|---|
| Substrate | glucose in sample, after first reaction |
| Buffer | CHES, 58 mM (main) or 76 mM (blank) |
| | acetate, 43 mM (main) or 7.2 mM (blank) |
| | EDTA, 2.2 mM |
| | ATP, 1.11 mg/ml |
| | MgCl2, 4.4 mM |
| Glucokinase | 0.11 U/ml |
| pH | approx. 9.6 |
| Incubation temperature | 50° C. |
| Reaction time | 720 seconds |

The second reaction is stopped by and alkaline reagent >pH 11 containing PAHBAH (p-Hydroxy benzoic acid hydrazide) and bismuth, which complexes with reducing sugars to produce color detected at 405 nm. The produced color is proportional to the pullulanase activity.

| Third reaction, PAHBAH-Bi reaction | |
|---|---|
| Substrate | maltotriose formed by pullulanase, after second reaction |
| PAHBAH | 56 mM |
| Tartrate | 75 mM |
| $Bi^{3+}$ | 6.0 mM |
| NaOH | 195 mM |
| pH | alkaline |
| Incubation temperature | 50° C. |
| Reaction time | 1000 seconds |
| Wavelength | 405 nm |

If further details are preferred, these can be found in 2010-28835-02 available on request from Novozymes NS, Denmark, and incorporated by reference.

Example 1

Maltodextrin which dextrose equivalent (DE) was adjusted to 11 was prepared from a conventional starch liquefaction process using corn starch and spray-dried for this experiment. The maltodextrin powder was dissolved in milliQ water and the pH was adjusted by HCl/NaOH to be 4.3 at 60° C., and then the solid was adjusted to 33% dry solid (DS) by measuring refractive index (RI) of the syrup. Saccharification was started by mixing 18 g maltodextrin solution and 2 ml enzyme mixture containing *Aspergillus niger* glucoamylase (SEQ ID NO: 1), pullulanase (Promozyme D2®) (SEQ ID NO: 3), and *Aspergillus niger* acid alpha-amylase (SEQ ID NO: 2) at different dosages. The samples were incubated at 60° C. with stirring and were taken at different time intervals for determination of sugar component. The enzyme dosages and the DP1-DP4+ compositions at the time point that DP1 fraction is maximized were shown in Table 1.

| A. niger glucoamylase (SEQ ID NO: 1) AGU/gDS | A. niger alpha-amylase (SEQ ID NO: 2) FAU(A)/ gDS | Promozyme D2 ® (SEQ ID NO: 3) NPUN/gDS | NPUN/FAU(A) | Peak time hr | DP1 % | DP2 % | DP3 % | DP4 + % | Comment |
|---|---|---|---|---|---|---|---|---|---|
| 0.18 | 0.045 | 0.34 | 7.56 | 48 | 95.6 | 2.4 | 0.5 | 1.4 | Dextrozyme |
| 0.18 | 0.011 | 0.34 | 30.22 | 72 | 95.3 | 2.8 | 0.4 | 1.5 | DX ® |
| 0.18 | 0.023 | 0.34 | 15.11 | 60 | 95.4 | 2.6 | 0.5 | 1.5 | |
| 0.18 | 0.045 | 0.34 | 7.56 | 48 | 95.5 | 2.4 | 0.6 | 1.5 | |
| 0.18 | 0.09 | 0.34 | 3.78 | 48 | 95.4 | 2.4 | 0.7 | 1.5 | |
| 0.18 | 0.18 | 0.34 | 1.89 | 48 | 95.4 | 2.4 | 0.7 | 1.5 | |
| 0.18 | 0.011 | 1.01 | 89.78 | 36 | 95.9 | 2.1 | 0.6 | 1.4 | |
| 0.18 | 0.023 | 1.01 | 44.89 | 48 | 95.8 | 2.4 | 0.6 | 1.3 | |
| 0.18 | 0.045 | 1.01 | 22.44 | 36 | 95.6 | 2.2 | 0.8 | 1.5 | |
| 0.18 | 0.09 | 1.01 | 11.22 | 60 | 95.5 | 2.6 | 0.6 | 1.3 | |
| 0.18 | 0.18 | 1.01 | 5.61 | 48 | 95.5 | 2.4 | 0.8 | 1.4 | |

Table 1 shows that the enzyme blends with NPUN/FAU (A) ratio higher than 44.89 showed higher DP1 fraction than Dextrozyme DX®. Even at 3-times higher NPUN activity (1.01 NPUN/gDS) than Dextrozyme DX, the peak DP1 was not as high as Dextrozyme DX at higher FAU(A) activity than 0.045.

Example 2

Saccharification Using Different Enzyme Blends

Maltodextrin powder from corn starch liquefaction was dissolved in water while heating to make slurry at 34.4% dry solids. The solid content of the slurry was measured using Refractive index measurement showing 1.39271. The slurry was adjusted to a pH of 4.3 using a 1M Hydrochloric acid solution. 18 gram aliquots of this slurry were added to 18 glass reaction scintillation vials with septum cap closures and were inserted in a heating block to be heated to a temperature of 61° C. Each vial was given an enzyme dosage based on the table below and additional water was added to each vial to reach a target dry solid of 33%. The enzyme blend comprised a glucoamylase derived from *Gloeophyllum trabeum* (SEQ ID NO: 4), an alpha-amylase derived from *Rhizomucor pusillus* (SED ID NO: 5) and a pullulanase derived from *Bacillus deramificans* (SEQ ID NO: 3). 1.5 mL samples were taken via needles through the septum from each vial at different time points (36 hour, 42 hour, 48 hour, 54 hours and 60 hours) and were deactivated at 105° C. for 5 minutes. 1 mL of each deactivated sample was diluted with 4 mL deionized water. The diluted samples were evaluated using a HPLC method DP1-4 for measuring dextrose purity (% DP1 or % DX).

Results from Table 2 show the higher the NPUN/FAU(A) ratio, the higher the percent dextrose.

TABLE 2

| GA SEQ ID NO: 4 Dose (AGU/g DS) | AA SEQ ID NO: 5 Dose (FAU(A)/ g DS) | PUL SEQ ID NO: 3 Dose (NPUN/ g DS) | NPUN/FAU(A) ratio | % DX 36 hr | % DX 42 hr | % DX 48 hr | % DX 54 hr | % DX 60 hr |
|---|---|---|---|---|---|---|---|---|
| 0.18 | 0 | 0.72 | N/A | 92.2 | 93.5 | 94.6 | 95.3 | 95.8 |
| 0.18 | 0 | 1.08 | N/A | 93.5 | 94.8 | 95.6 | 96.1 | 96.5 |
| 0.18 | 0.008 | 0.9 | 112.5 | 94.1 | 95.2 | 95.5 | 95.8 | 95.8 |
| 0.18 | 0.008 | 0.9 | 112.5 | 94.4 | 95.3 | 95.7 | 95.9 | 96.0 |
| 0.18 | 0.015 | 0.72 | 48 | 93.6 | 94.8 | 95.3 | 95.5 | 95.6 |
| 0.18 | 0.015 | 1.08 | 72 | 94.0 | 94.9 | 95.3 | 95.5 | 95.6 |
| 0.23 | 0 | 0.9 | N/A | 94.1 | 95.0 | 95.6 | 96.0 | 96.3 |
| 0.23 | 0.008 | 0.72 | 90 | 95.5 | 95.8 | 96.0 | 96.0 | 96.0 |
| 0.23 | 0.008 | 0.9 | 112.5 | 95.5 | 95.8 | 95.9 | 96.0 | 96.0 |
| 0.23 | 0.008 | 1.08 | 135 | 95.7 | 96.0 | 96.0 | 96.0 | 96.1 |
| 0.23 | 0.008 | 1.08 | 135 | 95.7 | 95.9 | 96.0 | 96.1 | 96.0 |
| 0.23 | 0.015 | 0.9 | 60 | 95.3 | 95.7 | 95.8 | 95.8 | 95.9 |
| 0.23 | 0.015 | 0.9 | 60 | 95.0 | 95.5 | 95.6 | 95.8 | 95.7 |
| 0.28 | 0 | 0.72 | N/A | 94.6 | 95.5 | 95.8 | 96.1 | 96.1 |
| 0.28 | 0 | 1.08 | N/A | 95.7 | 96.3 | 96.3 | 96.6 | 96.4 |
| 0.28 | 0.008 | 0.9 | 112.5 | 95.9 | 96.0 | 96.0 | 96.0 | 96.0 |
| 0.28 | 0.015 | 0.72 | 48 | 95.8 | 95.9 | 95.9 | 95.9 | 95.9 |
| 0.28 | 0.015 | 1.08 | 72 | 95.7 | 95.7 | 95.8 | 95.9 | 95.8 |

In a different experiment, performed according to the same procedure as above, results are shown in Table 3.

TABLE 3

| AA SEQ ID NO: 5 AA dose (AFAU/gDS) | PUL SEQ ID NO: 3 dose (NPUN/gDS) | GA SEQ ID NO: 4 AMG dose (AGU/gDS) | NPUN/AFAU ratio | % DX at 36 hr | % DX at 42 hr | % DX at 48 hr | % DX at 60 hr |
|---|---|---|---|---|---|---|---|
| 0.0 | 0.96 | 0.25 | N/A | 96.2 | 96.6 | 96.7 | 96.8 |
| 0.001 | 0.96 | 0.25 | 960 | 96.8 | 96.7 | 96.7 | 96.6 |
| 0.002 | 0.96 | 0.25 | 480 | 96.6 | 96.6 | 96.6 | 96.5 |
| 0.003 | 0.96 | 0.25 | 320 | 96.3 | 96.4 | 96.5 | 96.3 |
| 0.005 | 0.96 | 0.25 | 191 | 96.2 | 96.3 | 96.2 | 96.2 |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A composition comprising an alpha-amylase, a pullulanase and a glucoamylase, wherein
   the alpha-amylase has at least 90% sequence identity to SEQ ID NO: 5 or a mature polypeptide thereof,
   the pullulanase has at least 90% sequence identity to SEQ ID NO: 16 or a mature polypeptide thereof,
   the glucoamylase has at least 90% sequence identity to SEQ ID NO: 4 or a mature polypeptide thereof, and
   the ratio of pullulanase dose in New Pullulanase Units Novozymes (NPUN)/gDS to alpha-amylase dose in Acid Fungal Alpha-amylase Units (FAU(A))/gDS is at least 60 and the ratio of pullulanase dose in New Pullulanase Units Novozymes (NPUN)/gDS to glucoamylase dose in Glucoamylase Units (AGU)/gDS is in the range of 2-15.

2. The composition of claim 1, wherein the ratio of pullulanase dose in NPUN/gDS to alpha-amylase dose in FAU(A)/gDS is in the range of 100-700.

3. The composition of claim 1, wherein the ratio of pullulanase dose in NPUN/gDS to alpha-amylase dose in FAU(A)/gDS is in the range of 200-600.

4. The composition of claim 1, wherein the ratio of pullulanase dose in NPUN/gDS to alpha-amylase dose in FAU(A)/gDS is in the range of 300-500.

5. The composition of claim 1, wherein the ratio of pullulanase dose in NPUN/gDS to alpha-amylase dose in FAU(A)/gDS is in the range of 350-500.

6. The composition of claim 1, wherein the ratio of pullulanase dose in NPUN/gDS to alpha-amylase dose in FAU(A)/gDS is in the range of 375-475.

7. The composition of claim 1, wherein the ratio of pullulanase dose in NPUN/gDS to alpha-amylase dose in FAU(A)/gDS is in the range of 400-450.

8. The composition of claim 1, wherein the ratio of pullulanase dose in NPUN/gDS to glucoamylase dose in AGU/gDS is in the range of 2-10.

9. The composition of claim 1, wherein the ratio of pullulanase dose in NPUN/gDS to glucoamylase dose in AGU/gDS is in the range of 2-5.

10. The composition of claim 1, wherein the ratio of pullulanase dose in NPUN/gDS to glucoamylase dose in AGU/gDS is in the range of 3-5.

11. The composition of claim 1, wherein the ratio of pullulanase dose in NPUN/gDS to glucoamylase dose in AGU/gDS is in the range of 3.5-4.

12. The composition of claim 1, wherein the composition comprises an alpha-amylase of SEQ ID NO: 5, a pullulanase of SEQ ID NO: 16 and a glucoamylase of SEQ ID NO: 4.

13. A method of making glucose syrup, comprising contacting liquefied starch with a composition of claim 1.

14. The method of claim 13, wherein the initial dry solids content (DS) in the liquefied starch is at least 25%.

15. The method of claim 13, wherein contacting time is at least 24 hours.

* * * * *